United States Patent
Dax et al.

(10) Patent No.: US 7,553,850 B2
(45) Date of Patent: *Jun. 30, 2009

(54) TRICYCLIC-BRIDGED PIPERIDINYLIDENE DERIVATIVES AS δ-OPIOID MODULATORS

(75) Inventors: Scott Dax, Landenberg, PA (US); Bart DeCorte, Southhampton, PA (US); Li Liu, Doylestown, PA (US); Mark McDonnell, Lansdale, PA (US); James McNally, Souderton, PA (US)

(73) Assignee: Janssen Pharmaceutica NV (BG)

( * ) Notice: Subject to any disclaimer, the term of this patent is extended or adjusted under 35 U.S.C. 154(b) by 0 days.

This patent is subject to a terminal disclaimer.

(21) Appl. No.: 11/195,231

(22) Filed: Aug. 2, 2005

(65) Prior Publication Data

US 2006/0030585 A1 Feb. 9, 2006

Related U.S. Application Data

(60) Provisional application No. 60/599,131, filed on Aug. 5, 2004.

(51) Int. Cl.
*A61K 31/46* (2006.01)

(52) U.S. Cl. ................................ 514/304; 546/126

(58) Field of Classification Search ............... 546/126; 514/304

See application file for complete search history.

(56) References Cited

U.S. PATENT DOCUMENTS

| | | | |
|---|---|---|---|
| 2,368,006 | A | 1/1945 | Cusic |
| 2,784,185 | A | 3/1957 | Schuler |
| 2,901,478 | A | 8/1959 | Schuler |
| 3,179,665 | A | 4/1965 | Schmutz |
| 3,305,547 | A | 2/1967 | Stach et al. |
| 3,470,188 | A | 9/1969 | Kaiser et al. |
| 3,557,287 | A | 1/1971 | Berde et al. |
| 3,931,232 | A | 1/1976 | Bender et al. |
| 3,987,042 | A | 10/1976 | Gueremy et al. |
| 4,086,350 | A | 4/1978 | Zirkle |
| 4,275,209 | A | 6/1981 | Lassen et al. |
| 4,356,184 | A | 10/1982 | Deason et al. |
| 4,666,907 | A | 5/1987 | Fortin et al. |
| 4,777,177 | A | 10/1988 | Traber et al. |
| 5,502,049 | A | 3/1996 | Garret et al. |
| 6,004,983 | A | 12/1999 | Andersen et al. |
| 6,114,354 | A | 9/2000 | Andersen et al. |
| 6,153,626 | A | 11/2000 | Pelcman et al. |
| 7,060,711 | B2 | 6/2006 | Lubbert et al. |
| 2003/0018447 | A1 | 1/2003 | Florschuetz |
| 2003/0166672 | A1 | 9/2003 | Lubbert et al. |
| 2005/0009860 | A1* | 1/2005 | Carson et al. ............... 514/297 |
| 2006/0030585 | A1 | 2/2006 | Dax et al. |
| 2006/0135522 | A1 | 6/2006 | Carson et al. |
| 2006/0135524 | A1* | 6/2006 | Carson et al. .......... 514/252.04 |
| 2006/0135763 | A1 | 6/2006 | Coats et al. |
| 2006/0148823 | A1 | 7/2006 | Coats et al. |
| 2006/0287297 | A1* | 12/2006 | DeCorte et al. ............. 514/216 |

FOREIGN PATENT DOCUMENTS

| | | |
|---|---|---|
| DE | 2009555 | 10/1970 |
| EP | 0005607 B1 | 11/1979 |
| EP | 1049676 B1 | 11/2000 |
| EP | 1306376 A1 | 5/2003 |
| EP | 1321169 A1 | 6/2003 |
| FR | 2290202 A1 | 6/1976 |
| GB | 1128734 | 7/1966 |
| WO | WO 98/28275 A1 | 7/1998 |
| WO | WO 9900376 A1 | 1/1999 |
| WO | WO 0146191 A1 | 6/2001 |
| WO | WO 01/66543 A2 | 9/2001 |
| WO | WO 0172303 A1 | 10/2001 |
| WO | WO 0236573 A2 | 5/2002 |
| WO | WO 0248122 A2 | 6/2002 |
| WO | WO 03/035646 A2 | 5/2003 |
| WO | WO 2004026030 A2 | 4/2004 |
| WO | WO 2004035541 A1 | 4/2004 |
| WO | WO 2004092165 A1 | 10/2004 |
| WO | WO 2005/003131 A1 | 1/2005 |

OTHER PUBLICATIONS

Loughhead, David G. Tetrahedron Letters 1988, 5701-5702.*
Frontier Scientific Catalog Logan, Utah online "http://www.frontiersci.com/browse.php?browse=Boronic%20acid" Apr. 28, 2007.*
Zhang, et. al. Journal of Medicinal Chemistry 1999, 42, 5455-5463.*
Tao et. al. Bioorganic & Medicinal Chemistry Letters 2006 16, 938-942.*
Calo et. al. British Journal of Pharmacology 2002, 136, 303-311.*
Chang et. al. Molecular Pharmacology, 1984, 26, 484-488.*
Erchegyi et. al. Journal of Medicinal Chemistry 2003, 46, 5587-5596.*

(Continued)

*Primary Examiner*—Rita J Desai
*Assistant Examiner*—David K O'Dell

(57) ABSTRACT

Disclosed are compounds, compositions and methods for treating various diseases and conditions, including pain. Such compounds are represented by Formula I as follows:

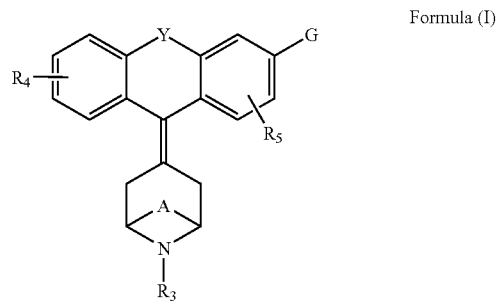

Formula (I)

wherein A, G, Y, $R_3$, $R_4$, and $R_5$ are defined herein.

24 Claims, No Drawings

OTHER PUBLICATIONS

Kruzsynski et. al. Journal of Peptide Research 2005, 66, 125-131.*
Pozharskii et. al. Heterocycles in Life and Society Wiley, 1997, pp. 1-6.*
Dorwald F. A. Side Reactions in Organic Synthesis, 2005, Wiley: VCH, Weinheim p. IX of Preface.*
Biemans et. al. Journal of Organic Chemistry 1996, 61, 9012-9015.*
West, Anthony R., Solid State Chemistry and its Applications, Wiley, New York, 1988, pp. 358 & 365.*
S. N. Calderona, et. al. "SNC 80 and Related Opioid Agonists" Current Pharmaceutical Design, 2004, 10, 733-742.*
PCT International Search Report dated Apr. 19, 2006 for PCT Application No. PCT/US2005/027568 which relates to U.S. Appl. No. 11/195,231.
Kraiser, C. et al., "Analogs of Phenothiazines. 5. Synthsis and Neuropharmacological Activity of Some Piperidylidene Derivatives of Thioxanthenes, Xanthenes, Dibenzoxepins, and Acridans." J. Med. Chem., 1974, pp. 57-61, vol. 17, No. 1.
Ananthan, S.: The AAPS Journal 2006, 8(1): E118-E125.
Berge, S.M. et al.: Pharmaceutical Salts; J. of Pharmaceutical Sciences (1977) 66(1): 1-19.
Bidlack, J.M. et al.: 8-Carboxamidocyclazocine: A Long-Acting, Novel Benzomorphan; The J. of Pharm. & Exper. Therapeutics (2002) 302(1): 374-380.
Boyd, R.E. et al.: Synthesis and Binding Affinities of 4-Diarylaminotropanes, a New Class of Delta Opioid Agonists; Bioorg. & Med. Chem. Letters (2000) 10: 1109-1111.
Commercial 2-Bromo-Phenols from Sigma-Aldrich.
Commercial 4-piperidinones.
Connor, M. et al.: Opioid Receptor Signalling Mechanisms; Clinical and Exper. Pharmacology and Physiology (1999) 26: 493-499.
Dorwald, F.Z.: Side Reactions in Organic Synthesis (2005) Wiley: VCH, Weinheim p. 1X of Preface: 1-15.
Dörwald, F.Z.: Side Reactions in Organic Synthesis (2005) Wiley: VCH, Weinheim p. 1X of Preface & Chapter 8: 279-308.
Frontier Scientific Catalog (Logan, UT) Advanced Discovery Chemicals Pure (*and not so*) Simple 2006; Discover Chemicals A-F, H-I, M-N, P-Q and T.
Gilbert, P.E. et al.: The Effects of Morphine- and Nalorphine-Like Drugs in the Nondependent, Morphine-Dependent and Cyclazocine-Dependent Chronic Spinal Dog; The J. of Pharm. And Exp. Thera. (1976) 198(1): 66-82.
Gould, P.L.: Salt selection for basic drugs; Intl J. of Pharmaceutics (1986) 33: 201-217.
Gribble, G.W. et al.: Sodium Triacetoxyborohydride[1]; Encyclopedia of Reagents for Organic Synthesis online @http://www.mrw.interscience.wiley.com/eros/articles/rs112/sect0.html Apr. 24, 2007.
Gross, R.A. et al.: Dynorphin A and cAMP-dependent protein kinase independently regulate neuronal calcium currents; Proc. Natl. Acad. Sci. (1990) 87: 7025-7029.
Hancock, B.C. et al.: Characteristics and Significance of the Amorphous State in Pharmaceutical Systems; J. of Pharm. Sciences (1997) 86(1): 1-12.
Hutchins, R.O. et al.: Selective Reductive Displacement of Alkyl Halides and Sulfonate Esters with Cyanoborohydride Reagents in Hexamethylphosphoramide; J. Org. Chem. (1977) 42(1): 82-91.
Kenakin, T. et al.: The ligand paradox between affinity and efficacy: can you be there and not make a difference?; Trends in Pharm. Sciences (2002) 23(6): 275-280.
Le Bars, D. et al.: Animal Models of Nociception; Pharmacological Reviews (2001) 53: 597-652.
Lord, John A.H. et al.: Endogenous opioid peptides: multiple agonists and receptors; Nature (1977) 267: 495-499.
Mansour, A. et al.: Anatomy of CNS opioid receptors; Trends in Neuroscience (1988) 11(7): 308-314.
Nieschulz, O. et al.: "Pharmacological studies on 10-(1-methyl-3-piperidyl)-2 methoxyphenothiazine and related compounds"; Arzneimittel-Forschung 1960, 10, 156-165.
Pert, C.B. et al.: Opiate Receptor: Demonstration in Nervous Tissue; Science (1973) 179: 1011-1014.

Quock, R.M. et al.: The δ-Opioid Receptor: Molecular Pharmacology, Signal Transduction, and the Determination of Drug Efficacy; Pharmacological Reviews (1999) 51(3): 503-532.
Sharma, S.K. et al.: Dual regulation of adenylate cyclase accounts for narcotic dependence and tolerance; Proc. Natl. Acad. Sci. (1975) 72(8): 3092-3096.
Still, W. Clark et al.: Rapid Chromatographic Technique for Preparative Separations with Moderate Resolution; J. Org. Chem. (1978) 43(14): 2923-2925.
Structures in copending U.S. Appl. No. 11/195,231.
Sun, X. et al.: Synthesis and Opioid Receptor Binding Properties of Conformation-Rigidified Analogues of 8-Carboxamidocyclazocine and 8-Formamidocyclazocine; Abstract of Papers 229th ACS Natl Meeting NY 2005.
Thomas, J.B. et al.: 4-[(8-Alkyl-8-azabicyclo[3.2.1]octyl-3-yl)-3-arylanilino]-*N,N*-diethylbenzamides: High Affinity, Selective Ligands for the Delta Opioid Receptor Illustrate Factors Important to Antagonist Activity; Bioorg. & Med. Chem. Letters (2000) 10(11): 1281-1284.
Thomas, J.B. et al.: (±)-4-[(N-Allyl-*CIS*-3-Methyl-4-Piperidinyl)Phenylamino]-*N,N*-Diethylbenzamide Displays Selective Binding for the Delta Opioid Receptor; Bioorg. & Med. Chem. Letters (1999) 9(20): 3053-3056.
Thomas, J.B. et al.: Factors Influencing Agonist Potency and Selectivity for the Opioid δ Receptor Are Revealed in Structure—Activity Relationship Studies of the 4-[(*N*-Substituted-4-piperidinyl)arylamino]-*N,N*-diethylbenzamides; J. Med. Chem. (2001) 44(6): 972-987.
Truce, W. E. et al.: The Smiles and Related Rearrangements of Aromatic Systems; Organic Reactions (1970) 18: 99-215.
Van Alstine, M.A. et al.: Synthesis and evaluation of novel N-substituted derivatives of 8-carboxamidocyclazocine; Abstract of Papers 231st ACS National Meeting, Atlanta, GA 2006, MEDI-009.
Walpole, C.S.J. et al.: The Discovery of Capsazepine, the First Competitive Antagonist of the Sensory Neuron Excitants Capsaicin and Resiniferatoxin; J. Med. Chem. (1994) 37: 1942-1954.
Wentland, M.P. et al.: 8-Aminocyclazocine Analogues: Synthesis and Structure—Activity Relationships[†]; Bioorg. & Med. Chem. Letters (2000) 10(2): 183-187.
Wentland, M.P. et al.: Selective Protection and Functionalization of Morphine: Synthesis and Opioid Receptor Binding Properties of 3-Amino-3-desoxymorphine Derivatives[†,1]; J. Med. Chem. (2000) 43(19): 3558-3565.
Wentland, M.P. et al.: 3-Carboxamido Analogues of Morphine and Naltrexone: Synthesis and Opioid Receptor Binding Properties; Bioorg. & Med. Chem. Letters (2001) 11: 1717-1721.
Wentland, M.P. et al.: 8-Carboxamidocyclazocine Analogues: Redefining the Structure—Activity Relationships of 2,6-Methano-3-benzazocines; Bioorg. & Med. Chem. Letters (2001) 11: 623-626.
Wentland, M.P. et al.: Syntheses and Opioid Receptor Binding Affinities of 8-Amino-2,6-methano-3-benzazocines; J. Med. Chem. (2003) 46: 838-849.
Wentland, M.P. et al.: Redefining the Structure—Activity Relationships of 2,6-Methano-3-benzazocines. Part 2: 8-Formamidocyclazocine Analogues; Bioorg. & Med. Chem. Letters (2003) 13: 1911-1914.
Wentland, M.P. et al.: Thioformamido and Thiocarboxamido Derivatives of Cyclazocine: Syntheses and Opioid Receptor Binding Properties; Abstract of Papers 226th ACS Natl. Meeting NY 2003.
Wentland, M.P. et al.: Redefining the structure—activity relationships of 2,6-methano-3-benzazocines. Part 3: 8-Thiocarboxamido and 8-thioformamido derivatives of cyclazocine; Bioorg. & Med. Chem. Letters (2005) 15: 2547-2551.
Wentland, M.P. et al.: Synthesis and opioid receptor binding properties of a highly potent 4-hydroxy analogue of naltrexone; Bioorg. & Med. Chem. Letters (2005) 15: 2107-2110.
Wollemann, M.: Recent Developments in the Research of Opioid Receptor Subtype Molecular Characterization; J. of Neurochemistry (1990) 54(4): 1095-1101.

Zhang, A. et al.: 10-Ketomorphinan and 3-Substituted-3-desoxymorphinan Analogues as Mixed κ and μ Opioid Ligands: Synthesis and Biological Evaluation of Their Binding Affinity at Opioid Receptors; J. Med. Chem. (2004) 47(1):165-174.

Carson, J.R. et al.: N-Alkyl-4-[(8-azabicyclo[3.2.1]-oct-3-ylidene)phenylmethyl]-benzamides, μ and δ opioid agonists: a μ address; Bioorganic & Med. Chem. Letters (2004) 14: 2113-2116.

Furness, M.S. et al.: Probes for Narcotic Receptor-Mediated Phenomena. 27.[1] Synthesis and Pharmacological Evaluation of Selective δ-Opioid Receptor Agonists from 4-[αR)-α-(2S,5R)-4-Substituted-2,5-dimethyl-1-piperazinyl-3-methoxybenzyl]-N,N-diethylbenzamides and Their Enantiomers; J. Med. Chem. (2000) 43: 3193-3196.

Jones, M. Jr.: Organic Chemistry Norton, New York (1997): 578-591.

* cited by examiner

TRICYCLIC-BRIDGED PIPERIDINYLIDENE DERIVATIVES AS δ-OPIOID MODULATORS

CROSS-REFERENCE TO RELATED APPLICATIONS

This Application claims priority to U.S. Provisional Patent Application No. 60/599,131, filed Aug. 5, 2004, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (1993); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

D. Delorme, E. Roberts and Z. Wei, World Patent WO/28275 (1998) discloses diaryl methylidenylpiperidines that are opioid analgesics, but does not disclose or suggest the compounds of the present invention.

C. Kaiser, and others (J. Med. Chem. 1974, Volume 17, pages 57-61) disclose some piperidylidene derivatives of thioxanthenes, xanthenes, dibenoxepins and acridans that are neuroleptic agents. These authors, however, do not disclose or suggest either the structure or the activity of the compounds of the present invention.

British Patent GB 1128734 (1966) discloses derivatives of 6,11-dihydrodibenzo[b,e]oxepine that are anticholinergic, anti-convulsive, muscle-relaxing, sedating, diuretic, and/or vasoactive agents. These, agents, however, differ significantly from the compounds of the present invention both structurally and pharmacologically.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

SUMMARY OF THE INVENTION

The present invention is directed to compositions comprising a compound of Formula (I):

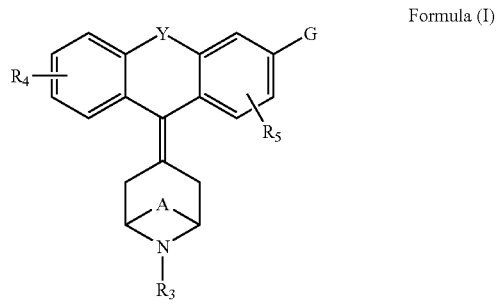

Formula (I)

wherein:
G is —C(Z)NR$_1$R$_2$, C$_{6-10}$aryl, C$_{6-10}$arylthio, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein the $C_{6-10}$aryl group in the $C_{6-10}$aryl-containing substituents of G, and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

$R_1$ is a substituent selected from the group consisting of hydrogen, $C_{1-8}$alkanyl, $C_{2-8}$alkenyl, and $C_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{3-8}$cycloalkanyl; provided that when Z is O or S, $R_2$ is other than hydrogen or unsubstituted $C_{1-8}$alkanyl; and, wherein $C_{1-8}$alkanyl of $R_2$ is optionally substituted with one to three substituents independently selected from the group consisting of phenyl, amino, $C_{1-6}$alkanylamino, di($C_{1-6}$alkanyl)amino, $C_{1-6}$alkanyloxy, $C_{1-6}$alkanylthio, hydroxy, fluoro, chloro, cyano, aminocarbonyl, $C_{1-8}$alkanylaminocarbonyl, di($C_{1-8}$alkanyl)aminocarbonyl, $C_{1-8}$alkanyloxycarbonyl, and aryloxy; wherein the phenyl and aryloxy substituents of $C_{1-8}$alkanyl are optionally further substituted with, and the $C_{6-10}$aryl and $C_{3-8}$cycloalkanyl substituents of $R_2$ are optionally substituted with, one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with phenyl (wherein phenyl is optionally substituted with one to three $C_{1-4}$alkanyl or $C_{1-4}$alkanyloxy substituents) and one to two additional substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

or, $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —($CH_2$)$_{3-5}$—, —O($CH_2$)$_{2-4}$—, —($CH_2$)$_{2-4}$O—, and —O($CH_2$)$_{1-3}$O—;

$R_4$ is one to three substituents independently selected from the group consisting of hydrogen, $C_{1-6}$alkanyl, $C_{2-6}$alkenyl, $C_{2-6}$alkynyl, aryl($C_{2-6}$)alkynyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, aminocarbonyl, $C_{1-6}$alkanylaminocarbonyl, di($C_{1-6}$alkanyl)aminocarbonyl, $C_{1-6}$alkanylcarbonylamino, $C_{1-6}$alkanylthio, $C_{1-6}$alkanylsulfonyl, halogen, hydroxy, mercapto, aminothiocarbonyl, amidino, hydroxyamidino, phenylcarbonyl, —C(=NOH)phenyl, aminomethyl, hydroxymethyl, methanesulfonylamino, $C_{6-10}$arylamino (wherein $C_{6-10}$aryl is optionally substituted with one to three substituents independently selected from the group consisting of $C_{1-6}$alkanyl, $C_{1-6}$alkoxy, halogen, and hydroxy), dihydroimidazolyl, formylamino, thioformylamino, pyridinylamino, cyano, hydroxycarbonyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thienyl, fluoroalkanyl and fluoroalkanyloxy; or optionally, when $R_4$ is two substituents attached to adjacent carbon atoms, the two substituents together form a single fused moiety; wherein the fused moiety is selected from the group consisting of —($CH_2$)$_{3-5}$—, —O($CH_2$)$_{2-4}$—, —($CH_2$)$_{2-4}$O—, —O($CH_2$)$_{1-3}$O— and —S—C($NH_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is absent or —($CH_2$)$_m$—, wherein m is 2 or 3;

Y is —($CH_2$)$_n$X— or —X($CH_2$)$_n$—;

X is O or S n is 0 or 1;

Z is O, S, NH, N($C_{1-6}$alkanyl), N(OH), N(O$C_{1-6}$alkanyl), or N(phenyl);

and enantiomers, diastereomers, tautomers, solvates, or pharmaceutically acceptable salts thereof.

The present invention is also directed to compositions comprising a compound of Formula (Ib):

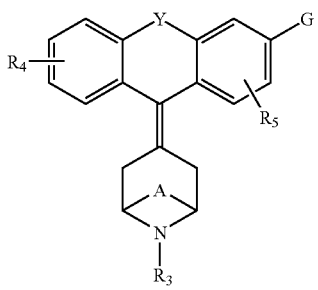

Formula (Ib)

wherein:
G is bromo, chloro, cyano, trifluoromethanesulfonyloxy, $C_{1-8}$alkanyloxycarbonyl, carboxy, —C(Z)NR$_1$R$_2$, $C_{6-10}$aryl, $C_{6-10}$arylthio, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein the $C_{6-10}$aryl group in the $C_{6-10}$aryl-containing substituents of G and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

R$_1$ is a substituent selected from the group consisting of hydrogen, $C_{1-8}$alkanyl, $C_{2-8}$alkenyl, and $C_{2-8}$alkynyl;

R$_2$ is a substituent selected from the group consisting of hydrogen; $C_{1-8}$alkanyl; $C_{2-8}$alkenyl; $C_{2-8}$alkynyl; $C_{6-10}$aryl; and $C_{3-8}$cycloalkanyl; provided that when Z is O or S, R$_2$ is other than hydrogen or unsubstituted $C_{1-8}$alkanyl; and, wherein $C_{1-8}$alkanyl of R$_2$ is optionally substituted with one to three substituents independently selected from the group consisting of phenyl, amino, $C_{1-6}$alkanylamino, di($C_{1-6}$alkanyl)amino, $C_{1-6}$alkanyloxy, $C_{1-6}$alkanylthio, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; wherein the phenyl and aryloxy substituents of $C_{1-8}$alkanyl are optionally further substituted with, and the $C_{6-10}$aryl and $C_{3-8}$cycloalkanyl substituents of R$_2$ are optionally substituted with, one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or R$_1$ and R$_2$ taken together with the nitrogen to which they are attached form a 5-7 membered cycloheteroalkyl optionally substituted with phenyl (wherein phenyl is optionally substituted with one to three $C_{1-4}$alkanyl or $C_{1-4}$alkanyloxy substituents) and one to two additional substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

or, R$_1$ and R$_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

R$_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl ($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

R$_4$ is one to three substituents independently selected from the group consisting of hydrogen, $C_{1-6}$alkanyl, $C_{2-6}$alkenyl, $C_{2-6}$alkynyl, aryl($C_{2-6}$)alkynyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, aminocarbonyl, $C_{1-6}$alkanylaminocarbonyl, di($C_{1-6}$alkanyl)aminocarbonyl, $C_{1-6}$alkanylcarbonylamino, $C_{1-6}$alkanylthio, $C_{1-6}$alkanylsulfonyl, halogen, hydroxy, mercapto, aminothiocarbonyl, amidino, hydroxyamidino, phenylcarbonyl, —C(=NOH)phenyl, aminomethyl, hydroxymethyl, methanesulfonylamino, $C_{6-10}$arylamino (wherein $C_{6-10}$aryl is optionally substituted with one to three substituents independently selected from the group consisting of $C_{1-6}$alkanyl, $C_{1-6}$alkoxy, halogen, and hydroxy), dihydroimidazolyl, formylamino, thioformylamino, pyridinylamino, cyano, hydroxycarbonyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thienyl, fluoroalkanyl and fluoroalkanyloxy; or optionally, when R$_4$ is two substituents attached to adjacent carbon atoms, the two substituents together form a single fused moiety; wherein the fused moiety is selected from the group consisting of —(CH$_2$)$_{3-5}$—, —O(CH$_2$)$_{2-4}$—, —(CH$_2$)$_{2-4}$O—, —O(CH$_2$)$_{1-3}$O— and —S—C(NH$_2$)=N—;

R$_5$ is one to two substituents independently selected from the group consisting of hydrogen, C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanyloxycarbonyl, C$_{1-6}$alkanylaminocarbonyl, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl and fluoro(C$_{1-6}$)alkanyloxy;

A is absent or —(CH$_2$)$_m$—, wherein m is 2 or 3;

Y is —(CH$_2$)$_n$X— or —X(CH$_2$)$_n$—;

X is O or S n is 0 or 1;

Z is O, S, NH, N(C$_{1-6}$alkanyl), N(OH), N(OC$_{1-6}$alkanyl), or N(phenyl);

and enantiomers, diastereomers, tautomers, solvates, or pharmaceutically acceptable salts thereof.

Finally, the present invention is directed to veterinary and pharmaceutical compositions containing compounds of Formula (I) and Formula (Ib) wherein the compositions are used to treat mild to severe pain in warm-blooded animals.

DETAILED DESCRIPTION OF THE INVENTION

As used herein, the following underlined terms are intended to have the following meanings:

"C$_{a-b}$" (where a and b are integers) refers to a radical containing from a to b carbon atoms inclusive. For example, C$_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are (C$_1$-C$_6$) alkyl, with (C$_1$-C$_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are (C$_{1-8}$) alkanyl, with (C$_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and "Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or (C$_1$-C$_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C$_{5-20}$) aryl, with (C$_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is $(C_{6-26})$ arylalkyl, e.g., the alkanyl, alkenyl or alkynyl moiety of the arylalkyl group is $(C_{1-6})$ and the aryl moiety is $(C_{5-20})$. In particularly preferred embodiments the arylalkyl group is $(C_{6-13})$, e.g., the alkanyl, alkenyl or alkynyl moiety of the arylalkyl. group is $(C_{1-3})$ and the aryl moiety is $(C_{5-10})$. Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy ($CH_3CH_2CH_2O$—), propan-2-yloxy (($CH_3)_2CHO$—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are $(C_{1-8})$ alkanyloxy groups, with $(C_{1-3})$ being particularly preferred.

"Parent Heteroaromatic Ring System:" refers to a parent aromatic ring system in which one carbon atom is replaced with a heteroatom. Heteroatoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O$^-$, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, ($C_{1-8}$alkylamino)carbonyl, (arylamino)carbonyl and aryl($C_{1-8}$alkyl)carbonyl.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

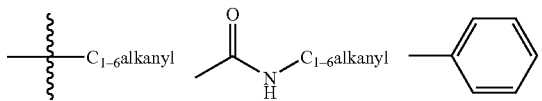

An embodiment of the present invention is directed to a compound of Formula (I) and Formula (Ib) wherein the structure is numbered as defined herein.

Formula (I) and Formula (Ib)

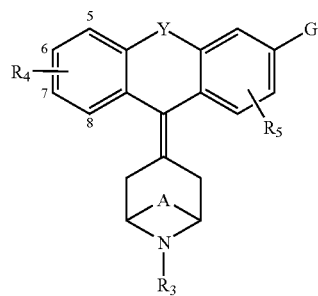

The present invention is directed to analgesic and antipyretic uses of compositions comprising a compound of Formula (I):

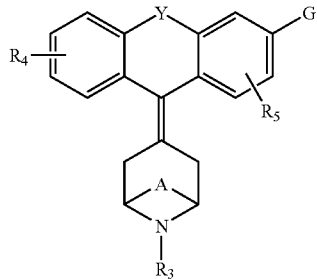

Formula (I)

wherein:

G is —C(Z)NR$_1$R$_2$, C$_{6-10}$aryl, C$_{6-10}$arylthio, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein the C$_{6-10}$aryl group in the C$_{6-10}$aryl-containing substituents of G and the heterocycles of G are optionally substituted with one to three substituents independently selected from the group consisting of C$_{1-8}$alkanyl, C$_{2-8}$alkenyl, C$_{2-8}$alkynyl, C$_{1-8}$alkanyloxy, hydroxy(C$_{1-8}$)alkanyl, carboxy(C$_{1-8}$)alkanyl, C$_{1-8}$alkanylcarbonylamino, halogen, hydroxy, cyano, nitro, oxo, thioxo, amino, C$_{1-6}$alkanylamino, di(C$_{1-6}$alkanyl)amino, C$_{1-8}$alkanylthio, C$_{1-8}$alkanylsulfonyl, C$_{1-8}$alkanylsulfonylamino, aminocarbonyl, aminothiocarbonyl, aminocarbonylamino, aminothiocarbonylamino, C$_{1-8}$alkanylaminocarbonyl, di(C$_{1-8}$alkanyl)aminocarbonyl, and C$_{1-6}$alkanyloxycarbonylamino;

R$_1$ is a substituent selected from the group consisting of hydrogen, C$_{1-8}$alkanyl, C$_{2-8}$alkenyl, and C$_{2-8}$alkynyl;

R$_2$ is a substituent selected from the group consisting of hydrogen; C$_{1-8}$alkanyl; C$_{2-8}$alkenyl; C$_{2-8}$alkynyl; C$_{6-10}$aryl; and C$_{3-8}$cycloalkanyl; provided that when Z is O or S, R$_2$ is other than hydrogen or unsubstituted C$_{1-8}$alkanyl; and, wherein C$_{1-8}$alkanyl of R$_2$ is optionally substituted with one to three substituents independently selected from the group consisting of phenyl, amino, C$_{1-6}$alkanylamino, di(C$_{1-6}$alkanyl)amino, C$_{1-6}$alkanyloxy, C$_{1-6}$alkanylthio, hydroxy, fluoro, chloro, cyano, aminocarbonyl, C$_{1-8}$alkanylaminocarbonyl, di(C$_{1-8}$alkanyl)aminocarbonyl, C$_{1-6}$alkanyloxycarbonyl, and aryloxy; wherein the phenyl and aryloxy substituents of C$_{1-8}$alkanyl are optionally further substituted with, and the C$_{6-10}$aryl and C$_{3-8}$cycloalkanyl substituents of R$_2$ are optionally substituted with, one to three substituents independently selected from the group consisting of C$_{1-8}$alkanyl, C$_{2-8}$alkenyl, C$_{2-8}$alkynyl, C$_{1-8}$alkanyloxy, trifluoromethyl, trifluoromethoxy, phenyl, halogen, cyano, hydroxy, C$_{1-8}$alkanylthio, C$_{1-8}$alkanylsulfonyl, and C$_{1-8}$alkanylsulfonylamino;

or R$_1$ and R$_2$ taken together with the nitrogen to which they are attached form a 5-7 membered cycloheteroalkyl optionally substituted with phenyl (wherein phenyl is optionally substituted with one to three C$_{1-4}$alkanyl or C$_{1-4}$alkanyloxy substituents) and one to two additional substituents independently selected from the group consisting of C$_{1-8}$alkanyl, hydroxy(C$_{1-8}$)alkanyl, hydroxy, amino, C$_{1-6}$alkanylamino, di(C$_{1-6}$alkanyl)amino, and halogen;

or, R$_1$ and R$_2$ taken together with the nitrogen to which they are attached form a 5-7 membered cycloheteroalkyl optionally substituted with one to three substituents independently selected from the group consisting of C$_{1-8}$alkanyl, hydroxy(C$_{1-8}$)alkanyl, hydroxy, amino, C$_{1-6}$alkanylamino, di(C$_{1-6}$alkanyl)amino, and halogen;

R$_3$ is a substituent selected from the group consisting of hydrogen, C$_{1-8}$alkanyl, halo$_{1-3}$(C$_{1-8}$)alkanyl, C$_{2-8}$alkenyl, C$_{2-8}$alkynyl, C$_{3-8}$cycloalkanyl, cycloalkanyl(C$_{1-8}$)alkanyl, C$_{1-8}$alkanyloxy(C$_{1-8}$)alkanyl, C$_{1-8}$alkanylthio(C$_{1-8}$)alkanyl, hydroxyC$_{1-8}$alkanyl, C$_{1-8}$alkanyloxycarbonyl, halo$_{1-3}$(C$_{1-8}$)alkanylcarbonyl, formyl, thioformyl, carbamimidoyl, phenylimino(C$_{1-8}$)alkanyl, phenyl(C$_{1-8}$)alkanyl, phenyl(C$_{1-8}$)alkenyl, phenyl(C$_{1-8}$)alkynyl, naphthyl(C$_{1-8}$)alkanyl and heteroaryl(C$_{1-8}$)alkanyl wherein the heteroaryl is selected from the group consisting of benzo[1,3]dioxolyl, imidazolyl, furanyl, pyridinyl, thiophenyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl, thioureido, and fluoro(C$_{1-6}$)alkanyloxy; alternatively, when phenyl and heteroaryl are optionally substituted with alkanyl or alkanloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

R$_4$ is one to three substituents independently selected from the group consisting of hydrogen, C$_{1-6}$alkanyl, C$_{2-6}$alkenyl, C$_{2-6}$alkynyl, aryl(C$_{2-6}$)alkynyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanyloxycarbonyl, aminocarbonyl, C$_{1-6}$alkanylaminocarbonyl, di(C$_{1-6}$alkanyl)aminocarbonyl, C$_{1-6}$alkanylcarbonylamino, C$_{1-6}$alkanylthio, C$_{1-6}$alkanylsulfonyl, halogen, hydroxy, mercapto, aminothiocarbonyl, amidino, hydroxyamidino, phenylcarbonyl, —C(=NOH)phenyl, aminomethyl, hydroxymethyl, methanesulfonylamino, C$_{6-10}$arylamino (wherein C$_{6-10}$aryl is optionally substituted with one to three substitutents independently selected from the group consisting of C$_{1-6}$alkanyl, C$_{1-6}$alkoxy, halogen, and hydroxy), dihydroimidazolyl, formylamino, thioformylamino, pyridinylamino, cyano, hydroxycarbonyl, C$_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thienyl, fluoroalkanyl and fluoroalkanyloxy; or optionally, when R$_4$ is two substituents attached to adjacent carbon atoms, the two substituents together form a single fused moiety; wherein the fused moiety is selected from the group consisting of —(CH$_2$)$_{3-5}$—, —O(CH$_2$)$_{2-4}$—, —(CH$_2$)$_{2-4}$O—, —O(CH$_2$)$_{1-3}$O— and —S—C(NH$_2$)=N—;

R$_5$ is one to two substituents independently selected from the group consisting of hydrogen, C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanyloxycarbonyl, C$_{1-6}$alkanylaminocarbonyl, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl and fluoro(C$_{1-6}$)alkanyloxy;

A is absent or —(CH$_2$)$_m$—, wherein m is 2 or 3;

Y is —(CH$_2$)$_n$X— or —X(CH$_2$)$_n$—;

X is O or S n is 0 or 1;

Z is O, S, NH, N(C$_{1-6}$alkanyl), N(OH), N(OC$_{1-6}$alkanyl), or N(phenyl);

and enantiomers, diastereomers, tautomers, solvates, or pharmaceutically acceptable salts thereof.

The present invention is also directed to analgesic and anti-pyretic uses of compositions comprising a compound of Formula (Ib):

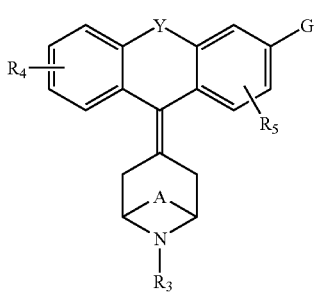

Formula (Ib)

wherein:

G is bromo, chloro, cyano, trifluoromethanesulfonyloxy, C$_{1-8}$alkanyloxycarbonyl, carboxy, —C(Z)NR$_1$R$_2$, C$_{6-10}$aryl, C$_{6-10}$arylthio, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein the C$_{6-10}$aryl group in the C$_{6-10}$aryl-containing substituents of G and the heterocycles of G are optionally substituted with one to three substituents independently selected from the group consisting of C$_{1-8}$alkanyl, C$_{2-8}$alkenyl, C$_{2-8}$alkynyl, C$_{1-8}$alkanyloxy, hydroxy(C$_{1-8}$)alkanyl, carboxy(C$_{1-8}$)alkanyl, C$_{1-8}$alkanylcarbonylamino, halogen, hydroxy, cyano, nitro, oxo, thioxo, amino, C$_{1-6}$alkanylamino, di(C$_{1-6}$alkanyl)amino, C$_{1-8}$alkanylthio, C$_{1-8}$alkanylsulfonyl, C$_{1-8}$alkanylsulfonylamino, aminocarbonyl, aminothiocarbonyl, aminocarbonylamino, aminothiocarbonylamino, C$_{1-8}$alkanylaminocarbonyl, di(C$_{1-8}$alkanyl)aminocarbonyl, and C$_{1-6}$alkanyloxycarbonylamino;

R$_1$ is a substituent selected from the group consisting of hydrogen, C$_{1-8}$alkanyl, C$_{2-8}$alkenyl, and C$_{2-8}$alkynyl;

R$_2$ is a substituent selected from the group consisting of hydrogen; C$_{1-8}$alkanyl; C$_{2-8}$alkenyl; C$_{2-8}$alkynyl; C$_{6-10}$aryl; and C$_{3-8}$cycloalkanyl; provided that when Z is O or S, R$_2$ is other than hydrogen or unsubstituted C$_{1-8}$alkanyl; and, wherein C$_{1-8}$alkanyl of R$_2$ is optionally substituted with one to three substituents independently selected from the group consisting of phenyl, amino, C$_{1-6}$alkanylamino, di(C$_{1-6}$alkanyl)amino, C$_{1-6}$alkanyloxy, C$_{1-6}$alkanylthio, hydroxy, fluoro, chloro, cyano, aminocarbonyl, C$_{1-8}$alkanylaminocarbonyl, di(C$_{1-8}$alkanyl)aminocarbonyl, C$_{1-8}$alkanyloxycarbonyl, and aryloxy; wherein the phenyl and aryloxy substituents of C$_{1-8}$alkanyl are optionally further substituted with, and the C$_{6-10}$aryl and C$_{3-8}$cycloalkanyl substituents of R$_2$ are optionally substituted with, one to three substituents independently selected from the group consisting of C$_{1-8}$alkanyl, C$_{2-8}$alkenyl, C$_{2-8}$alkynyl, C$_{1-8}$alkanyloxy, trifluoromethyl, trifluoromethoxy, phenyl, halogen, cyano, hydroxy, C$_{1-8}$alkanylthio, C$_{1-8}$alkanylsulfonyl, and C$_{1-8}$alkanylsulfonylamino;

or R$_1$ and R$_2$ taken together with the nitrogen to which they are attached form a 5-7 membered cycloheteroalkyl optionally substituted with phenyl (wherein phenyl is optionally substituted with one to three C$_{1-4}$alkanyl or C$_{1-4}$alkanyloxy substituents) and one to two additional substituents independently selected from the group consisting of C$_{1-8}$alkanyl, hydroxy(C$_{1-8}$)alkanyl, hydroxy, amino, C$_{1-6}$alkanylamino, di(C$_{1-6}$alkanyl)amino, and halogen;

or, R$_1$ and R$_2$ taken together with the nitrogen to which they are attached form a 5-7 membered cycloheteroalkyl optionally substituted with one to three substituents independently selected from the group consisting of C$_{1-8}$alkanyl, hydroxy(C$_{1-8}$)alkanyl, hydroxy, amino, C$_{1-6}$alkanylamino, di(C$_{1-6}$alkanyl)amino, and halogen;

R$_3$ is a substituent selected from the group consisting of hydrogen, C$_{1-8}$alkanyl, halo$_{1-3}$(C$_{1-8}$)alkanyl, C$_{2-8}$alkenyl, C$_{2-8}$alkynyl, C$_{3-8}$cycloalkanyl, cycloalkanyl(C$_{1-8}$)alkanyl, C$_{1-8}$alkanyloxy(C$_{1-8}$)alkanyl, C$_{1-8}$alkanylthio(C$_{1-8}$)alkanyl, hydroxyC$_{1-8}$alkanyl, C$_{1-8}$alkanyloxycarbonyl, halo$_{1-3}$(C$_{1-8}$)alkanylcarbonyl, formyl, thioformyl, carbamimidoyl, phenylimino(C$_{1-8}$)alkanyl, phenyl(C$_{1-8}$)alkanyl, phenyl(C$_{1-8}$)alkenyl, phenyl(C$_{1-8}$)alkynyl, naphthyl(C$_{1-8}$)alkanyl and heteroaryl (C$_{1-8}$)alkanyl wherein the heteroaryl is selected from the group consisting of benzo[1,3]dioxolyl, imidazolyl, furanyl, pyridinyl, thiophenyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl, thioureido, and fluoro(C$_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

R$_4$ is one to three substituents independently selected from the group consisting of hydrogen, C$_{1-6}$alkanyl, C$_{2-6}$alkenyl, C$_{2-6}$alkynyl, aryl(C$_{2-6}$)alkynyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanyloxycarbonyl, aminocarbonyl, C$_{1-6}$alkanylaminocarbonyl, di($C_{1-6}$alkanyl)aminocarbonyl, $C_{1-6}$alkanylcarbonylamino, $C_{1-6}$alkanylthio, $C_{1-6}$alkanylsulfonyl, halogen, hydroxy, mercapto, aminothiocarbonyl, amidino, hydroxyamidino, phenylcarbonyl, —C(=NOH)phenyl, aminomethyl, hydroxymethyl, methanesulfonylamino, $C_{6-10}$arylamino (wherein $C_{6-10}$aryl is optionally substituted with one to three substituents independently selected from the group consisting of $C_{1-6}$alkanyl, $C_{1-6}$alkoxy, halogen, and hydroxy), dihydroimidazolyl, formylamino, thioformylamino, pyridinylamino, cyano, hydroxycarbonyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thienyl, fluoroalkanyl and fluoroalkanyloxy; or optionally, when $R_4$ is two substituents attached to adjacent carbon atoms, the two substituents together form a single fused moiety; wherein the fused moiety is selected from the group consisting of —$(CH_2)_{3-5}$—, —$O(CH_2)_{2-4}$—, —$(CH_2)_{2-4}O$—, —$O(CH_2)_{1-3}O$— and —S—C($NH_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is absent or —$(CH_2)_m$—, wherein m is 2 or 3;

Y is —$(CH_2)_n$X— or —X$(CH_2)_n$—;

X is O or S n is 0 or 1;

Z is O, S, NH, N($C_{1-6}$alkanyl), N(OH), N(O$C_{1-6}$alkanyl), or N(phenyl);

and enantiomers, diastereomers, tautomers, solvates, or pharmaceutically acceptable salts thereof.

Embodiments of the present invention include compounds of Formula (I) wherein, preferably:

a) G is —C(Z)$NR_1R_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, isothiazolyl, isoxazolyl, oxazolyl, isoxadiazolyl, quinolinyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

b) G is —C(Z)$NR_1R_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, furyl, isothiazolyl, isoxazolyl, oxazolyl, isoxadiazolyl, quinolinyl, and pyridinyl; wherein phenyl and the heterocycles of G are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl;

c) G is —C(Z)$NR_1R_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, quinolinyl, and pyridinyl; wherein phenyl and the heterocycles of G are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl;

d) $R_1$ is a substituent selected from the group consisting of hydrogen and $C_{1-4}$alkanyl;

e) $R_1$ is selected from the group consisting of hydrogen, methyl, ethyl, and propyl;

f) $R_1$ is selected from the group consisting of hydrogen, methyl, or ethyl;

g) $R_2$ is selected from the group consisting of hydrogen; $C_{1-4}$alkanyl; phenyl; and $C_{3-6}$cycloalkanyl; provided that when Z is O or S, $R_2$ is other than hydrogen or unsubstituted $C_{1-4}$alkanyl; and, wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; wherein the phenyl and phenoxy substituents of $C_{1-4}$alkanyl are optionally further substituted with, and the phenyl and $C_{3-6}$cycloalkanyl substituents of $R_2$ are optionally substituted with, one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with phenyl (wherein phenyl is optionally substituted with $C_{1-4}$alkanyloxy or hydroxy), $C_{1-4}$alkanyl, or hydroxy;

h) $R_2$ is selected from the group consisting of $C_{1-4}$alkanyl, phenyl, and $C_{3-6}$cycloalkanyl; provided that when Z is O or S, $R_2$ is other than unsubstituted $C_{1-4}$alkanyl; and, wherein $C_{1-4}$alkanyl is optionally substituted with one to three substituents independently selected from the group consisting of phenyl, $C_{1-4}$alkanyloxy, hydroxy, fluoro, aminocarbonyl, $C_{1-8}$alkanylaminocarbonyl, di($C_{1-8}$alkanyl)aminocarbonyl, and phenoxy; wherein the phenyl and phenoxy substituents of $C_{1-4}$alkanyl are optionally further substituted with, and the phenyl of $R_2$ is optionally substituted with, one to three substituents independently selected from the group consisting of $C_{1-6}$alkanyl, $C_{1-6}$alkanyloxy, fluoro, hydroxy, and $C_{1-6}$alkanylthio; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-4}$alkanyl and hydroxy;

i) $R_2$ is selected from the group consisting of $C_{1-4}$alkanyl and phenyl; provided that when Z is O or S, $R_2$ is other than unsubstituted $C_{1-4}$alkanyl; and, wherein $C_{1-4}$alkanyl is optionally substituted with one to three substituents independently selected from the group consisting of phenyl, $C_{1-4}$alkanyloxy, hydroxy, fluoro, and phenoxy;

wherein the phenyl and phenoxy substituents of $C_{1-4}$alkanyl are optionally further substituted with, and the phenyl of $R_2$ is optionally substituted with, one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

j) $R_3$ is selected from the group consisting of hydrogen, $C_{1-8}$alkanyl, $C_{2-8}$alkenyl, $C_{2-8}$alkynyl, $C_{1-8}$alkanyloxy$(C_{1-8})$alkanyl, $C_{1-8}$alkanylthio$(C_{1-8})$alkanyl, hydroxy$C_{1-8}$alkanyl, thioformyl, phenylimino$(C_{1-8})$alkanyl, phenyl$(C_{1-8})$alkanyl, and heteroaryl$(C_{1-8})$alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

k) $R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl$(C_{1-8})$alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group;

l) $R_3$ is hydrogen, methyl, allyl, or heteroarylmethyl wherein heteroaryl is selected from the group consisting of benzo[1,3]dioxolyl, imidazolyl, furanyl, pyridinyl, and thienyl;

m) $R_4$ is one to three substituents independently selected from the group consisting of hydrogen, $C_{1-6}$alkanyl, $C_{1-6}$alkanyloxy, aminocarbonyl, aminothiocarbonyl, hydroxyamidino, formylamino, $C_{1-6}$alkanylaminocarbonyl, $C_{1-6}$alkanylcarbonylamino, halogen, hydroxy, $C_{6-10}$aryl; chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thienyl;

n) $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, hydroxy, and aminocarbonyl;

o) $R_4$ is one to two substituents independently selected from the group consisting of hydrogen, methyl, methoxy, bromo, fluoro, 5- or 6-phenyl, 5- or 6-pyridinyl, 5- or 6-furanyl, and hydroxy;

p) $R_5$ is one to two substituents independently selected from the group consisting of hydrogen and halogen;

q) $R_5$ is hydrogen;

r) A is absent or —(CH$_2$)$_2$—;

s) A is —(CH$_2$)$_2$—;

t) X is O or S;

u) n is 0;

v) Z is O, NH, N($C_{1-6}$alkanyl), N(OH), N(O$C_{1-6}$alkanyl), or N(phenyl);

w) Z is O, NH, or N(OH);

x) Z is O or NH;

and combinations of a) through x) above.

One embodiment of the present invention is a compound of Formula (I) wherein:

G is —C(Z)NR$_1$R$_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, isothiazolyl, isoxazolyl, oxazolyl, isoxadiazolyl, quinolinyl, and pyridinyl; wherein phenyl and the heterocycles of G are optionally substituted with one to three substituents independently selected from the group consisting of $C_{1-8}$alkanyl, $C_{1-8}$alkanyloxy, hydroxy$(C_{1-8})$alkanyl, carboxy$(C_{1-8})$alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

R$_1$ is hydrogen or $C_{1-4}$alkanyl;

R$_2$ is selected from the group consisting of hydrogen; $C_{1-4}$alkanyl; phenyl; and $C_{3-6}$cycloalkanyl; provided that when Z is O or S, R$_2$ is other than hydrogen or unsubstituted $C_{1-4}$alkanyl; and, wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; wherein the phenyl and phenoxy substituents of $C_{1-4}$alkanyl are optionally further substituted with, and the phenyl and $C_{3-6}$cycloalkanyl substituents of R$_2$ are optionally substituted with, one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino;

or R$_1$ and R$_2$ taken together with the nitrogen to which they are attached form a 5-7 membered cycloheteroalkyl optionally substituted with phenyl (wherein phenyl is optionally substituted with $C_{1-4}$alkanyloxy or hydroxy), $C_{1-4}$alkanyl, or hydroxy;

R$_3$ is selected from the group consisting of hydrogen, $C_{1-8}$alkanyl, $C_{2-8}$alkenyl, $C_{2-8}$alkynyl, $C_{1-8}$alkanyloxy$(C_{1-8})$alkanyl, $C_{1-8}$alkanylthio$(C_{1-8})$alkanyl, hydroxy$C_{1-8}$alkanyl, thioformyl, phenylimino$(C_{1-8})$alkanyl, phenyl$(C_{1-8})$alkanyl, and heteroaryl$(C_{1-8})$alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

$R_4$ is one to three substituents independently selected from the group consisting of hydrogen, C$_{1-6}$alkanyl, C$_{1-6}$alkanyloxy, aminocarbonyl, aminothiocarbonyl, hydroxyamidino, formylamino, C$_{1-6}$alkanylaminocarbonyl, C$_{1-6}$alkanylcarbonylamino, halogen, hydroxy, C$_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thienyl;

$R_5$ is one to two substituents independently selected from the group consisting of hydrogen and halogen;

A is absent or CH$_2$CH$_2$;

Y is O, S, CH$_2$O or OCH$_2$;

Z is O, NH, N(C$_{1-6}$alkanyl), N(OH), N(OC$_{1-6}$alkanyl), or N(phenyl); and enantiomers, diastereomers, tautomers, solvates, and pharmaceutically acceptable salts thereof.

Another embodiment of the present invention is a compound of Formula (I) wherein:

G is —C(Z)NR$_1$R$_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, furyl, isothiazolyl, isoxazolyl, oxazolyl, isoxadiazolyl, quinolinyl, and pyridinyl; wherein phenyl and the heterocycles of G are optionally substituted with one to three substituents independently selected from the group consisting of C$_{1-4}$alkanyl, C$_{1-4}$alkanyloxy, hydroxy(C$_{1-4}$)alkanyl, carboxy(C$_{1-4}$)alkanyl, C$_{1-4}$alkanylcarbonylamino, hydroxy, cyano, oxo, thioxo, amino, C$_{1-6}$alkanylamino, di(C$_{1-6}$alkanyl)amino, C$_{1-8}$alkanylthio, aminocarbonyl, aminothiocarbonyl, C$_{1-8}$alkanylaminocarbonyl, and di(C$_{1-8}$alkanyl)aminocarbonyl;

R$_1$ is selected from the group consisting of hydrogen, methyl, ethyl, and propyl;

R$_2$ is selected from the group consisting of C$_{1-4}$alkanyl, phenyl, and C$_{3-6}$cycloalkanyl; provided that when Z is O or S, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, fluoro, aminocarbonyl, C$_{1-8}$alkanylaminocarbonyl, di(C$_{1-8}$alkanyl)aminocarbonyl, and phenoxy; wherein the phenyl and phenoxy substituents of C$_{1-4}$alkanyl are optionally further substituted with, and the phenyl of R$_2$ is optionally substituted with, one to three substituents independently selected from the group consisting of C$_{1-6}$alkanyl, C$_{1-6}$alkanyloxy, fluoro, hydroxy, and C$_{1-6}$alkanylthio; or R$_1$ and R$_2$ taken together with the nitrogen to which they are attached form pyrrolidinyl or piperidinyl ring wherein said pyrrolidinyl or piperidinyl is optionally substituted with a substituent selected from the group consisting of C$_{1-3}$alkanyl and hydroxy;

R$_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl(C$_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl wherein the phenyl in any phenyl-containing substituent is optionally substituted with one hydroxyl group;

R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, hydroxy, and aminocarbonyl;

R$_5$ is hydrogen;

A is CH$_2$CH$_2$;

Y is O or S;

Z is O, NH, or N(OH); and enantiomers, diastereomers, tautomers, solvates, and pharmaceutically acceptable salts thereof.

Another embodiment of the present invention is directed to compositions comprising a compound of Formula (I) wherein:

G is —C(Z)NR$_1$R$_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, quinolinyl, and pyridinyl; wherein phenyl and the heterocycles of G are optionally substituted with one to three substituents independently selected from the group consisting of C$_{1-4}$alkanyl, C$_{1-4}$alkanyloxy, hydroxy(C$_{1-4}$)alkanyl, C$_{1-4}$alkanylcarbonylamino, hydroxy, cyano, oxo, thioxo, and aminocarbonyl;

R$_1$ is hydrogen, methyl, or ethyl;

R$_2$ is selected from the group consisting of C$_{1-4}$alkanyl, phenyl, and C$_{3-6}$cycloalkanyl; provided that when Z is O or S, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, fluoro, aminocarbonyl, C$_{1-8}$alkanylaminocarbonyl, di(C$_{1-8}$alkanyl)aminocarbonyl, and phenoxy; wherein the phenyl and phenoxy substituents of C$_{1-4}$alkanyl are optionally further substituted with, and the phenyl of R$_2$ is optionally substituted with, one to three substituents independently selected from the group consisting of C$_{1-6}$alkanyl, C$_{1-6}$alkanyloxy, fluoro, hydroxy, and C$_{1-6}$alkanylthio; or R$_1$ and R$_2$ taken together with the nitrogen to which they are attached form pyrrolidinyl or piperidinyl ring wherein said pyrrolidinyl or piperidinyl is optionally substituted with a substituent selected from the group consisting of C$_{1-3}$alkanyl and hydroxy;

R$_3$ is hydrogen, methyl, allyl, or heteroarylmethyl wherein heteroaryl is selected from the group consisting of benzo[1,3]dioxolyl, imidazolyl, furanyl, pyridinyl, and thienyl;

R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, hydroxy, and aminocarbonyl;

A is CH$_2$CH$_2$;

Y is O or S;

Z is O or NH; and enantiomers, diastereomers, tautomers, solvates, and pharmaceutically acceptable salts thereof.

Another embodiment of the present invention is a compound of Formula (I) wherein:

G is selected from —C(Z)NR$_1$R$_2$, 2-methylcarbonylaminophenyl, 2-aminocarbonyl-phenyl, 1H-tetrazol-5-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;

R$_1$ is hydrogen, methyl, or ethyl;

R$_2$ is selected from the group consisting of C$_{1-4}$alkanyl and phenyl; provided that when Z is O or S, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, fluoro, and phenoxy; wherein the phenyl and phenoxy substituents of C$_{1-4}$alkanyl are optionally further substituted with, and the phenyl of R$_2$ is optionally substituted with, one to three substituents independently selected from the group consisting of C$_{1-6}$alkanyl, C$_{1-6}$alkanyloxy, fluoro, and hydroxy;

or R$_1$ and R$_2$ taken together with the nitrogen to which they are attached form a pyrrolidinyl or piperidinyl ring;

R$_3$ is selected from the group consisting of hydrogen, C$_{1-8}$alkanyl, C$_{2-8}$alkenyl, C$_{2-8}$alkynyl, C$_{1-8}$alkanyloxy (C$_{1-8}$)alkanyl, C$_{1-8}$alkanylthio(C$_{1-8}$)alkanyl, hydroxyC$_{1-8}$alkanyl, thioformyl, phenylimino(C$_{1-8}$)alkanyl, phenyl(C$_{1-8}$)alkanyl, and heteroaryl(C$_{1-8}$)alkanyl wherein heteroaryl is selected from the group consisting of hydrogen, methyl, allyl, or heteroarylmethyl; wherein heteroaryl is selected from the group consisting of benzo[1,3]dioxolyl, imidazolyl, furanyl, pyridinyl, and thienyl; wherein phenyl and heteroaryl are optionally substituted with one to three substituents independently selected from the group consisting of C$_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

R$_4$ is one to three substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, hydroxy, and aminocarbonyl;

R$_5$ is hydrogen;

A is CH$_2$CH$_2$;

Y is O or S;

Z is O or NH; and enantiomers, diastereomers, tautomers, solvates, and pharmaceutically acceptable salts thereof.

Another embodiment of the present invention is directed to compositions comprising a compound of Formula (I) wherein G is independently selected from —C(Z)NR$_1$R$_2$, 2-methylcarbonylaminophenyl, 2-aminocarbonyl-phenyl, 1H-tetrazol-5-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, and pyridin-3-yl; R$_1$ is hydrogen, methyl, or ethyl; R$_2$ is a substituent selected from the group consisting of C$_{1-4}$alkanyl and phenyl; provided that when Z is O or S, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, and 2,6-dimethyl-phenoxy; wherein phenyl of R$_2$ is optionally substituted with one to three substituents independently selected from the group consisting of C$_{1-3}$alkanyl, C$_{1-3}$alkanyloxy, or hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from the group consisting of C$_{1-3}$alkanyl and hydroxy; R$_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-ylmethyl; R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, hydroxy, and aminocarbonyl; A is CH$_2$CH$_2$; Y is O or S; and Z is O or NH.

Another embodiment of the present invention is directed to compositions comprising a compound of Formula (I) wherein G is selected from —C(Z)NR$_1$R$_2$, 2-methylcarbonylaminophenyl, 2-aminocarbonyl-phenyl, 1H-tetrazol-5-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; R$_1$ is hydrogen, methyl, or ethyl; R$_2$ is a substituent selected from the group consisting of C$_{1-4}$alkanyl and phenyl; provided that when Z is O or S, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, and 2,6-dimethyl-phenoxy; and wherein phenyl of R$_2$ is optionally substituted with one to three substituents independently selected from the group consisting of C$_{1-3}$alkanyl, C$_{1-3}$alkanyloxy, fluoro, or hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from the group consisting of C$_{1-3}$alkanyl and hydroxy; R$_3$ is a substituent selected from the group consisting of benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl; R$_4$ is one to two substituents independently selected from the group consisting of hydrogen, methyl, methoxy, bromo, fluoro, 5- or 6-phenyl, 5- or 6-pyridinyl, 5- or 6-furanyl, and hydroxy; A is CH$_2$CH$_2$; Y is O or S; and Z is O or NH.

Another embodiment of the present invention is directed to compositions comprising a compound of Formula (I) wherein G is selected from —C(Z)NR$_1$R$_2$, 2-methylcarbonylaminophenyl, 2-aminocarbonyl-phenyl, 1H-tetrazol-5-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; R$_1$ is hydrogen, methyl, or ethyl; R$_2$ is a substituent selected from the group consisting of C$_{1-4}$alkanyl and phenyl; provided that when Z is O or S, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, and 2,6-dimethyl-phenoxy; wherein phenyl of R$_2$ is optionally substituted with one to three substituents independently selected from the group consisting of $C_{1-3}$alkanyl, $C_{1-3}$alkanyloxy, fluoro, or hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy; $R_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl; $R_4$ is a substituent independently selected from the group consisting of hydrogen, methyl, methoxy, bromo, fluoro, 5- or 6-phenyl, 5- or 6-pyridinyl, 5- or 6-furanyl, and hydroxy; A is $CH_2CH_2$; Y is O or S; and Z is O or NH.

Another embodiment of the present invention is directed to a compound of Formula (I) wherein $R_4$ is preferably substituted at the 5- or 6-position of Formula (I).

Another embodiment of the present invention is directed to compositions comprising a compound selected from the group consisting of:

a compound of Formula (I) wherein G is 1H-tetrazol-5-yl; $R_3$ is H; $R_4$ is H; $R_5$ is H; and Y is O;

a compound of Formula (I) wherein G is 2-methylcarbonylaminophenyl; $R_3$ is H; $R_4$ is H; $R_5$ is H; and Y is O;

a compound of Formula (I) wherein G is N-(2-hydroxyethyl)-N-methyl-aminocarbonyl; $R_3$ is H; $R_4$ is H; $R_5$ is H; and Y is O;

a compound of Formula (I) wherein G is 4H-[1,2,4]-oxadiazol-5-oxo-3-yl; $R_3$ is H; $R_4$ is H; $R_5$ is H; and Y is O;

a compound of Formula (I) wherein G is 4H-[1,2,4]-oxadiazol-5-thioxo-3-yl; $R_3$ is H; $R_4$ is H; $R_5$ is H; and Y is O;

a compound of Formula (I) wherein G is pyrrolidin-1-ylcarbonyl; $R_3$ is H; $R_4$ is H; $R_5$ is H; and Y is O;

a compound of Formula (I) wherein G is N-(2-methoxyethyl)-N-methyl-aminocarbonyl; $R_3$ is H; $R_4$ is H; $R_5$ is H; and Y is O;

a compound of Formula (I) wherein G is 4H-[1,2,4]thiadiazol-5-oxo-3-yl; $R_3$ is H; $R_4$ is H; $R_5$ is H; and Y is O;

a compound of Formula (I) wherein G is N,N-diethylamidino; $R_3$ is H; $R_4$ is H; $R_5$ is H; and Y is O;

a compound of Formula (I) wherein G is [1,2,3,5]oxathiadiazol-2-oxo-4-yl; $R_3$ is H; $R_4$ is H; $R_5$ is H; and Y is O;

a compound of Formula (I) wherein G is N-(3-fluorophenyl)-methyl-aminocarbonyl; $R_3$ is H; $R_4$ is H; $R_5$ is H; and Y is O;

a compound of Formula (I) wherein G is pyridin-3-yl; $R_3$ is H; $R_4$ is H; $R_5$ is H; and Y is O;

a compound of Formula (I) wherein G is N-[2-(2,6-dimethylphenoxy)-1-methyl-ethyl]aminocarbonyl; $R_3$ is H; $R_4$ is H; $R_5$ is H; and Y is O;

a compound of Formula (I) wherein G is N-phenyl-N-methyl-aminocarbonyl; $R_3$ is H; $R_4$ is H; $R_5$ is H; and Y is O;

a compound of Formula (I) wherein G is N-(1 (S)-hydroxymethyl-2-phenyl-eth-1-yl)aminocarbonyl; $R_3$ is H; $R_4$ is H; $R_5$ is H; and Y is O;

a compound of Formula (I) wherein G is 2-methyl-tetrazol-5-yl; $R_3$ is H; $R_4$ is H; $R_5$ is H; and Y is O;

a compound of Formula (I) wherein G is N-(2-phenylethyl)-N-methyl-aminocarbonyl; $R_3$ is H; $R_4$ is H; $R_5$ is H; and Y is O;

a compound of Formula (I) wherein G is 2-aminocarbonylphenyl; $R_3$ is H; $R_4$ is H; $R_5$ is H; and Y is O;

a compound of Formula (I) wherein G is 2-phenylethyl-aminocarbonyl; $R_3$ is H; $R_4$ is H; $R_5$ is H; and Y is O;

a compound of Formula (I) wherein G is 3-methylcarbonylamino-phenyl; $R_3$ is H; $R_4$ is H; $R_5$ is H; and Y is O;

a compound of Formula (I) wherein G is 1-methyl-tetrazol-5-yl; $R_3$ is H; $R_4$ is H; $R_5$ is H; and Y is O;

a compound of Formula (I) wherein G is N-cyclohexyl-N-methyl-aminocarbonyl; $R_3$ is H; $R_4$ is H; $R_5$ is H; and Y is O;

a compound of Formula (I) wherein G is 3-hydroxymethyl-phenyl; $R_3$ is H; $R_4$ is H; $R_5$ is H; and Y is O;

a compound of Formula (I) wherein G is N-hydroxyamidino; $R_3$ is H; $R_4$ is H; $R_5$ is H; and Y is O;

compound of Formula (I) wherein G is 2-aminophenyl; $R_3$ is H; $R_4$ is H; $R_5$ is H; and Y is O;

a compound of Formula (I) wherein G is 5-ethyl-1H-imidazol-2-yl; $R_3$ is H; $R_4$ is H; $R_5$ is H; and Y is O;

a compound of Formula (I) wherein G is N-(1(R)-hydroxymethyl-2-phenyl-eth-1-yl)-aminocarbonyl; $R_3$ is H; $R_4$ is H; $R_5$ is H; and Y is O;

a compound of Formula (I) wherein G is N, N-diisobutylamidino; $R_3$ is H; $R_4$ is H; $R_5$ is H; and Y is O;

a compound of Formula (I) wherein G is pyridin-4-yl; $R_3$ is H; $R_4$ is H; $R_5$ is H; and Y is O;

a compound of Formula (I) wherein G is 4-methylcarbonylamino-phenyl; $R_3$ is H; $R_4$ is H; $R_5$ is H; and Y is O;

a compound of Formula (I) wherein G is N-(1S-methoxymethyl-2-phenyl-eth-1-yl)aminocarbonyl; $R_3$ is H; $R_4$ is H; $R_5$ is H; and Y is O;

a compound of Formula (I) wherein G is 2-methoxypyridin-5-yl; $R_3$ is H; $R_4$ is H; $R_5$ is H; and Y is O;

a compound of Formula (I) wherein G is 4,5-dihydro-1H-imidazol-2-yl; $R_3$ is H; $R_4$ is H; $R_5$ is H; and Y is O;

a compound of Formula (I) wherein G is N-(4-phenyl)-cyclohexyl-aminocarbonyl; $R_3$ is H; $R_4$ is H; $R_5$ is H; and Y is O;

a compound of Formula (I) wherein G is 3-methyl-4H-[1,2,4]triazol-5-yl; $R_3$ is H; $R_4$ is H; $R_5$ is H; and Y is O;

a compound of Formula (I) wherein G is 5-methyl-[1,2,4]oxadiazol-4-yl; $R_3$ is H; $R_4$ is H; $R_5$ is H; and Y is O;

a compound of Formula (I) wherein G is N-(1(S)-hydroxymethyl-1-methoxycarbonyl)aminocarbonyl; $R_3$ is H; $R_4$ is H; $R_5$ is H; and Y is O;

a compound of Formula (I) wherein G is 3-hydroxy-phenyl; $R_3$ is H; $R_4$ is H; $R_5$ is H; and Y is O;

a compound of Formula (I) wherein G is isopropylamidino; $R_3$ is H; $R_4$ is H; $R_5$ is H; and Y is O;

a compound of Formula (I) wherein G is phenylmethylaminocarbonyl; $R_3$ is H; $R_4$ is H; $R_5$ is H; and Y is O;

a compound of Formula (I) wherein G is 1,4,5,6-tetrahydropyrimidin-2-yl; $R_3$ is H; $R_4$ is H; $R_5$ is H; and Y is O;

a compound of Formula (I) wherein G is 4-aminophenyl; $R_3$ is H; $R_4$ is H; $R_5$ is H; and Y is O;

a compound of Formula (I) wherein G is C-piperidin-1-yl-methyleneamine; $R_3$ is H; $R_4$ is H; $R_5$ is H; and Y is O;

a compound of Formula (I) wherein G is 2-methoxyphenyl; $R_3$ is H; $R_4$ is H; $R_5$ is H; and Y is O;

a compound of Formula (I) wherein G is cyclopentylaminocarbonyl; $R_3$ is H; $R_4$ is H; $R_5$ is H; and Y is O;

a compound of Formula (I) wherein G is 3-methylphenyl; $R_3$ is H; $R_4$ is H; $R_5$ is H; and Y is O;

a compound of Formula (I) wherein G is phenylaminocarbonyl; $R_3$ is H; $R_4$ is H; $R_5$ is H; and Y is O;

a compound of Formula (I) wherein G is N,N-bis(2,2,2-trifluoro-eth-1-yl)aminocarbonyl; $R_3$ is H; $R_4$ is H; $R_5$ is H; and Y is O;

a compound of Formula (I) wherein G is isobutylamidino; $R_3$ is H; $R_4$ is H; $R_5$ is H; and Y is O;

a compound of Formula (I) wherein G is C-morpholin-4-yl-methyleneamine; $R_3$ is H; $R_4$ is H; $R_5$ is H; and Y is O;

a compound of Formula (I) wherein G is 3-fluorophenyl; $R_3$ is H; $R_4$ is H; $R_5$ is H; and Y is O;

a compound of Formula (I) wherein G is N-benzyl-N-methyl-aminocarbonyl; $R_3$ is H; $R_4$ is H; $R_5$ is H; and Y is O;

a compound of Formula (I) wherein G is 4-methanesulfonyl-phenyl; $R_3$ is H; $R_4$ is H; $R_5$ is H; and Y is O;

a compound of Formula (I) wherein G is 4-fluorophenyl; $R_3$ is H; $R_4$ is H; $R_5$ is H; and Y is O;

a compound of Formula (I) wherein G is thiophen-3-yl; $R_3$ is H; $R_4$ is H; $R_5$ is H; and Y is O;

a compound of Formula (I) wherein G is N-(2-dimethylamino-eth-1-yl)-N-methyl-aminocarbonyl; $R_3$ is H; $R_4$ is H; $R_5$ is H; and Y is O;

a compound of Formula (I) wherein G is 3-methoxyphenyl; $R_3$ is H; $R_4$ is H; $R_5$ is H; and Y is O;

a compound of Formula (I) wherein G is phenylmethylaminocarbonyl; $R_3$ is ethoxycarbonyl; $R_4$ is H; $R_5$ is H; and Y is O;

a compound of Formula (I) wherein G is phenylaminocarbonyl; $R_3$ is ethoxycarbonyl; $R_4$ is H; $R_5$ is H; and Y is O;

a compound of Formula (I) wherein G is cyclopentylaminocarbonyl; $R_3$ is ethoxycarbonyl; $R_4$ is H; $R_5$ is H; and Y is O;

a compound of Formula (I) wherein G is N-(2-dimethylamino-eth-1-yl)-N-methyl-aminocarbonyl; $R_3$ is ethoxycarbonyl; $R_4$ is H; $R_5$ is H; and Y is O;

a compound of Formula (I) wherein G is N-[(4-trifluoromethyl)-cyclohexyl]-aminocarbonyl; $R_3$ is H; $R_4$ is H; $R_5$ is H; and Y is O;

a compound of Formula (I) wherein G is 3-methanesulfonylamino-phenyl; $R_3$ is H; $R_4$ is H; $R_5$ is H; and Y is O;

a compound of Formula (I) wherein G is N-2,2,2,-trifluoro-ethyl-aminocarbonyl; $R_3$ is H; $R_4$ is H; $R_5$ is H; and Y is O;

a compound of Formula (I) wherein G is 3-[(3-methoxy)phenyl]piperidin-1-ylcarbonyl; $R_3$ is H; $R_4$ is H; $R_5$ is H; and Y is O;

a compound of Formula (I) wherein G is N-4-fluorophenyl-N-methyl-aminocarbonyl; $R_3$ is H; $R_4$ is H; $R_5$ is H; and Y is O;

a compound of Formula (I) wherein G is N-(1(R)-hydroxymethyl-3-methyl-but-1-yl)-aminocarbonyl; $R_3$ is H; $R_4$ is H; $R_5$ is H; and Y is O;

a compound of Formula (I) wherein G is N-(dimethylaminocarbonylmethyl)-N-methyl-aminocarbonyl; $R_3$ is H; $R_4$ is H; $R_5$ is H; and Y is O;

a compound of Formula (I) wherein G is (3(R)-hydroxy)pyrrolidin-1-ylcarbonyl; $R_3$ is H; $R_4$ is H; $R_5$ is H; and Y is O;

a compound of Formula (I) wherein G is (3(S)-hydroxy)pyrrolidin-1-ylcarbonyl; $R_3$ is H; $R_4$ is H; $R_5$ is H; and Y is O;

a compound of Formula (I) wherein G is pyridin-3-yl; $R_3$ is H; $R_4$ is 5-methoxy; $R_5$ is H; and Y is O;

a compound of Formula (I) wherein G is N-(2-hydroxyethyl)-N-methyl-aminocarbonyl; $R_3$ is ethoxycarbonyl; $R_4$ is H; $R_5$ is H; and Y is O;

a compound of Formula (I) wherein G is 1H-tetrazol-5-yl; $R_3$ is H; $R_4$ is H; $R_5$ is H; and Y is O;

a compound of Formula (I) wherein G is 1H-tetrazol-5-yl; $R_3$ is H; $R_4$ is H; $R_5$ is H; and Y is O;

a compound of Formula (I) wherein G is 1H-tetrazol-5-yl; $R_3$ is H; $R_4$ is 5-methoxy; $R_5$ is H; and Y is O;

a compound of Formula (I) wherein G is phenylthio; $R_3$ is H; $R_4$ is H; $R_5$ is H; and Y is S;

a compound of Formula (I) wherein G is 1H-tetrazol-5-yl; $R_3$ is H; $R_4$ is 5-hydroxy; $R_5$ is H; and Y is O;

a compound of Formula (I) wherein G is 4H-[1,2,4]-oxadiazol-5-oxo-3-yl; $R_3$ is H; $R_4$ is H; $R_5$ is H; and Y is O;

a compound of Formula (I) wherein G is 4H-[1,2,4]-oxadiazol-5-oxo-3-yl; $R_3$ is H; $R_4$ is H; $R_5$ is H; and Y is O;

a compound of Formula (I) wherein G is 4H-[1,2,4]-oxadiazol-5-thioxo-3-yl; $R_3$ is H; $R_4$ is H; $R_5$ is H; and Y is O;

a compound of Formula (I) wherein G is 4H-[1,2,4]-oxadiazol-5-thioxo-3-yl; $R_3$ is H; $R_4$ is H; $R_5$ is H; and Y is O;

a compound of Formula (I) wherein G is 4H-[1,2,4]thiadiazol-5-oxo-3-yl; $R_3$ is H; $R_4$ is H; $R_5$ is H; and Y is O;

a compound of Formula (Ib) wherein G is methoxycarbonyl; $R_3$ is H; $R_4$ is H; $R_5$ is H; and Y is O;

a compound of Formula (I) wherein G is N-(2-hydroxy-1,1-dimethylethyl)-aminocarbonyl; $R_3$ is H; $R_4$ is H; $R_5$ is H; and Y is O;

a compound of Formula (I) wherein G is 4H-[1,2,4]thiadiazol-5-oxo-3-yl; $R_3$ is H; $R_4$ is H; $R_5$ is H; and Y is O;

a compound of Formula (I) wherein G is 1H-tetrazol-5-yl; $R_3$ is H; $R_4$ is H; $R_5$ is H; and Y is S;

a compound of Formula (I) wherein G is 1H-tetrazol-5-yl; $R_3$ is H; $R_4$ is H; $R_5$ is H; and Y is S;

a compound of Formula (I) wherein G is quinolin-3-yl; $R_3$ is H; $R_4$ is 5-methoxy; $R_5$ is H; and Y is O;

a compound of Formula (I) wherein G is fur-3-yl; $R_3$ is H; $R_4$ is 5-methoxy; $R_5$ is H; and Y is O;

a compound of Formula (I) wherein G is thien-3-yl; $R_3$ is H; $R_4$ is 5-methoxy; $R_5$ is H; and Y is O;

a compound of Formula (I) wherein G is pyridin-4-yl; $R_3$ is H; $R_4$ is 5-methoxy; $R_5$ is H; and Y is O;

a compound of Formula (I) wherein G is 2-methylcarbonylaminophenyl; $R_3$ is H; $R_4$ is 5-methoxy; $R_5$ is H; and Y is O;

a compound of Formula (I) wherein G is quinolin-3-yl; $R_3$ is H; $R_4$ is 5-hydroxy; $R_5$ is H; and Y is O;

a compound of Formula (I) wherein G is N-(2-hydroxyethyl)-aminocarbonyl; $R_3$ is H; $R_4$ is H; $R_5$ is H; and Y is O;

a compound of Formula (I) wherein G is 1-methyl-pyrazol-3-yl; $R_3$ is H; $R_4$ is H; $R_5$ is H; and Y is O;

a compound of Formula (I) wherein G is pyridin-3-yl; $R_3$ is H; $R_4$ is H; $R_5$ is H; and Y is S;

a compound of Formula (I) wherein G is 2-methylcarbonylaminophenyl; $R_3$ is H; $R_4$ is H; $R_5$ is H; and Y is S;

a compound of Formula (I) wherein G is pyridin-3-yl; $R_3$ is methyl; $R_4$ is H; $R_5$ is H; and Y is S;

a compound of Formula (I) wherein G is pyridin-3-yl; $R_3$ is 1H-imidazol-2-ylmethyl; $R_4$ is H; $R_5$ is H; and Y is S;

a compound of Formula (I) wherein G is pyridin-3-yl; $R_3$ is fur-3-ylmethyl; $R_4$ is H; $R_5$ is H; and Y is S;

a compound of Formula (I) wherein G is pyridin-3-yl; $R_3$ is pyridin-2-ylmethyl; $R_4$ is H; $R_5$ is H; and Y is S;

a compound of Formula (I) wherein G is 2-methylcarbonylaminophenyl; $R_3$ is methyl; $R_4$ is H; $R_5$ is H; and Y is S;

a compound of Formula (I) wherein G is 2-methylcarbonylaminophenyl; $R_3$ is 1H-imidazol-2-ylmethyl; $R_4$ is H; $R_5$ is H; and Y is S;

a compound of Formula (I) wherein G is 2-methylcarbonylaminophenyl; $R_3$ is fur-3-ylmethyl; $R_4$ is H; $R_5$ is H; and Y is S;

a compound of Formula (I) wherein G is 2-methylcarbonylaminophenyl; $R_3$ is pyridin-2-ylmethyl; $R_4$ is H; $R_5$ is H; and Y is S;

a compound of Formula (I) wherein G is N-(2-hydroxyethyl)-aminocarbonyl; $R_3$ is t-butoxycarbonyl; $R_4$ is H; $R_5$ is H; and Y is O;

a compound of Formula (I) wherein G is N-(2-hydroxyethyl)-aminocarbonyl; $R_3$ is H; $R_4$ is H; $R_5$ is H; and Y is O;

a compound of Formula (I) wherein G is N-(2-hydroxyethyl)-N-methyl-aminocarbonyl; $R_3$ is H; $R_4$ is H; $R_5$ is H; and Y is O;

a compound of Formula (I) wherein G is N,N-diethylamidino; $R_3$ is H; $R_4$ is H; $R_5$ is H; and Y is O;
a compound of Formula (I) wherein G is N,N-diethylamidino; $R_3$ is H; $R_4$ is H; $R_5$ is H; and Y is O;
a compound of Formula (I) wherein G is (3(R)-hydroxy) pyrrolidin-1-ylcarbonyl; $R_3$ is H; $R_4$ is H; $R_5$ is H; and Y is O;
a compound of Formula (I) wherein G is pyridin-3-yl; $R_3$ is trifluoromethylcarbonyl; $R_4$ is H; $R_5$ is H; and Y is O;
a compound of Formula (I) wherein G is pyridin-3-yl; $R_3$ is trifluoromethylcarbonyl; $R_4$ is H; $R_5$ is H; and Y is O;
a compound of Formula (I) wherein G is 2-methylcarbonylaminophenyl; $R_3$ is trifluoromethylcarbonyl; $R_4$ is H; $R_5$ is H; and Y is O;
a compound of Formula (I) wherein G is 2-methylcarbonylaminophenyl; $R_3$ is trifluoromethylcarbonyl; $R_4$ is H; $R_5$ is H; and Y is O;
a compound of Formula (I) wherein G is 4H-[1,2,4]-oxadiazol-5-oxo-3-yl; $R_3$ is H; $R_4$ is 5-methoxy; $R_5$ is H; and Y is O;
a compound of Formula (I) wherein G is 4H-[1,2,4]-oxadiazol-5-thioxo-3-yl; $R_3$ is H; $R_4$ is 5-methoxy; $R_5$ is H; and Y is O; and
a compound of Formula (I) wherein G is 4H-[1,2,4]-oxadiazol-5-oxo-3-yl; $R_3$ is H; $R_4$ is 5-hydroxy; $R_5$ is H; and Y is O.

Another embodiment of the present invention is directed to compositions comprising a compound selected from the group consisting of:
a compound of Formula (I) wherein G is 1H-tetrazol-5-yl; $R_3$ is H; $R_4$ is H; $R_5$ is H; and Y is O;
a compound of Formula (I) wherein G is 2-methylcarbonylaminophenyl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is pyrrolidin-1-ylcarbonyl; $R_3$ is H; $R_4$ is H; $R_5$ is H; and Y is O;
a compound of Formula (I) wherein G is N-(2-methoxyethyl)-N-methyl-aminocarbonyl; $R_3$ is H; $R_4$ is H; $R_5$ is H; and Y is O;
a compound of Formula (I) wherein G is 4H-[1,2,4]thiadiazol-5-oxo-3-yl; $R_3$ is H; $R_4$ is H; $R_5$ is H; and Y is O;
a compound of Formula (I) wherein G is N,N-diethylamidino; $R_3$ is H; $R_4$ is H; $R_5$ is H; and Y is O;
a compound of Formula (I) wherein G is [1,2,3,5]oxathiadiazol-2-oxo-4-yl; $R_3$ is H; $R_4$ is H; $R_5$ is H; and Y is O;
a compound of Formula (I) wherein G is N-(3-fluorophenyl)-methyl-aminocarbonyl; $R_3$ is H; $R_4$ is H; $R_5$ is H; and Y is O;
a compound of Formula (I) wherein G is pyridin-3-yl; $R_3$ is H; $R_4$ is H; $R_5$ is H; and Y is O;
a compound of Formula (I) wherein G is N-[2-(2,6-dimethylphenoxy)-1-methyl-ethyl]aminocarbonyl; $R_3$ is H; $R_4$ is H; $R_5$ is H; and Y is O;
a compound of Formula (I) wherein G is N-phenyl-N-methyl-aminocarbonyl; $R_3$ is H; $R_4$ is H; $R_5$ is H; and Y is O;
a compound of Formula (I) wherein G is N-(1 (S)-hydroxymethyl-2-phenyl-eth-1-yl)aminocarbonyl; $R_3$ is H; $R_4$ is H; $R_5$ is H; and Y is O;
a compound of Formula (I) wherein G is 2-methyl-tetrazol-5-yl; $R_3$ is H; $R_4$ is H; $R_5$ is H; and Y is O;
a compound of Formula (I) wherein G is N-(2-phenylethyl)-N-methyl-aminocarbonyl; $R_3$ is H; $R_4$ is H; $R_5$ is H; and Y is O;
a compound of Formula (I) wherein G is 2-aminocarbonylphenyl; $R_3$ is H; $R_4$ is H; $R_5$ is H; and Y is O;
a compound of Formula (I) wherein G is 2-phenylethyl-aminocarbonyl; $R_3$ is H; $R_4$ is H; $R_5$ is H; and Y is O;
a compound of Formula (I) wherein G is 3-methylcarbonylamino-phenyl; $R_3$ is H; $R_4$ is H; $R_5$ is H; and Y is O;
a compound of Formula (I) wherein G is 1-methyl-tetrazol-5-yl; $R_3$ is H; $R_4$ is H; $R_5$ is H; and Y is O;
a compound of Formula (I) wherein G is N-cyclohexyl-N-methyl-aminocarbonyl; $R_3$ is H; $R_4$ is H; $R_5$ is H; and Y is O;
a compound of Formula (I) wherein G is 3-hydroxymethyl-phenyl; $R_3$ is H; $R_4$ is H; $R_5$ is H; and Y is O;
a compound of Formula (I) wherein G is N-hydroxyamidino; $R_3$ is H; $R_4$ is H; $R_5$ is H; and Y is O;
a compound of Formula (I) wherein G is 2-aminophenyl; $R_3$ is H; $R_4$ is H; $R_5$ is H; and Y is O;
a compound of Formula (I) wherein G is 5-ethyl-1H-imidazol-2-yl; $R_3$ is H; $R_4$ is H; $R_5$ is H; and Y is O;
a compound of Formula (I) wherein G is N-(1(R)-hydroxymethyl-2-phenyl-eth-1-yl)-aminocarbonyl; $R_3$ is H; $R_4$ is H; $R_5$ is H; and Y is O;
a compound of Formula (I) wherein G is N, N-diisobutylamidino; $R_3$ is H; $R_4$ is H; $R_5$ is H; and Y is O;
a compound of Formula (I) wherein G is pyridin-4-yl; $R_3$ is H; $R_4$ is H; $R_5$ is H; and Y is O;
a compound of Formula (I) wherein G is 4-methylcarbonylamino-phenyl; $R_3$ is H; $R_4$ is H; $R_5$ is H; and Y is O;
a compound of Formula (I) wherein G is N-(1S-methoxymethyl-2-phenyl-eth-1-yl)aminocarbonyl; $R_3$ is H; $R_4$ is H; $R_5$ is H; and Y is O;
a compound of Formula (I) wherein G is 2-methoxypyridin-5-yl; $R_3$ is H; $R_4$ is H; $R_5$ is H; and Y is O;
a compound of Formula (I) wherein G is 4,5-dihydro-1H-imidazol-2-yl; $R_3$ is H; $R_4$ is H; $R_5$ is H; and Y is O;
a compound of Formula (I) wherein G is N-(4-phenyl)-cyclohexyl-aminocarbonyl; $R_3$ is H; $R_4$ is H; $R_5$ is H; and Y is O;
a compound of Formula (I) wherein G is 3-methyl-4H-[1,2,4]triazol-5-yl; $R_3$ is H; $R_4$ is H; $R_5$ is H; and Y is O;
a compound of Formula (I) wherein G is N-(2-dimethylamino-eth-1-yl)-N-methyl-aminocarbonyl; $R_3$ is ethoxycarbonyl; $R_4$ is H; $R_5$ is H; and Y is O;
a compound of Formula (I) wherein G is 3-methanesulfonylamino-phenyl; $R_3$ is H; $R_4$ is H; $R_5$ is H; and Y is O;
a compound of Formula (I) wherein G is N-2,2,2,-trifluoroethyl-aminocarbonyl; $R_3$ is H; $R_4$ is H; $R_5$ is H; and Y is O;
a compound of Formula (I) wherein G is 3-[(3-methoxy)phenyl]piperidin-1-ylcarbonyl; $R_3$ is H; $R_4$ is H; $R_5$ is H; and Y is O;
a compound of Formula (I) wherein G is N-4-fluorophenyl-N-methyl-aminocarbonyl; $R_3$ is H; $R_4$ is H; $R_5$ is H; and Y is O;
a compound of Formula (I) wherein G is N-(dimethylaminocarbonylmethyl)-N-methyl-aminocarbonyl; $R_3$ is H; $R_4$ is H; $R_5$ is H; and Y is O;
a compound of Formula (I) wherein G is (3(R)-hydroxy) pyrrolidin-1-ylcarbonyl; $R_3$ is H; $R_4$ is H; $R_5$ is H; and Y is O;
a compound of Formula (I) wherein G is (3(S)-hydroxy) pyrrolidin-1-ylcarbonyl; $R_3$ is H; $R_4$ is H; $R_5$ is H; and Y is O;
a compound of Formula (I) wherein G is pyridin-3-yl; $R_3$ is H; $R_4$ is 5-methoxy; $R_5$ is H; and Y is O;
a compound of Formula (I) wherein G is 1H-tetrazol-5-yl; $R_3$ is H; $R_4$ is H; $R_5$ is H; and Y is O;
a compound of Formula (I) wherein G is 1H-tetrazol-5-yl; $R_3$ is H; $R_4$ is 5-methoxy; $R_5$ is H; and Y is O;

a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is 4H-[1,2,4]thiadiazol-5-oxo-3-yl; $R_3$ is H; $R_4$ is H; $R_5$ is H; and Y is O;
a compound of Formula (I) wherein G is N-(2-hydroxy-1,1-dimethyl-ethyl)-aminocarbonyl; $R_3$ is H; $R_4$ is H; $R_5$ is H; and Y is O;
a compound of Formula (I) wherein G is 4H-[1,2,4]thiadiazol-5-oxo-3-yl; $R_3$ is H; $R_4$ is H; $R_5$ is H; and Y is O;
a compound of Formula (I) wherein G is 1H-tetrazol-5-yl; $R_3$ is H; $R_4$ is H; $R_5$ is H; and Y is S;
a compound of Formula (I) wherein G is 1H-tetrazol-5-yl; $R_3$ is H; $R_4$ is H; $R_5$ is H; and Y is S;
a compound of Formula (I) wherein G is quinolin-3-yl; $R_3$ is H; $R_4$ is 5-methoxy; $R_5$ is H; and Y is O;
a compound of Formula (I) wherein G is fur-3-yl; $R_3$ is H; $R_4$ is 5-methoxy; $R_5$ is H; and Y is O;
a compound of Formula (I) wherein G is thien-3-yl; $R_3$ is H; $R_4$ is 5-methoxy; $R_5$ is H; and Y is O;
a compound of Formula (I) wherein G is pyridin-4-yl; $R_3$ is H; $R_4$ is 5-methoxy; $R_5$ is H; and Y is O;
a compound of Formula (I) wherein G is 2-methylcarbonylamino-phenyl; $R_3$ is H; $R_4$ is 5-methoxy; $R_5$ is H; and Y is O;
a compound of Formula (I) wherein G is quinolin-3-yl; $R_3$ is H; $R_4$ is 5-hydroxy; $R_5$ is H; and Y is O;
a compound of Formula (I) wherein G is 1-methyl-pyrazol-3-yl; $R_3$ is H; $R_4$ is H; $R_5$ is H; and Y is O;
a compound of Formula (I) wherein G is 2-methylcarbonylamino-phenyl; $R_3$ is H; $R_4$ is H; $R_5$ is H; and Y is S;
a compound of Formula (I) wherein G is pyridin-3-yl; $R_3$ is methyl; $R_4$ is H; $R_5$ is H; and Y is S;
a compound of Formula (I) wherein G is pyridin-3-yl; $R_3$ is 1H-imidazol-2-ylmethyl; $R_4$ is H; $R_5$ is H; and Y is S;
a compound of Formula (I) wherein G is pyridin-3-yl; $R_3$ is fur-3-ylmethyl; $R_4$ is H; $R_5$ is H; and Y is S;
a compound of Formula (I) wherein G is pyridin-3-yl; $R_3$ is pyridin-2-ylmethyl; $R_4$ is H; $R_5$ is H; and Y is S;
a compound of Formula (I) wherein G is 2-methylcarbonylamino-phenyl; $R_3$ is 1H-imidazol-2-ylmethyl; $R_4$ is H; $R_5$ is H; and Y is S;
a compound of Formula (I) wherein G is 2-methylcarbonylamino-phenyl; $R_3$ is fur-3-ylmethyl; $R_4$ is H; $R_5$ is H; and Y is S;
a compound of Formula (I) wherein G is 2-methylcarbonylamino-phenyl; $R_3$ is pyridin-2-ylmethyl; $R_4$ is H; $R_5$ is H; and Y is S;
a compound of Formula (I) wherein G is N-(2-hydroxyethyl)-aminocarbonyl; $R_3$ is H; $R_4$ is H; $R_5$ is H; and Y is O;
a compound of Formula (I) wherein G is N,N-diethylamidino; $R_3$ is H; $R_4$ is H; $R_5$ is H; and Y is O;
a compound of Formula (I) wherein G is (3(R)-hydroxy) pyrrolidin-1-ylcarbonyl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is 5-methoxy; $R_5$ is H; and Y is O;
a compound of Formula (I) wherein G is 4H-[1,2,4]-oxadiazol-5-thioxo-3-yl; $R_3$ is H; $R_4$ is 5-methoxy; $R_5$ is H; and Y is O; and
a compound of Formula (I) wherein G is 4H-[1,2,4]-oxadiazol-5-oxo-3-yl; $R_3$ is H; $R_4$ is 5-hydroxy; $R_5$ is H; and Y is O.

Another embodiment of the present invention is directed to compositions comprising a compound selected from the group consisting of:
a compound of Formula (I) wherein G is 1H-tetrazol-5-yl; $R_3$ is H; $R_4$ is H; $R_5$ is H; and Y is O;
a compound of Formula (I) wherein G is 2-methylcarbonylaminophenyl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is pyrrolidin-1-ylcarbonyl; $R_3$ is H; $R_4$ is H; $R_5$ is H; and Y is O;
a compound of Formula (I) wherein G is N-(2-methoxyethyl)-N-methyl-aminocarbonyl; $R_3$ is H; $R_4$ is H; $R_5$ is H; and Y is O;
a compound of Formula (I) wherein G is 4H-[1,2,4]thiadiazol-5-oxo-3-yl; $R_3$ is H; $R_4$ is H; $R_5$ is H; and Y is O;
a compound of Formula (I) wherein G is N,N-diethylamidino; $R_3$ is H; $R_4$ is H; $R_5$ is H; and Y is O;
a compound of Formula (I) wherein G is [1,2,3,5]oxathiadiazol-2-oxo-4-yl; $R_3$ is H; $R_4$ is H; $R_5$ is H; and Y is O;
a compound of Formula (I) wherein G is N-(3-fluorophenyl)-methyl-aminocarbonyl; $R_3$ is H; $R_4$ is H; $R_5$ is H; and Y is O;
a compound of Formula (I) wherein G is pyridin-3-yl; $R_3$ is H; $R_4$ is H; $R_5$ is H; and Y is O;
a compound of Formula (I) wherein G is N-[2-(2,6-dimethylphenoxy)-1-methyl-ethyl]aminocarbonyl; $R_3$ is H; $R_4$ is H; $R_5$ is H; and Y is O;
a compound of Formula (I) wherein G is N-phenyl-N-methyl-aminocarbonyl; $R_3$ is H; $R_4$ is H; $R_5$ is H; and Y is O;
a compound of Formula (I) wherein G is N-(1(S)-hydroxymethyl-2-phenyl-eth-1-yl)aminocarbonyl; $R_3$ is H; $R_4$ is H; $R_5$ is H; and Y is O;
a compound of Formula (I) wherein G is 2-methyl-tetrazol-5-yl; $R_3$ is H; $R_4$ is H; $R_5$ is H; and Y is O;
a compound of Formula (I) wherein G is N-(2-phenylethyl)-N-methyl-aminocarbonyl; $R_3$ is H; $R_4$ is H; $R_5$ is H; and Y is O;
a compound of Formula (I) wherein G is 2-aminocarbonylphenyl; $R_3$ is H; $R_4$ is H; $R_5$ is H; and Y is O;
a compound of Formula (I) wherein G is 2-phenylethyl-aminocarbonyl; $R_3$ is H; $R_4$ is H; $R_5$ is H; and Y is O;
a compound of Formula (I) wherein G is 3-methylcarbonylamino-phenyl; $R_3$ is H; $R_4$ is H; $R_5$ is H; and Y is O;
a compound of Formula (I) wherein G is 1-methyl-tetrazol-5-yl; $R_3$ is H; $R_4$ is H; $R_5$ is H; and Y is O;
a compound of Formula (I) wherein G is N-cyclohexyl-N-methyl-aminocarbonyl; $R_3$ is H; $R_4$ is H; $R_5$ is H; and Y is O;
a compound of Formula (I) wherein G is 3-hydroxymethyl-phenyl; $R_3$ is H; $R_4$ is H; $R_5$ is H; and Y is O;
a compound of Formula (I) wherein G is N-hydroxyamidino; $R_3$ is H; $R_4$ is H; $R_5$ is H; and Y is O;
a compound of Formula (I) wherein G is 2-aminophenyl; $R_3$ is H; $R_4$ is H; $R_5$ is H; and Y is O;
a compound of Formula (I) wherein G is 5-ethyl-1H-imidazol-2-yl; $R_3$ is H; $R_4$ is H; $R_5$ is H; and Y is O;
a compound of Formula (I) wherein G is N-(1(R)-hydroxymethyl-2-phenyl-eth-1-yl)-aminocarbonyl; $R_3$ is H; $R_4$ is H; $R_5$ is H; and Y is O;

a compound of Formula (I) wherein G is N-(2-dimethylamino-eth-1-yl)-N-methyl-aminocarbonyl; $R_3$ is ethoxycarbonyl; $R_4$ is H; $R_5$ is H; and Y is O;
a compound of Formula (I) wherein G is N-2,2,2,-trifluoroethyl-aminocarbonyl; $R_3$ is H; $R_4$ is H; $R_5$ is H; and Y is O;
a compound of Formula (I) wherein G is 3-[(3-methoxy)phenyl]piperidin-1-ylcarbonyl; $R_3$ is H; $R_4$ is H; $R_5$ is H; and Y is O;
a compound of Formula (I) wherein G is N-4-fluorophenyl-N-methyl-aminocarbonyl; $R_3$ is H; $R_4$ is H; $R_5$ is H; and Y is O;
a compound of Formula (I) wherein G is N-(dimethylaminocarbonylmethyl)-N-methyl-aminocarbonyl; $R_3$ is H; $R_4$ is H; $R_5$ is H; and Y is O;
a compound of Formula (I) wherein G is (3(S)-hydroxy)pyrrolidin-1-ylcarbonyl; $R_3$ is H; $R_4$ is H; $R_5$ is H; and Y is O;
a compound of Formula (I) wherein G is pyridin-3-yl; $R_3$ is H; $R_4$ is 5-methoxy; $R_5$ is H; and Y is O;
a compound of Formula (I) wherein G is 1H-tetrazol-5-yl; $R_3$ is H; $R_4$ is H; $R_5$ is H; and Y is O;
a compound of Formula (I) wherein G is 1H-tetrazol-5-yl; $R_3$ is H; $R_4$ is 5-methoxy; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is 4H-[1,2,4]thiadiazol-5-oxo-3-yl; $R_3$ is H; $R_4$ is H; $R_5$ is H; and Y is O;
a compound of Formula (I) wherein G is 1H-tetrazol-5-yl; $R_3$ is H; $R_4$ is H; $R_5$ is H; and Y is S;
a compound of Formula (I) wherein G is 1H-tetrazol-5-yl; $R_3$ is H; $R_4$ is H; $R_5$ is H; and Y is S;
a compound of Formula (I) wherein G is fur-3-yl; $R_3$ is H; $R_4$ is 5-methoxy; $R_5$ is H; and Y is O;
a compound of Formula (I) wherein G is 2-methylcarbonylamino-phenyl; $R_3$ is H; $R_4$ is 5-methoxy; $R_5$ is H; and Y is O;
a compound of Formula (I) wherein G is quinolin-3-yl; $R_3$ is H; $R_4$ is 5-hydroxy; $R_5$ is H; and Y is O;
a compound of Formula (I) wherein G is 2-methylcarbonylamino-phenyl; $R_3$ is H; $R_4$ is H; $R_5$ is H; and Y is S;
a compound of Formula (I) wherein G is pyridin-3-yl; $R_3$ is 1H-imidazol-2-ylmethyl; $R_4$ is H; $R_5$ is H; and Y is S;
a compound of Formula (I) wherein G is pyridin-3-yl; $R_3$ is fur-3-ylmethyl; $R_4$ is H; $R_5$ is H; and Y is S;
a compound of Formula (I) wherein G is pyridin-3-yl; $R_3$ is pyridin-2-ylmethyl; $R_4$ is H; $R_5$ is H; and Y is S;
a compound of Formula (I) wherein G is 2-methylcarbonylamino-phenyl; $R_3$ is fur-3-ylmethyl; $R_4$ is H; $R_5$ is H; and Y is S;
a compound of Formula (I) wherein G is 2-methylcarbonylamino-phenyl; $R_3$ is pyridin-2-ylmethyl; $R_4$ is H; $R_5$ is H; and Y is S;
a compound of Formula (I) wherein G is diethylamidino; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is 5-methoxy; $R_5$ is H; and Y is O;
a compound of Formula (I) wherein G is 4H-[1,2,4]-oxadiazol-5-thioxo-3-yl; $R_3$ is H; $R_4$ is 5-methoxy; $R_5$ is H; and Y is O; and
a compound of Formula (I) wherein G is 4H-[1,2,4]-oxadiazol-5-oxo-3-yl; $R_3$ is H; $R_4$ is 5-hydroxy; $R_5$ is H; and Y is O.

Another embodiment of the present invention is directed to compositions comprising a compound selected from the group consisting of:
a compound of Formula (I) wherein G is 1H-tetrazol-5-yl; $R_3$ is H; $R_4$ is H; $R_5$ is H; and Y is O;
a compound of Formula (I) wherein G is 2-methylcarbonylaminophenyl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;
a compound of Formula (I) wherein G is pyrrolidin-1-ylcarbonyl; $R_3$ is H; $R_4$ is H; $R_5$ is H; and Y is O;
a compound of Formula (I) wherein G is N-(2-methoxyethyl)-N-methyl-aminocarbonyl; $R_3$ is H; $R_4$ is H; $R_5$ is H; and Y is O;
a compound of Formula (I) wherein G is 4H-[1,2,4]thiadiazol-5-oxo-3-yl; $R_3$ is H; $R_4$ is H; $R_5$ is H; and Y is O;
a compound of Formula (I) wherein G is N,N-diethylamidino; $R_3$ is H; $R_4$ is H; $R_5$ is H; and Y is O;
a compound of Formula (I) wherein G is [1,2,3,5]oxathiadiazol-2-oxo-4-yl; $R_3$ is H; $R_4$ is H; $R_5$ is H; and Y is O;
a compound of Formula (I) wherein G is N-(3-fluorophenyl)-methyl-aminocarbonyl; $R_3$ is H; $R_4$ is H; $R_5$ is H; and Y is O;
a compound of Formula (I) wherein G is pyridin-3-yl; $R_3$ is H; $R_4$ is H; $R_5$ is H; and Y is O;
a compound of Formula (I) wherein G is N-[2-(2,6-dimethylphenoxy)-1-methyl-ethyl]aminocarbonyl; $R_3$ is H; $R_4$ is H; $R_5$ is H; and Y is O;
a compound of Formula (I) wherein G is N-phenyl-N-methyl-aminocarbonyl; $R_3$ is H; $R_4$ is H; $R_5$ is H; and Y is O;
a compound of Formula (I) wherein G is N-(1(S)-hydroxymethyl-2-phenyl-eth-1-yl)aminocarbonyl; $R_3$ is H; $R_4$ is H; $R_5$ is H; and Y is O;
a compound of Formula (I) wherein G is 2-methyl-tetrazol-5-yl; $R_3$ is H; $R_4$ is H; $R_5$ is H; and Y is O;
a compound of Formula (I) wherein G is N-(2-phenylethyl)-N-methyl-aminocarbonyl; $R_3$ is H; $R_4$ is H; $R_5$ is H; and Y is O;
a compound of Formula (I) wherein G is 2-aminocarbonylphenyl; $R_3$ is H; $R_4$ is H; $R_5$ is H; and Y is O;
a compound of Formula (I) wherein G is 2-phenylethyl-aminocarbonyl; $R_3$ is H; $R_4$ is H; $R_5$ is H; and Y is O;
a compound of Formula (I) wherein G is 3-methylcarbonylamino-phenyl; $R_3$ is H; $R_4$ is H; $R_5$ is H; and Y is O;
a compound of Formula (I) wherein G is N-(2-dimethylamino-eth-1-yl)-N-methyl-aminocarbonyl; $R_3$ is ethoxycarbonyl; $R_4$ is H; $R_5$ is H; and Y is O;
a compound of Formula (I) wherein G is N-(dimethylaminocarbonylmethyl)-N-methyl-aminocarbonyl; $R_3$ is H; $R_4$ is H; $R_5$ is H; and Y is O; a compound of Formula (I) wherein G is pyridin-3-yl; $R_3$ is H; $R_4$ is 5-methoxy; $R_5$ is H; and Y is O;
a compound of Formula (I) wherein G is 1H-tetrazol-5-yl; $R_3$ is H; $R_4$ is H; $R_5$ is H; and Y is O;
a compound of Formula (I) wherein G is 1H-tetrazol-5-yl; $R_3$ is H; $R_4$ is 5-methoxy; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-oxo-3-yl; $R_3$ is H; $R_4$ is H; $R_5$ is H; and Y is O;
a compound of Formula (I) wherein G is 4H-[1,2,4]-oxadiazol-5-thioxo-3-yl; $R_3$ is H; $R_4$ is H; $R_5$ is H; and Y is O;

a compound of Formula (I) wherein G is 4H-[1,2,4]-oxadiazol-5-thioxo-3-yl; $R_3$ is H; $R_4$ is H; $R_5$ is H; and Y is O;

a compound of Formula (I) wherein G is 4H-[1,2,4]thiadiazol-5-oxo-3-yl; $R_3$ is H; $R_4$ is H; $R_5$ is H; and Y is O;

a compound of Formula (I) wherein G is 1H-tetrazol-5-yl; $R_3$ is H; $R_4$ Is H; $R_5$ is H; and Y is S;

a compound of Formula (I) wherein G is 1H-tetrazol-5-yl; $R_3$ is H; $R_4$ is H; $R_5$ is H; and Y is S;

a compound of Formula (I) wherein G is 2-methylcarbonylamino-phenyl; $R_3$ is H; $R_4$ is 5-methoxy; $R_5$ is H; and Y is O;

a compound of Formula (I) wherein G is quinolin-3-yl; $R_3$ is H; $R_4$ is 5-hydroxy; $R_5$ is H; and Y is O;

a compound of Formula (I) wherein G is 2-methylcarbonylamino-phenyl; $R_3$ is pyridin-2-ylmethyl; $R_4$ is H; $R_5$ is H; and Y is S;

a compound of Formula (I) wherein G is N,N-diethylamidino; $R_3$ is H; $R_4$ is H; $R_5$ is H; and Y is O;

a compound of Formula (I) wherein G is 4H-[1,2,4]-oxadiazol-5-oxo-3-yl; $R_3$ is H; $R_4$ is 5-methoxy; $R_5$ is H; and Y is O;

a compound of Formula (I) wherein G is 4H-[1,2,4]-oxadiazol-5-thioxo-3-yl; $R_3$ is H; $R_4$ is 5-methoxy; $R_5$ is H; and Y is O; and a compound of Formula (I) wherein G is 4H-[1,2,4]-oxadiazol-5-oxo-3-yl; $R_3$ is H; $R_4$ is 5-hydroxy; $R_5$ is H; and Y is O.

Another embodiment of the present invention is directed to compositions comprising a compound selected from the group consisting of:

a compound of Formula (Ib) wherein G is carboxy; $R_3$ is H; $R_4$ is H; $R_5$ is H; and Y is O;

a compound of Formula (Ib) wherein G is methoxycarbonyl; $R_3$ is H; $R_4$ is H; $R_5$ is H; and Y is O;

a compound of Formula (Ib) wherein G is methoxycarbonyl; $R_3$ is ethoxycarbonyl; $R_4$ is H; $R_5$ is H; and Y is O;

a compound of Formula (Ib) wherein G is methoxycarbonyl; $R_3$ is H; $R_4$ is H; $R_5$ is H; and Y is S;

a compound of Formula (Ib) wherein G is cyano; $R_3$ is H; $R_4$ is H; $R_5$ is H; and Y is O;

a compound of Formula (Ib) wherein G is methoxycarbonyl; $R_3$ is H; $R_4$ is 6-methoxycarbonyl; $R_5$ is H; and Y is O;

a compound of Formula (Ib) wherein G is bromo; $R_3$ is H; $R_4$ is 5-methoxy; $R_5$ is H; and Y is O;

a compound of Formula (Ib) wherein G is bromo; $R_3$ is H; $R_4$ is H; $R_5$ is H; and Y is S;

a compound of Formula (Ib) wherein G is cyano; $R_3$ is H; $R_4$ is H; $R_5$ is H; and Y is S;

a compound of Formula (Ib) wherein G is cyano; $R_3$ is H; $R_4$ is H; $R_5$ is H; and Y is O;

a compound of Formula (Ib) wherein G is cyano; $R_3$ is H; $R_4$ is H; $R_5$ is H; and Y is O;

a compound of Formula (Ib) wherein G is cyano; $R_3$ is trifluoromethylcarbonyl; $R_4$ is H; $R_5$ is H; and Y is O;

a compound of Formula (Ib) wherein G is cyano; $R_3$ is trifluoromethylcarbonyl; $R_4$ is H; $R_5$ is H; and Y is O;

a compound of Formula (Ib) wherein G is carboxy; $R_3$ is t-butoxycarbonyl; $R_4$ is H; $R_5$ is H; and Y is O;

a compound of Formula (Ib) wherein G is carboxy; $R_3$ is H; $R_4$ is H; $R_5$ is H; and Y is O; and a compound of Formula (Ib) wherein G is carboxy; $R_3$ is H; $R_4$ is H; $R_5$ is H; and Y is O.

Another embodiment of the present invention is a composition comprising the dextrorotatory enantiomer of a compound of formula (I), wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to severe pain in warm-blooded animals such as humans by administration of an analgesically effective dose. The dosage range would be from about 0.1 mg to about 15,000 mg, in particular from about 50 mg to about 3500 mg or, more particularly from about 100 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the disases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

The preparation of compounds of this invention is illustrated in Schemes 1 and 2. Both schemes proceed with the same overall strategy. In stage 1, an intermediate 1 is prepared with two benzene rings connected by a linker —Y—. The linker —Y— should be of the form —$(CH_2)_n$—X— where X may be oxygen or sulfur and n may be zero or one. One benzene ring bears a group, Q, which is a group readily transformable to a substituent G as defined herein. Examples of such Q groups are fluoro, bromo, cyano, iodo, carboxy, or trifluoromethanesulfonyloxy. In some instances, the 0 substituents may be the same as the G substituents of Formula (Ib). One benzene ring must bear a carboxylic acid, or a precursor to a carboxylic acid, positioned ortho to the linker —Y—. The atom X may be attached either to the benzene ring bearing the Q group or the benzene ring lacking the Q group. Schemes 1 and 2 differ in that in scheme 1, the carboxylic acid is on the benzene ring bearing the Q group (1A and 1B) while in scheme 2 the carboxylic acid function is on the benzene ring which does not bear the group Q (1C, 1D and 1E).

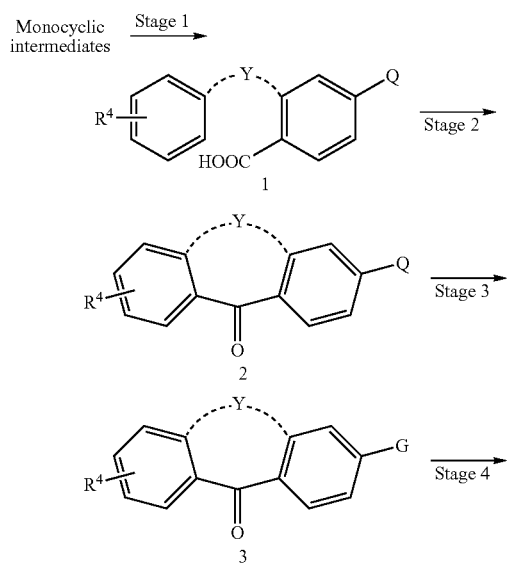

Scheme 1

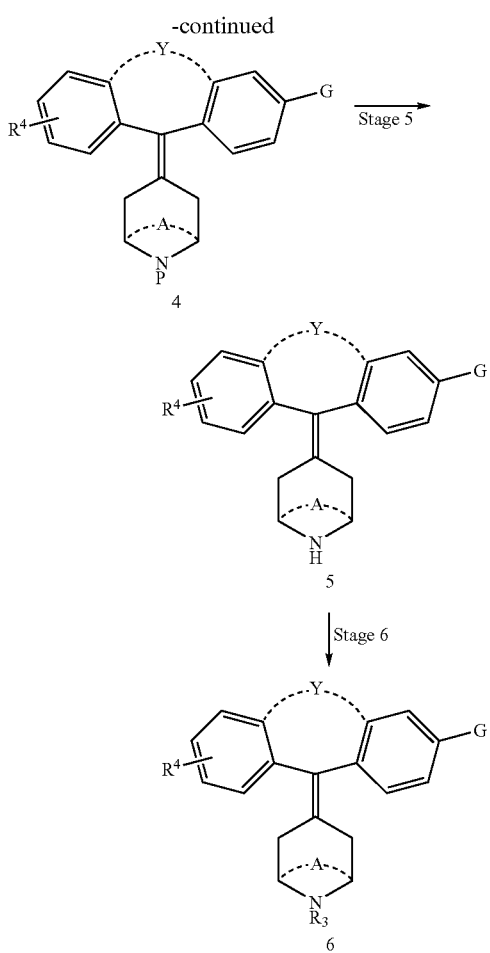

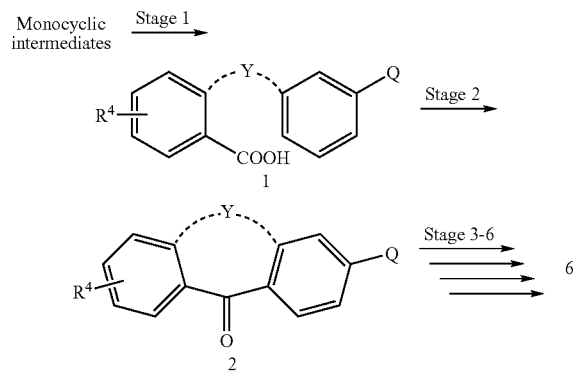

In stage 1 the linker —Y— is constructed between two monocyclic intermediates. For Scheme 1, Stage 1, the bridge may be constructed by nucleophilic aromatic displacement of fluoride from intermediate int 2 (where Q' is an electron withdrawing group, readily convertible to a carboxylic acid, for instance cyano or carbalkoxy) by a phenoxide, thiophenoxide, benzyloxide or benzylthiooxide, int 1. The 1A compounds are then obtained by hydrolysis with an alkali metal hydroxide. For construction of the bridge of compounds of type 1B, a benzyl halide intermediate compound (int 5) is prepared by NBS bromination of the corresponding toluene (int 4). Reaction of int 5 with a phenoxide or phenylthiooxide leads to int 6. The 1B compound may be obtained by alkali metal hydroxide hydrolysis of int 6.

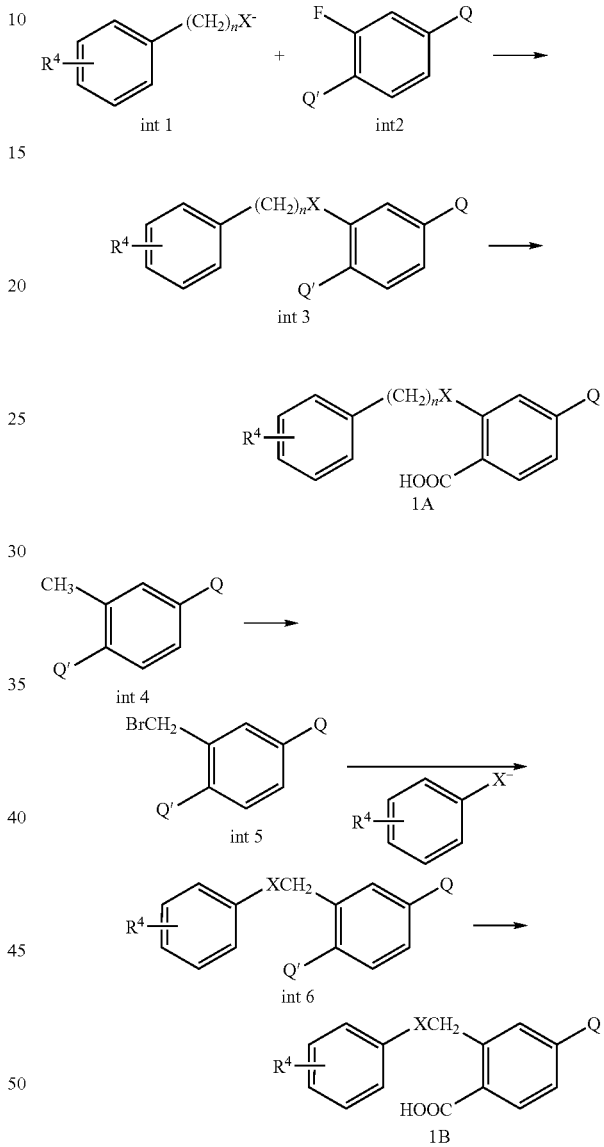

For Scheme 2, Stage 1, in order to prepare 1C compounds, a phthalide (int 7) may be caused to react with a phenoxide or phenylthiooxide (int 8). For preparation of compounds of formula 1D, the bridge may be constructed by nucleophilic aromatic displacement of fluoride from intermediate int 9 by phenoxides or phenylthiooxides (int 8). The compounds of formula 1D are then obtained by hydrolysis of int 10 with an alkali metal hydroxide. For construction of the Y-linker of compounds of intermediate 13, benzyl bromide compounds of int 12 may be reacted with a phenoxide or phenylthiooxide (int 11). The compounds of formula 1E may then be obtained by hydrolysis of int 13 with an alkali metal hydroxide.

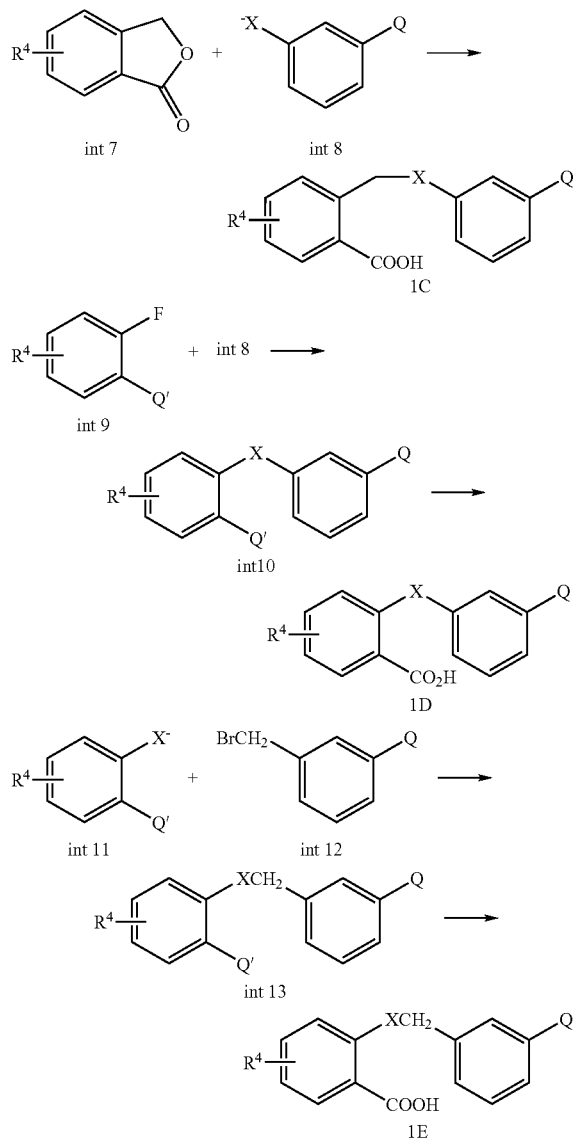

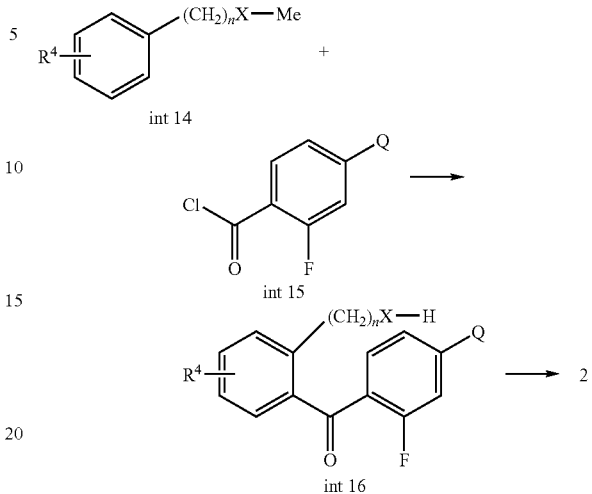

Following Stage 1, the schemes merge. In Stage 2, compounds of formula 1 are converted by cycloacylation to ketones of formula 2, using, for instance, $BF_3Et_2O$-trifluoroacetic acid or polyphosphoric acid. Alternatively, the cyclization may be effected by converting an acid of formula 1 to an acid chloride using a chlorinating agent such as thionyl chloride or the like, followed by Friedel-Crafts ring closure in the presence of a Lewis acid, such as aluminum chloride.

In addition, Stages 1 and 2 may be performed in reverse order to give compounds of formula 2 that are ready to enter Stage 3. For instance, Friedel-Crafts acylation between a methyl ether (int 14) and an appropriately substituted acid chloride provides the ketone (int 16), which is simultaneously demethylated under the reaction conditions. Subsequent formation of the bridge —Y— via a nucleophilic aromatic displacement gives compounds of formula 2 that are ready to enter Stage 3.

In stage 3, the Q function of compounds of formula 2 is converted into group G, which may be $—C(Z)NR_1R_2$, an aryl substituent, an aryl thioether, or an appropriate heterocycle as defined herein, to give compounds of formula 3. When the Q function of compounds of formula 2 is a halogen or trifluoromethanesulfonyloxy, it may be converted to an an ester via alkoxycarbonylation using carbon monoxide, an aliphatic alcohol, a trialkanyl amine, and a palladium catalyst such as bis(triphenylphosphine) palladium(II)dichloride. Subsequently, when Q is an ester, the ester may be hydrolyzed to a carboxylic acid. The carboxylic acid may then be coupled with an appropriately functionalized amine to form a primary, secondary or tertiary amide. Alternatively, the conversion of a carboxylic acid to an amide may be carried out via an acid chloride using thionyl chloride, oxalyl chloride, or the like, followed by a Schotten-Baumann reaction using an appropriately functionalized amine in the presence of an alkali metal hydroxide. Alternatively, the ester may be converted directly to the amide by the action of a dimethylaluminum amide.

Instead of proceeding to compounds of formula 3 via an ester, one may effect the transformation of the group Q to a substituent G (wherein G is an amidino or heterocycle) by way of a nitrile. Synthesis of the nitrile may be accomplished by treatment of the compounds of formula 2 (when Q is bromo or trifluoromethanesulfonyloxy) with $Zn(CN)_2$ and a palladium catalyst such as $(Ph_3P)_4Pd$ or by treatment of the compounds of formula 2 with CuCN at elevated temperatures. For the synthesis of amidino functional groups, the nitrile is treated with hydroxylamine under basic conditions to afford an oxime. Treatment of the oxime with a primary or secondary amine, CuCl, and an alkali metal carbonate under microwave irradiation in an alcoholic solvent provides the amidino compounds of the present invention. Microwave accelerated reactions may be performed using either a CEM Discover or a Personal Chemistry Smith Synthesizer microwave instrument. The oxime described above is instrumental in the preparation of compounds wherein G is a heterocycle. The oxime may be cyclized with a variety of electrophiles known to one versed in the art to give the heterocycles of the present invention. For instance, reaction of an oxime with CDI provides oxadiazolones, and treatment of the oxime with TCDI provides the corresponding oxadiazolethiones. Similarly, the treatment of the oxime with thionyl chloride in the presence of a tertiary amine gives oxathiadiazoles of the present invention.

An aryl substituent may be installed in place of the functional group Q by coupling compounds of formula 2 (when Q is bromo or trifluoromethanesulfonyloxy) with a suitably substituted arylboronic acid in the presence of a palladium catalyst and an alkali metal carbonate.

To perform stage 4, an A-substituted ring is is attached to the tricyclic system, replacing the ketone to give compounds of formula 4 wherein m is 0, 2, or 3, as defined herein. This operation may be carried out by McMurray condensation of ketones of formula 3 with 4-piperidinones (m is 0) or 8-nortropinones (m is 2) or an azabicyclo(3.3.1)nonanone (m is 3), in the presence of a lower valent titanium reagent. Such a reagent may be formed from the addition of titanium tetrachloride to zinc dust. Alternatively, an appropriately substituted magnesium halide may be added to ketones of formula 3 to afford carbinols. Dehydration of such carbinols with acidic reagents such as formic acid, sulfuric acid or trifluoroacetic acid also gives rise to compounds of formula 4. If desired, the operation of stages 3 and 4 may be carried out in reverse order.

As illustrated in Schemes 1 and 2, the nitrogen atoms of compounds of formula 4 may bear a group P. This group may be an alkanyl, alkenyl or aralkanyl in which case they are the therapeutically useful products of this invention. The group P may also be trifluoromethylcarbonyl, alkoxycarbonyl or aralkoxycarbonyl. The latter groupings can be converted to secondary amines of formula 5 as illustrated in Stage 5. These transformations may be carried out using certain acidic reagents such as hydrogen bromide or trimethylsilyl iodide. Or, when P is a trifluoromethylcarbonyl, basic reagents such as potassium carbonate in an alcoholic solvent may be used for the removal of P. Compounds of formula 4 bearing readily cleavable groups such as methyl, allyl or benzyl may be transformed into the aforementioned alkoxycarbonyl derivatives by treatment with alkanylchloro-formates such as ethyl chloroformate or 1-chloroethyl chloroformate.

Finally, the secondary amines of formula 5 may be substituted with $R_3$ to provide compounds of formula 6, shown in Stage 6. These transformations may be carried out by reductive alkylation using a carbonyl-containing compound and a reducing agent such as sodium borohydride, sodium cyanoborohydride, tetramethylammonium triacetoxyborohydride, or sodium triacetoxyborohydride. Substituent $R_3$ may also be installed via a conventional alkyation, using an alkanyl, alkenyl or aralkyl halide and an organic or inorganic base. One skilled in the art will recognize that alkylating agents with leaving groups other than halide are equally useful for this transformation.

Desired end products of the present invention may include chemical modifications at $R_4$. Such transformations may include the dealkylation of lower alkyl ethers to give their corresponding alcohols, using reagents such as boron trihalides. Compounds where $R_4$ is a halogen atom may participate in transition metal-mediated coupling reactions such as Suzuki, Stille or Negishi chemistry.

Scheme 4 demonstrates the preparation of compounds of the present invention wherein $R_4$ is other than hydroxy or mercapto. A compound of formula int 17 can be converted to its triflate by treatment with N,N-bis(trifluoromethylsulfonyl)phenylamine or similar reagents to afford a compound of formula int 18. Treatment of the triflate with a cyanide source such as zinc cyanide in the presence of a palladium catalyst provides compounds of formula int 19, which subsequently can be hydrolyzed with hydroxide anion in the presence of hydrogen peroxide to afford compounds of formula int 20 wherein $R_4$ is an aminocarbonyl.

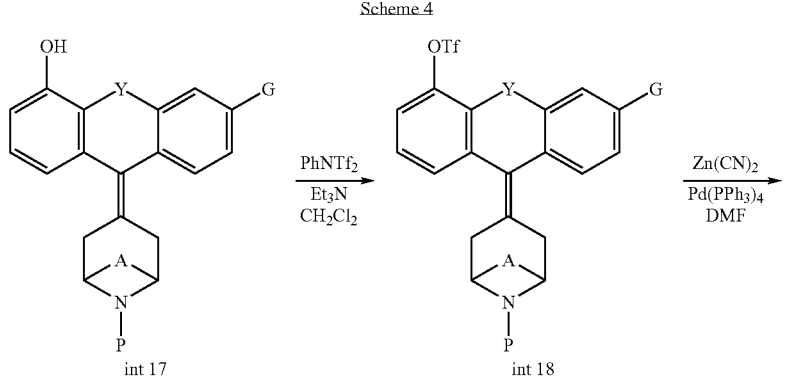

Scheme 4

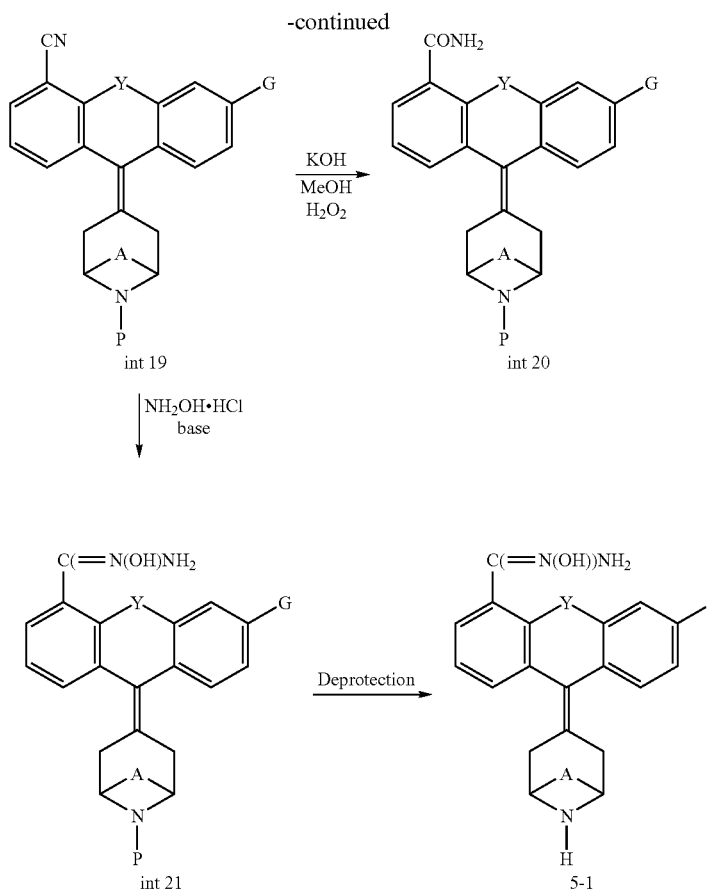

The cyano group of a compound of formula int 19 is also a precursor to other $R_4$ substituents of the present invention. For example, a compound of formula int 19 may be treated with ammonium hydroxide in the presence of a base such as a tertiary amine to afford a hydroxyamidino compound of formula int 21. Deprotection of compounds of formula int 21 affords compounds of formula 5-1.

As illustrated in Scheme 5, a compound of formula int 18 may be treated with an amino synthon, where a synthon is a synthetic equivalent or a functional group that is related to some other structural unit by a reliable reaction or sequence of reactions. An example of an amino group synthon includes, but is not limited to, benzophenone imine. Benzophenone imine may be used in the presence of an appropriate palladium catalyst under basic conditions, which upon treatment with ammonium hydroxide, affords compounds of formula int 22. The aniline may be formylated with acetic formic anhydride followed by removal of P using methods discussed herein. Lawesson's reagent may be used to convert carbonyl-containing $R_4$ substituents to their corresponding thiocarbonyl analogs.

Scheme 5

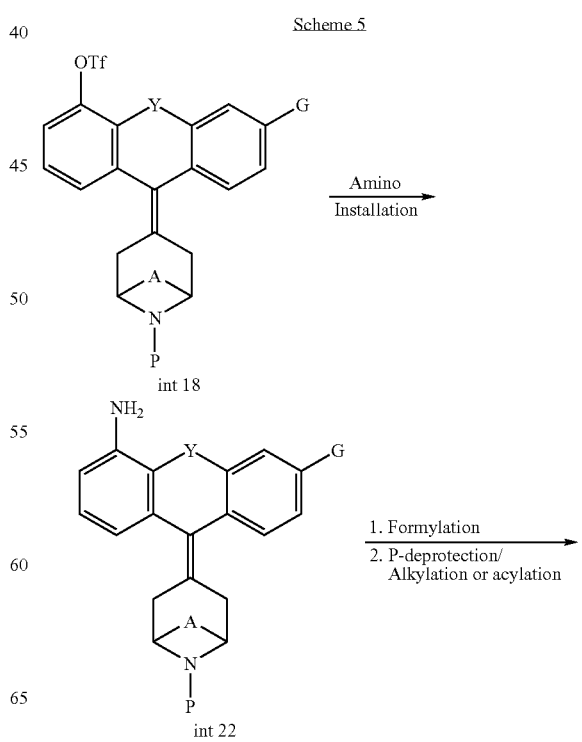

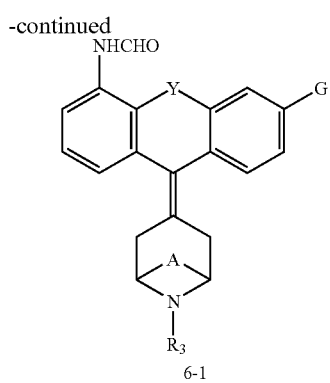

The preparation of compounds wherein $R_4$ is $C_{6-10}$arylamino may be achieved using a palladium catalyzed amination of a compound of formula int 18 with $C_{6-10}$arylamine and an inorganic base, such as cesium carbonate.

Anilines of formula int 22 may be converted to the corresponding aminothiazoles of formula 6-2 via reaction with appropriate reagents such as potassium thiocyanate.

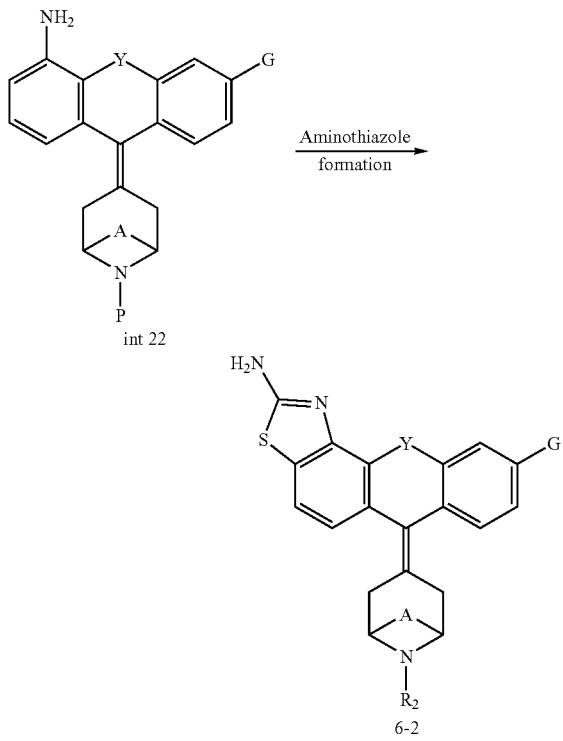

The compounds wherein the bridge -A- is —(CH$_2$)$_{2-3}$— are chiral. They may be separated into their enantiomers by chromatography on a chiral stationary phase following Stages 4, 5, or 6. Alternatively, the basic compounds of formulae 4, 5, and 6 may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

| Abbreviations | |
|---|---|
| CDI = | 1,1'-carbonyldiimidazole |
| DBN = | 1,8-diazabicyclo[5.4.0]undec-7-ene |
| DMF = | N,N-dimethylformamide |
| dppf = | 1,1'-bis(diphenylphosphino)ferrocene |
| Et = | ethyl |
| h = | hour(s) |
| Me = | methyl |
| min = | minute(s) |
| TCDI = | 1,1'-thiocarbonyldiimidazole |
| PPA = | polyphosphoric acid |
| t-Boc = | tert-butoxycarbonyl |
| TCDI = | 1,1'-thiocarbonyldiimidazole |
| TFA = | trifluoroacetic acid |
| THF = | tetrahydrofuran |
| μW = | microwave irradiation |
| W = | watt(s) |

EXAMPLES

Example 1

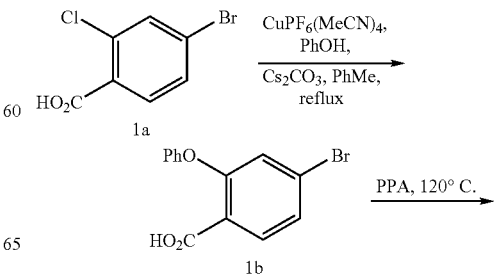

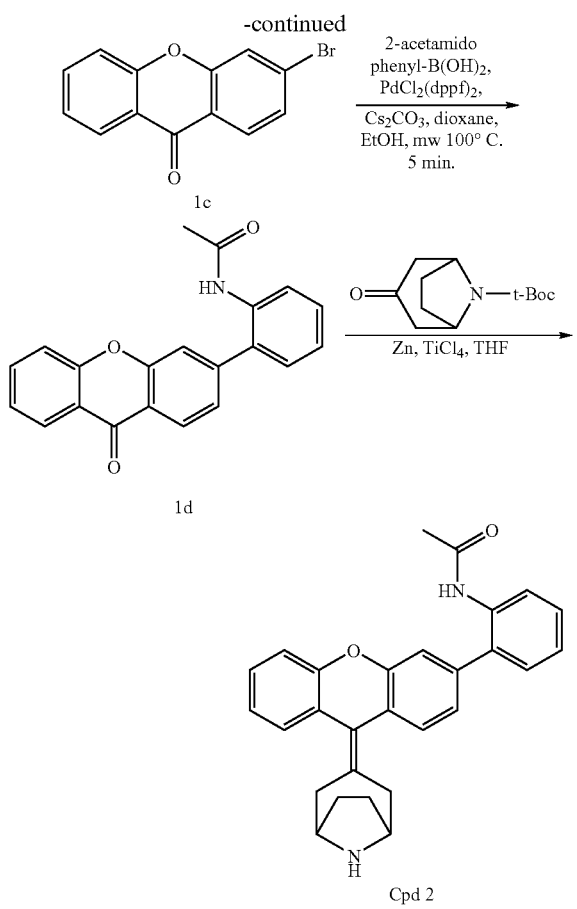

Procedure C

N-[2-(9-Oxo-9H-xanthen-3-yl)-phenyl]-acetamide (1d). 3-Bromo-xanthen-9-one (0.25 g, 0.9 mmol), 2-acetamidophenylboronic acid (0.99 mmol), 1,1'-bis-(diphenylphosphino)ferrocene-palladium (II) dichloride (33 mg, 0.045 mmol), cesium carbonate (0.59 g, 1.8 mmol), dioxane (4 mL), and ethanol (2 mL) were microwaved in a 5-mL reaction vessel at 100° C. for 5 min. The reaction was filtered and concentrated. The residue was purified by reverse phase chromatography to afford N-[2-(9-Oxo-9H-xanthen-3-yl)-phenyl]-acetamide.

Procedure D

N-{2-[9-(8-Aza-bicyclo[3.2.1]oct-3-ylidene)-9H-xanthen-3-yl]-phenyl}-aceta-mide (Cpd 2). A suspension of zinc powder (0.317 g, 4.8 mmol) in THF (100 mL) at ambient temperature was treated with titanium(IV)chloride (0.266 mL, 2.4 mmol) by dropwise addition. The resultant mixture was heated at reflux for 2 h under a nitrogen atmosphere. The resultant solution was cooled to room temperature. A portion of 3-oxo-8-aza-bicyclo[3.2.1]octane-8-carboxylic acid tert-butyl ester (0.136 g, 0.6 mmol) and N-[2-(9-oxo-9H-xanthen-3-yl)-phenyl]-acetamide (0.20 g, 0.6 mmol) were added and the solution was heated at reflux for 2 h. The reaction was diluted with ethyl acetate (15 mL) and aqueous 1 N hydrochloric acid (20 mL). The organic layer was separated, dried (MgSO$_4$), and filtered. The filtrate was evaporated in vacuo. The crude product was purified by reverse phase preparative HPLC, using a gradient of acetonitrile (10% to 90%) in water with trifluoroacetic acid (0.1%), to give the trifluoroacetic acid salt of Compound 2 (0.124 g). MS m/z (MH$^+$) 423.2; $^1$H NMR (DMSO-d$_6$) δ 1.32 (m, 2H), 1.79 (m, 2H), 1.88 (s, 3H), 2.92-3.0 (m, 4H), 4.04 (m, 2H), 7.21-7.47 (m, 11H), 8.67 (bs, 1H), 9.05 (d, 1H), 9.35 (s, 1H).

Procedure A

4-Bromo-2-phenoxybenzoic acid (1b). 4-Bromo-2-chloro-benzoic acid (10 g, 42 mmol), phenol (4.19 g, 44 mmol), tetrakisacetonitrilecopper hexafluorophosphate (3.95 g, 10.6 mmol), and cesium carbonate (27.6 g, 85 mmol) were added to a 1 L 3-neck round bottom flask equipped with a mechanical stirrer, reflux condenser, and containing toluene (350 mL). The reaction was refluxed overnight under nitrogen with stirring. After cooling, ethyl acetate (200 mL) was added and the reaction was acidified with aqueous 2N HCl. The organic phase was separated, dried (MgSO$_4$), and filtered. The filtrate was concentrated to afford 4-bromo-2-phenoxybenzoic acid (12.4 g) that was used in subsequent reactions without further purification.

Procedure B

3-Bromo-xanthen-9-one (1c). Polyphosphoric acid (260 g, 20:1; w:w) was added to 4-bromo-2-phenoxybenzoic acid (13.5 g). The reaction was heated (120° C.) while being stirred briskly with a mechanical stirrer to achieve homogeneity. After 2 h, the heating apparatus was removed. Once the reaction temperature was below 70° C., the mixture was poured over crushed ice. The resulting aqueous solution was extracted with chloroform (3×100 mL). The combined organic extracts were washed with sodium bicarbonate solution (100 mL, 1 M), dried (MgSO$_4$), and concentrated to afford 3-bromo-xanthen-9-one (11.4 g) that was used in subsequent reactions without further purification.

Example 2

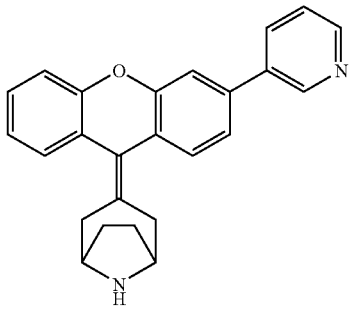

3-(3-Pyridin-3-yl-xanthen-9-ylidene)-8-aza-bicyclo[3.2.1]octane (Cpd 12). The title compound was prepared using the method described in Example 1, substituting 3-pyridylboronic acid for 2-acetamidophenylboronic acid in Procedure C and using an adaptation of Procedure D. MS m/z (MH$^+$) 367.1; $^1$H NMR (DMSO-d$_6$) δ 1.29 (d, 2H, J=9.2 Hz), 1.78 (m, 2H), 2.91-3.09 (m, 4H), 4.01 (s, 2H), 7.24 (t, 1H, J=7.4 Hz), 7.31 (d, 1H, J=6.8 Hz), 7.38 (d, 1H, J=7.0 Hz), 7.43 (d, 1H, J=7.7 Hz), 7.54 (d, 1H, J=8.0 Hz), 7.62-7.73 (m, 2H), 7.73 (s, 1H), 8.32 (d, 1H, J=8.0 Hz), 8.68 (m, 1H), 8.81 (m, 1H), 9.05 (s, 1H), 9.11 (m, 1H).

Example 3

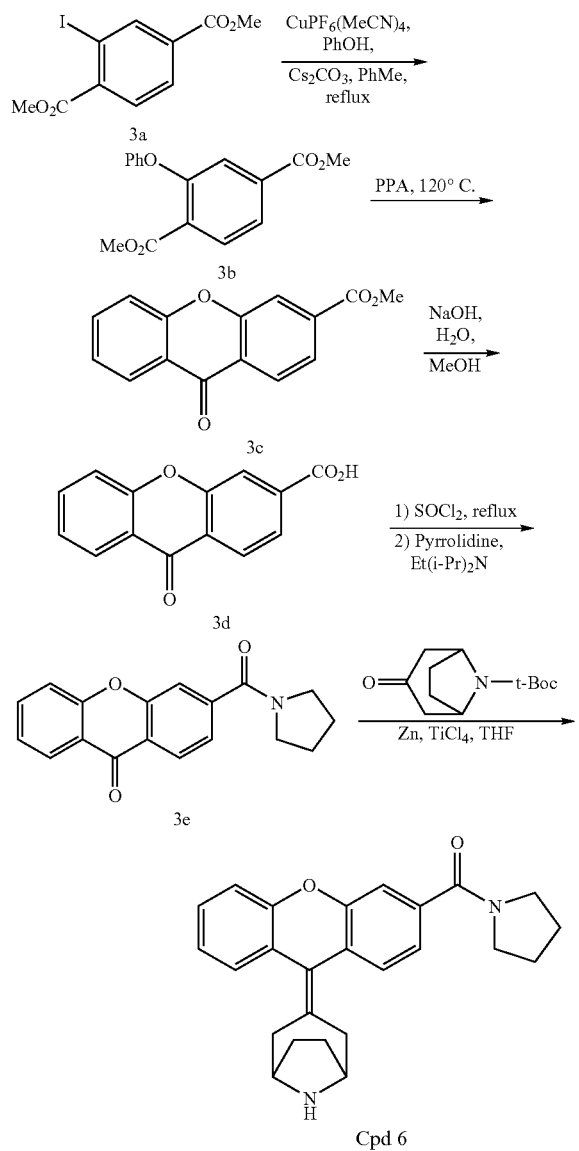

2-Phenoxy-terephthalic acid dimethyl ester (3b). The title compound was prepared according to the method described in Procedure A and substituting 2-iodo-terephthalic acid dimethyl ester for 4-bromo-2-chloro-benzoic acid.

9-Oxo-9H-xanthene-3-carboxylic acid methyl ester (3c). The title compound was prepared according to the method described in Procedure B, substituting 2-phenoxy-terephthalic acid dimethyl ester for 4-bromo-2-phenoxybenzoic acid.

Procedure E

9-Oxo-9H-xanthene-3-carboxylic acid (3d). A solution of 9-oxo-9H-xanthene-3-carboxylic acid methyl ester (3.75 mmol) and 3 N sodium hydroxide (4.12 mmol) in MeOH (30 mL) was heated at reflux for 2 h. The solution was cooled to rt and made acidic with 2 N hydrochloric acid. The mixture was concentrated in vacuo, and then diluted with water. The resultant solid was collected by filtration, washed with water and air-dried to yield the title compound.

Procedure F 3-(Pyrrolidine-1-carbonyl)-xanthen-9-one (3e). 9-oxo-9H-xanthene-3-carboxylic acid (9 g, 37.4 mmol) was added to thionyl chloride (28 mL, 334 mmol). The mixture was refluxed for 5 h. At that time, the thionyl chloride was removed under vacuum and the remaining residue was diluted with toluene and concentrated to dryness to give 9-oxo-9H-xanthene-3-carbonyl chloride. A portion of 9-oxo-9H-xanthene-3-carbonyl chloride (0.25 g, 0.96 mmol) was dissolved in acetonitrile (7 mL). Diisopropylethylamine (335 µL, 1.9 mmol) was then added to the mixture with the subsequent addition of pyrrolidine (113 µL, 1.3 mmol). After stirring 2 h, the solvent was concentrated and the residue was purified by reverse phase preparative HPLC, using a gradient of acetonitrile (10%- 90%) in water with trifluoroacetic acid (0.1%) to afford the 3-(pyrrolidine-1-carbonyl)-xanthen-9-one. MS m/z (MH$^+$) 294.1.

[9-(8-Aza-bicyclo[3.2.1]oct-3-ylidene)-9H-xanthen-3-yl]-pyrrolidin-1-yl-methanone (Cpd 6). The title compound was prepared according to Procedure D, substituting 3-(pyrrolidine-1-carbonyl)-xanthen-9-one for N-[2-(9-oxo-9H-xanthen-3-yl)-phenyl]-acetamide and obtained as a TFA salt after reverse phase preparative HPLC. MS m/z (MH$^+$) 387.2; $^1$H NMR (DMSO-$d_6$) δ 1.28 (d, 2H, J=11.2 Hz), 1.80-1.89 (m, 6H), 2.95 (q, 4H, J=16.1 Hz), 3.41 (t, 2H, J=6.2 Hz), 3.47 (t, 2H, J=6.8 Hz), 4.0 (s, 2H), 7.23 (t, 1H, J=7.3 Hz), 7.28-7.46 (m, 6H), 8.80 (bs, 1 H), 9.11 (m, 1 H).

Example 4

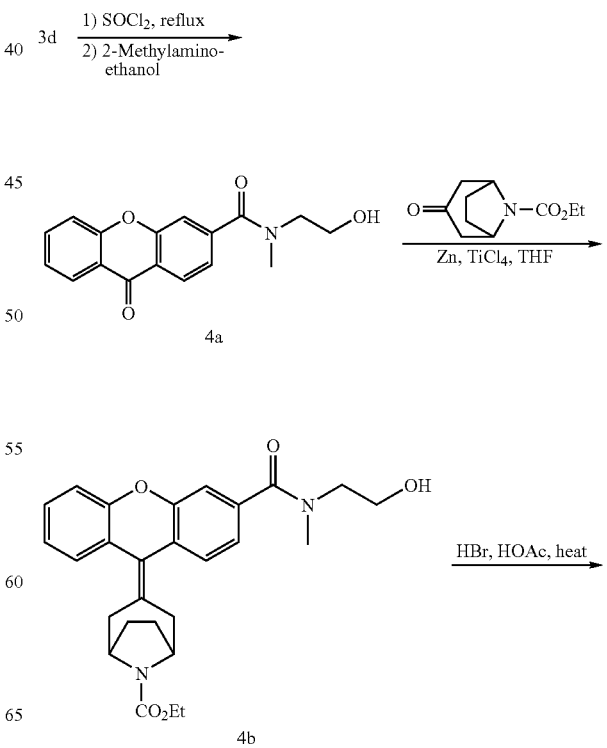

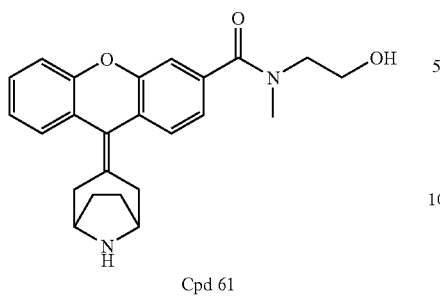

Cpd 61

9-Oxo-9H-xanthene-3-carboxylic acid (2-hydroxy-ethyl)-methyl-amide (4a). Using the method described in Procedure F, substituting 2-methylamino-ethanol for pyrrolidine, the title compound 4a was prepared.

3-{3-[(2-Hydroxyethyl)-methyl-carbamoyl]-xanthen-9-ylidene}-8-aza-bicyclo[3.2.1]octane-8-carboxylic acid ethyl ester (4b). Using the method described in Procedure D, substituting 9-Oxo-9H-xanthene-3-carboxylic acid (2-hydroxy-ethyl)-methyl-amide for N-[2-(9-oxo-9H-xanthen-3-yl)-phenyl]-acetamide and substituting 3-oxo-8-aza-bicyclo[3.2.1]octane-8-carboxylic acid ethyl ester for 3-oxo-8-aza-bicyclo[3.2.1]octane-8-carboxylic acid tert-butyl ester, the desired product 4b was prepared.

Procedure G 9-(8-Aza-bicyclo[3.2.1]oct-3-ylidene)-9H-xanthene-3-carboxylic acid (2-hydroxy-ethyl)-methyl-amide (Cpd 61). A sample of compound 4b (0.20 g, 0.43 mmol) was dissolved in 1 mL acetic acid and 2 mL of 30% HBr in acetic acid was added to the reaction under Argon before heating at 80° C. for 1 h. The reaction was cooled, added to ice cold NaOH and extracted with CHCl₃. The combined organic phases were concentrated. The resulting residue was purified by reverse phase HPLC, using a gradient of acetonitrile (10% to 90%) in water with trifluoroacetic acid (0.1%) to give the trifluoroacetic acid salt of compound 61 (0.146 g). MS m/z (MH⁺) 391.0; ¹H NMR (DMSO-d₆) δ 1.26 (m, 2H), 2.93-3.04 (m, 6H), 3.28 (m, 1H), 3.49 (m, 2H), 3.61 (m, 1H), 4.00 (m, 3H), 7.21-7.42 (m, 1H, J=7.0 Hz), 8.65 (m, 1H), 9.05 (m, 1H).

Example 5

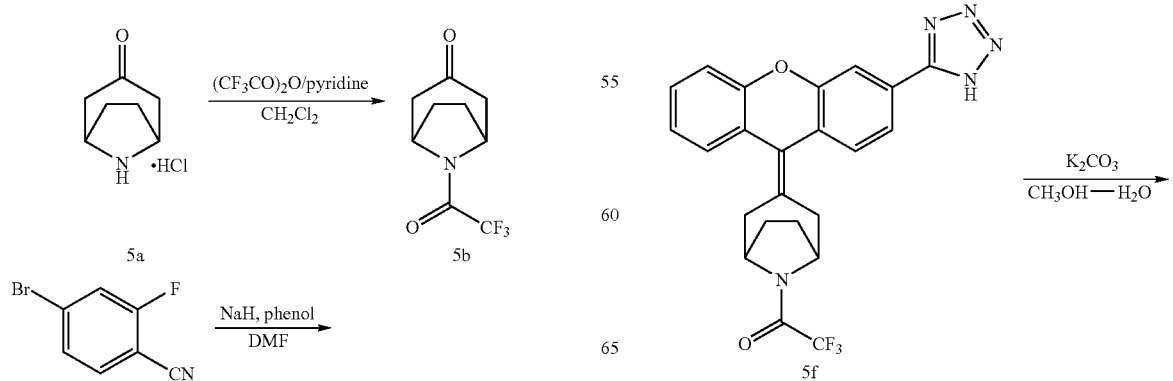

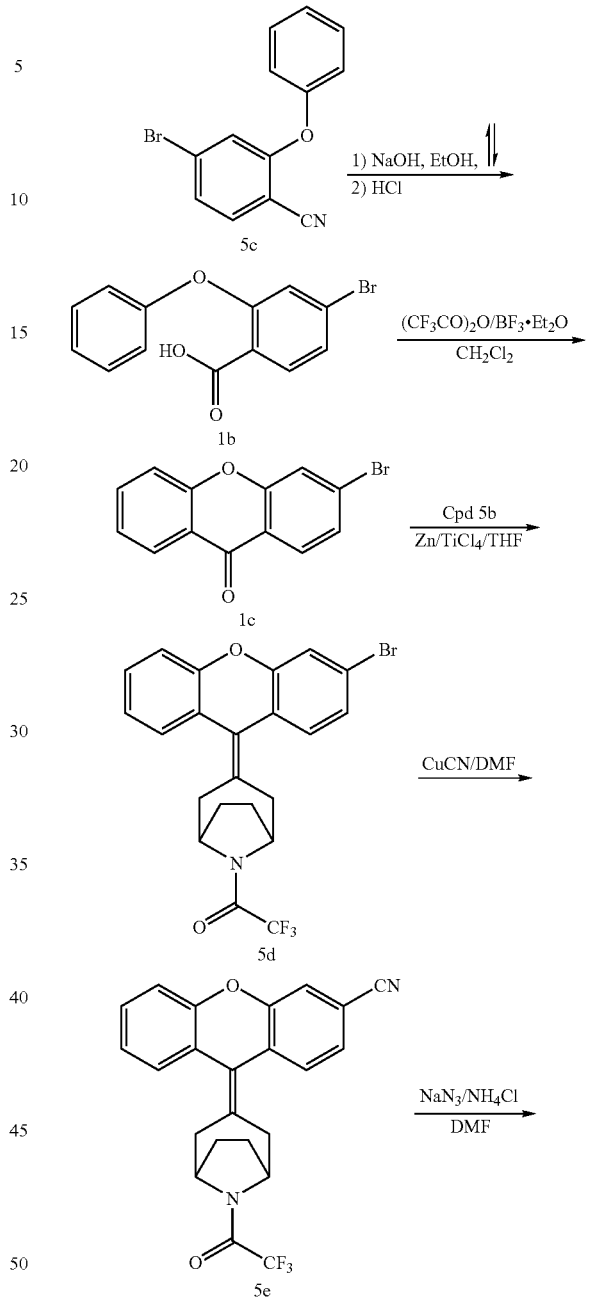

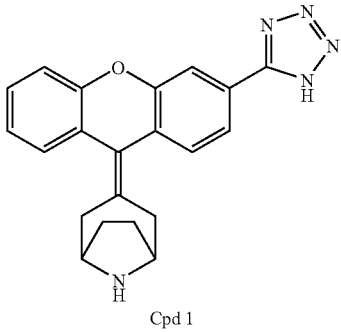

Cpd 1

Procedure H 8-(2,2,2-Trifluoroacetyl)-8-aza-bicyclo[3.2.1]octan-3-one (5b). To a solution of nortropinone hydrochloride (10 g, 61.87 mmol) and pyridine (20 mL, 247 mmol) in $CH_2Cl_2$ (120 mL) was added dropwise trifluoroacetic anhydride (12.4 mL, 87.79 mmol) at 0° C. The reaction mixture was stirred at 0° C. for 1 h and at room temperature for an additional 1 h. A portion of 2N HCl (65 mL) was added to the mixture. The organic phase was washed with brine, dried ($MgSO_4$), and concentrated. The crude compound 5b was used in the next reaction without further purification. MS m/z (MH+) 221.9; $^1$H NMR ($CDCl_3$) δ 1.78 (m, 1H), 1.90 (m, 1H), 2.19 (m, 2H), 2.49 (d, 2H), 2.72 (m, 2H), 4.71 (m, 1H), 4.99 (m, 1H).

Procedure I

4-Bromo-2-phenoxy-benzonitrile (5c). Sodium hydride (12 g, 300 mmol) (60% by wt) was weighed into a flask and washed free of oil with several hexane rinsings. The hexanes were decanted and discarded and DMF was added to the flask. A solution of phenol (23.5 g, 250 mmol) in DMF (100 mL) was added dropwise and the mixture was stirred at room temperature. To the mixture was added a solution of 4-bromo-2-fluoro-benzonitrile (50 g, 250 mmol, 100 mL DMF), dropwise. Upon complete addition, the reaction was refluxed for 20 h. The reaction was cooled to room temperature and poured into cold 1 N NaOH. A fine, tan precipitate formed and was collected by vacuum filtration to give Compound 5c. MS m/z (MH+) 277.

Procedure J

4-Bromo-2-phenoxy-benzoic acid (1 b). Compound 5c (35.3 g, 129 mmol) was added to 130 mL EtOH, followed by the addition of 340 mL of 20% aqueous NaOH. The reaction was heated to reflux for 20 h. At that time the mixture was cooled to room temperature and poured into 6 N HCl. The solid was collected by vacuum filtration, dissolved in 3:1 THF-ethyl ether, and washed with brine. The organic phase was dried ($MgSO_4$) and concentrated. The solids were dried in a vacuum oven at 60° C. overnight to give the desired compound 1b. MS m/z (MH+) 292.

Procedure K

3-Bromo-xanthen-9-one (1c). To a suspension of 4-bromo-2-phenoxy-benzoic acid (5 g, 17 mmol) in $CH_2Cl_2$ (50 mL) was added dropwise trifluoroacetic anhydride (2.9 mL, 20.53 mmol) at room temperature. The mixture was stirred at room temperature for 5 min. To this solution was added dropwise boron trifluoride diethyl etherate (0.215 mL, 1.7 mmol) at 0° C. After 30 min, the reaction was allowed to warm to room temperature. The mixture was stirred at room temperature for 2 h, at which time the mixture was poured into 1 N NaOH (35 mL) that was cooled to about 3° C. The aqueous layer was extracted with $CH_2Cl_2$ (2×10 mL). The combined organic layers were washed with brine, dried ($MgSO_4$) and concentrated. Heptane was added to the residue and the resulting solid was collected by filtration to give Compound 1c. MS m/z (MH+) 276.7; $^1$H NMR ($CDCl_3$) δ 7.43 (t, 1H), 7.52 (m, 2H), 7.76 (m, 2H), 8.23 (d, 1H), 8.35 (dd, 1H).

1-[3-(3-Bromo-xanthen-9-ylidene)-8-aza-bicyclo[3.2.1]oct-8-yl]-2,2,2-trifluoro-ethanone (5d). Using the method described in Procedure D, substituting Compound 1c for N-[2-(9-Oxo-9H-xanthen-3-yl)-phenyl]-acetamide and substituting Compound 5b for 3-oxo-8-aza-bicyclo[3.2.1]octane-8-carboxylic acid tert-butyl ester, the title compound 5d was prepared. MS m/z (MH+) 463.6, 465.8; $^1$H NMR ($CDCl_3$) δ 1.43 (m, 2H), 1.82 (m, 2H), 2.94 (m, 4H), 4.42 (m, 1H), 4.72 (m, 1H), 7.20 (m, 6H), 7.4 (m, 1H).

Procedure L

9-[8-(2,2,2-Trifluoro-acetyl)-8-aza-bicyclo[3.2.1]oct-3-ylidene]-9H-xanthene-3-carbonitrile (5e). To a solution of Compound 5d (3 g, 6.46 mmol) in DMF (100 mL) was added CuCN (0.69 g, 7.70 mmol). The reaction mixture was refluxed for 2 d and then cooled to room temperature. The mixture was poured into water (100 mL), and extracted with EtOAc (3×100 mL). The combined organic layers were washed sequentially with $H_2O$ (100 mL), brine (100 mL), then dried ($MgSO_4$) and concentrated. The crude product was purified by normal phase chromatography, using a gradient of ethyl acetate (0% to 10%) in heptane to give compound 5e. MS m/z (M+H+) 410.9; $^1$H NMR ($CDCl_3$) δ 1.41 (m, 2H), 1.85 (m, 2H), 2.96 (m, 4H), 4.44 (m, 1H), 4.73 (m, 1H), 7.23 (m, 3H), 7.33 (m, 2H), 7.43 (dt, 1H), 7.51 (m, 1H).

Procedure M 2,2,2-Trifluoro-1-{3-[3-(1H-tetrazol-5-yl)-xanthen-9-ylidene]-8-aza-bicyclo[3.2.1]oct-8-yl}-ethanone (5f). To a solution of Compound 5e (0.232 g, 0.56 mmol) in DMF (5 mL) were added $NaN_3$ (0.11 g, 1.69 mmol) and $NH_4Cl$ (0.09 g, 1.68 mmol). The reaction mixture was heated at 120° C. for 14 h, and then cooled to room temperature. An insoluble material was collected by filtration and washed with DMF (5 mL). The filtrate was acidified with 2N HCl (10 mL) and extracted with EtOAc (3×10 mL). The combined organic layers were washed with $H_2O$ (10 mL), dried ($MgSO_4$), and concentrated to give the title compound 5f which was used for subsequent reactions without further purification. MS m/z (MH+) 453.9.

Procedure N

3-[3-(1H-Tetrazol-5-ly)-xanthen-9-ylidene]-8-aza-bicyclo[3.2.1]octane (Cpd 1). To a solution of Compound 5f (0.2 g, 0.44 mmol) in $CH_3OH$ (4 mL) and $H_2O$ (1 mL) was added $K_2CO_3$ (0.152 g, 1.1 mmol). The mixture was stirred at room temperature for 14 h, and was purified by reverse phase HPLC to give the title Compound 1 as a TFA salt. MS m/z (MH+) 357.9; $^1$H NMR (DMSO-$d_6$) δ 1.27 (m, 2H), 1.77 (m, 2H), 2.97 (m, 4H), 4.00 (m, 2H), 7.36 (m, 4H), 7.63 (d, 1H), 7.91 (m, 3H), 8.82 (m, 1H), 9.17 (m, 1H).

Example 6

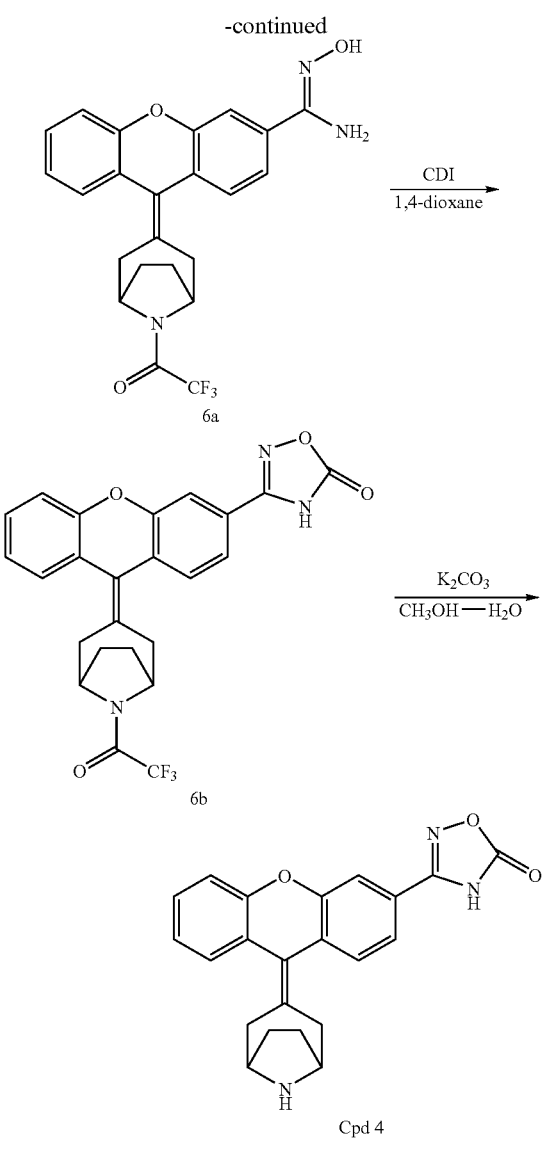

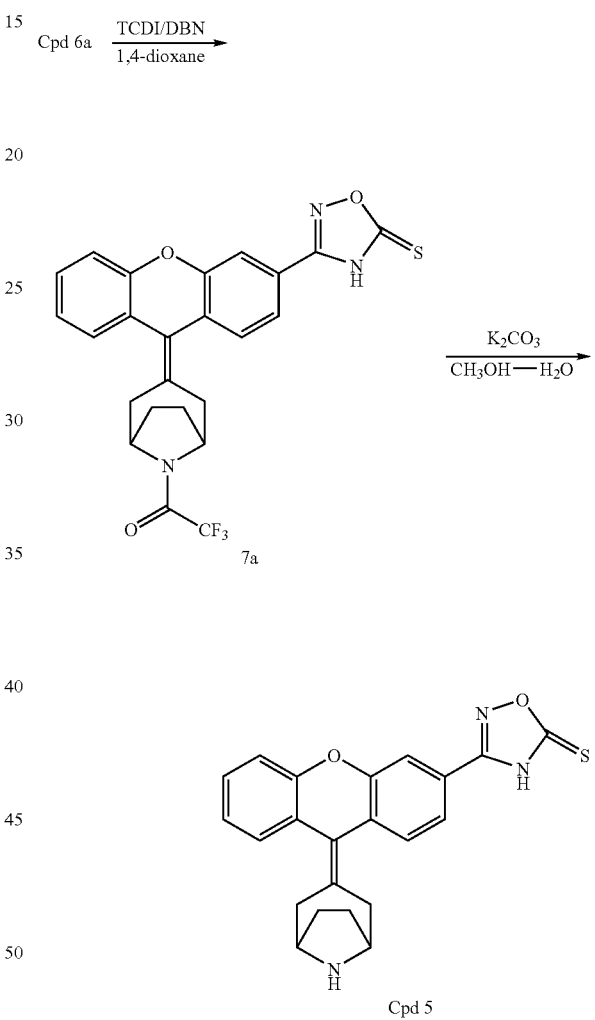

Procedure Q

3-[9-(8-Aza-bicyclo[3.2.1]oct-3-ylidene)-9H-xanthen-3-yl]-4H-[1,2,4]oxadiazol-5-one (Cpd 4). Using an adaptation of the method described in Procedure N and substituting compound 6b for compound 5f, the title compound 4 was prepared as a TFA salt. MS m/z (MH$^+$) 374.0; $^1$H NMR (CH$_3$OH-d$_4$) δ 1.48 (m, 2H), 1.94 (m, 2H), 3.11 (m, 4H), 4.06 (m, 2H), 7.26 (m, 2H), 7.38 (m, 2H), 7.51 (d, 1H), 7.62 (m, 3H).

Example 7

Procedure O

N-Hydroxy-9-[8-(2,2,2-trifluoro-acetyl)-8-aza-bicyclo[3.2.1]oct-3-ylidene]-9H-xanthene-3-carboxamidine (6a). To a suspension of compound 5e (0.44 g, 1.07 mmol) in EtOH (5 mL) were added NH$_2$OH.HCl (0.223 g, 3.19 mmol) and K$_2$CO$_3$ (0.3 g, 2.17 mmol). The reaction mixture was refluxed for 4 h. Upon cooling to room temperature, H$_2$O (1 mL) was added to the mixture. The mixture was extracted with CH$_2$Cl$_2$ (2×5mL), dried (MgSO$_4$), and concentrated to yield compound 6a. The product 6a was used in the next reaction without further purification. MS m/z (MH$^+$) 443.9.

Procedure P

3-{9-[8-(2,2,2-Trifluoro-acetyl)-8-aza-bicyclo[3.2.1]oct-3-ylidene]-9H-xanthen-3-yl}-4H-[1,2,4]oxadiazol-5-one (6b). To a solution of compound 6a (0.1 g, 0.23 mmol) in 1,4-dioxane (4 mL) was added 1,1'-carbonyldiimidazole (CDI, 0.055 g, 0.34 mmol). The mixture was stirred at 110° C. for 40 min under a nitrogen atmosphere. After being cooled, the reaction was concentrated. The crude compound 6b was used in the next reaction without further purification. MS m/z (MH$^+$) 469.8.

2,2,2-Trifluoro-1-{3-[3-(5-thioxo-4,5-dihydro-[1,2,4]oxadiazol-3-yl)-xanthen-9-ylidene]-8-aza-bicyclo[3.2.1]oct-8-yl}-ethanone (7a). Using an adaptation of Procedure P, substituting 1,1'-thiocarbonyidiimidazole (TCDI) for CDI and adding 1,8-diazabicyclo[5.4.0]undec-7-ene (DBN, 1 equivalent), the title compound 7a was prepared. The crude compound 7a was used in the next reaction without further purification. MS m/z (MH$^+$) 485.8.

3-[9-(8-Aza-bicyclo[3.2.1]oct-3-ylidene)-9H-xanthen-3-yl]-4H-[1,2,4]oxadiazole-5-thione (Cpd 5). Using an adaptation of the method described in Procedure N and substituting compound 7a for compound 5f, the title compound 5was prepared as a TFA salt. MS m/z (MH$^+$) 389.9; $^1$H NMR (CH₃OH-d₄) δ 1.47 (m, 2H), 1.93 (m, 2H), 3.10 (m, 4H), 4.06 (m, 2H), 7.27 (m, 2H), 7.37 (m, 2H), 7.53 (d, 1H), 7.67 (m, 3H).

Example 8

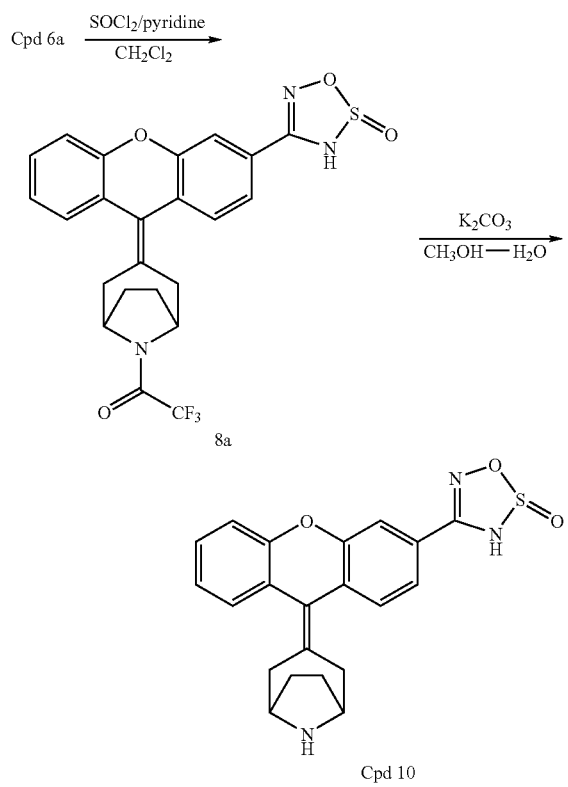

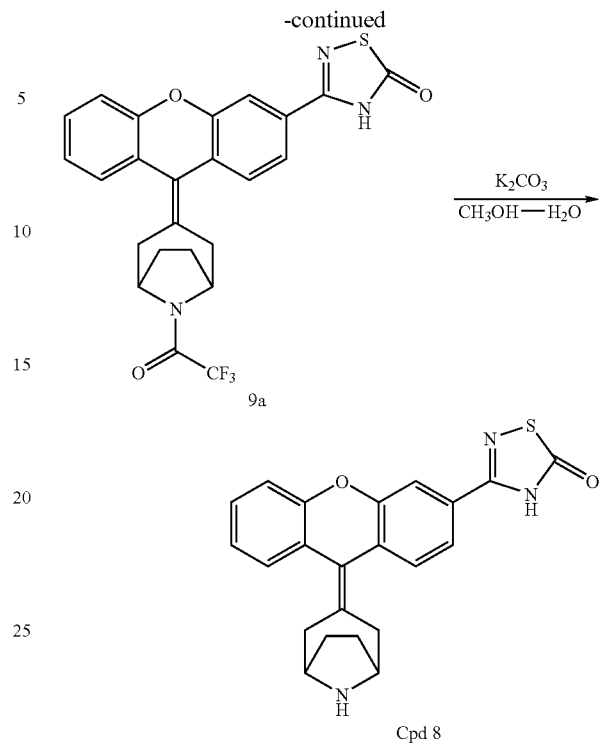

Procedure R 2,2,2-Trifluoro-1-{3-[3-(2-oxo-2,3-dihydro-2l4-[1,2,3,5]oxathiadiazol-4-yl)-xanthen-9-ylidene]-8-aza-bicyclo[3.2.1]oct-8-yl}-ethanone (8a). To a solution of compound 6a (0.071 g, 0.16 mmol) and pyridine (0.026 mL, 0.32 mmol) in CH₂Cl₂ (1 mL) was added dropwise a solution of thionyl chloride (0.013 mL, 0.18 mmol) in CH₂Cl₂ (1 mL) at −70° C. After being stirred for 1 h at −70° C., the mixture was allowed to warm to room temperature, and then washed sequentially with water and brine, dried (MgSO₄), and concentrated. The resulting compound 8a was used in the next reaction without further purification. MS m/z (MH⁺) 489.7.

3-[3-(2-Oxo-2,3-dihydro-2l4-[1,2,3,5]oxathiadiazol-4-yl)-xanthen-9-ylidene]-8-aza-bicyclo[3.2.1]octane (Cpd 10). Using an adaptation of the method described in Procedure N and substituting compound 8a for compound 5f, the title compound 10 was prepared as a TFA salt. MS m/z (MH⁺) 393.9; ¹H NMR (CH₃OH-d₄ δ 1.49 (m, 2H), 1.94 (m, 2H), 3.11 (m, 4H), 4.06 (m, 2H), 7.28 (m, 2H), 7.39 (m, 2H), 7.54 (d, 1H), 7.70 (m, 3H).

Example 9

Procedure S

3-{9-[8-(2,2,2-Trifluoro-acetyl)-8-aza-bicyclo[3.2.1]oct-3-ylidene]-9H-xanthen-3-yl}-4H-[1,2,4]thiadiazol-5-one (9a). A mixture of compound 6a (0.0417 g, 0.094 mmol) and TCDI (0.025 g, 0.14 mmol) in THF (2 mL) was stirred at room temperature for 45 min. The mixture was diluted with H₂O (2 mL) and extracted with EtOAc (3×5 mL). The combined organic extracts were washed with H₂O (15 mL), dried (MgSO₄), and concentrated. The residue was dissolved in THF (2 mL). Boron trifluoride diethyl etherate was added to the solution, and the resulting mixture was stirred at room temperature for 1 h. The mixture was diluted with H₂O (2 mL) and extracted with EtOAc (3×5mL). The organic layers were dried (MgSO₄), and concentrated. The resultant compound 9a was used in the next reaction without further purification. MS m/z (MH⁺) 485.8.

3-[9-(8-Aza-bicyclo[3.2.1]oct-3-ylidene)-9H-xanthen-3-yl]-4H-[1,2,4]thiadiazol-5-one (Cpd 8). Using an adaptation of the method described in Procedure N and substituting compound 9a for compound 5f, the title compound 8 was prepared as a TFA salt. MS m/z (MH⁺) 389.9; ¹H NMR (CH₃OH-d₄) δ 1.48 (m, 2H), 1.93 (m, 2H), 3.11 (m, 4H), 4.05 (m, 2H), 7.27 (m, 2H), 7.38 (m, 2H), 7.50 (d, 1H), 7.76 (m, 3H).

Example 10

-continued

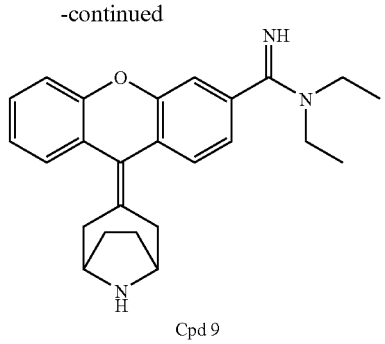
Cpd 9

9-(8-Aza-bicyclo[3.2.1]oct-3-ylidene)-N,N-diethyl-9H-xanthene-3-carboxamidine (Cpd 9). A mixture of compound 5e (0.06 g, 0.146 mmol), diethylamine (0.766 mL, 7.31 mmol) and Cu(I)Cl (0.0724 g, 0.731 mmol) in MeOH (1 mL) were exposed to microwave irradition (300 W) at 140° C. for 20 min. A portion of $K_2CO_3$ (0.2 g, 1.45 mmol) was added to the reaction mixture and stirred at room temperature for 3 h. The solid was collected by vacuum filtration, and the crude product was purified by reverse phase HPLC to give compound 9 as a TFA salt. MS m/z (MH$^+$)387.9; $^1$H NMR (CH$_3$OH-d$_4$) δ 1.22 (t, 3H), 1.39 (t, 3H), 1.48 (d, 2H), 1.96 (m, 2H), 3.12 (m, 4H), 3.42 (q, 2H), 3.7 (q, 2H), 4.07 (m, 2H), 7.28 (m, 2H), 7.40 (m, 3H), 7.53 (d, 1H), 7.61 (d, 1H).

Example 11

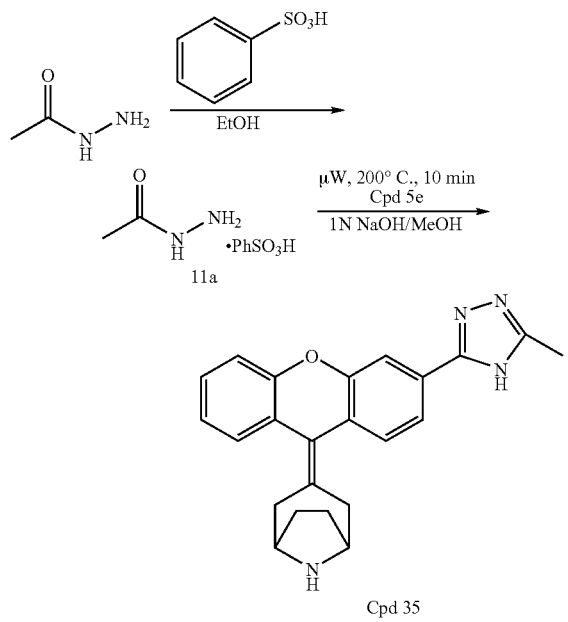
Cpd 35

Procedure T

Acetic hydrazide benzenesulfonic acid (11a). To a solution of acetic hydrazide (2g, 27.0 mmol) in EtOH (5 mL) was added benzenesulfonic acid (4.7g, 29.7 mmol) in small portions. A white solid formed. A volume of Et$_2$O (5 mL) was added to the mixture. The resulting solid was collected by filtration, washed with Et$_2$O, and dried to give compound 11a. $^1$H NMR (D$_2$O) δ 1.95 (s, 3H), 7.45 (m, 3H), 7.75 (d, 2H).

Procedure U

3-[3-(5-Methyl-4H-[1,2,4]triazol-3-yl)-xanthen-9-ylidene]-8-aza-bicyclo[3.2.1]octane (35). A mixture of compounds 11a (0.029 g, 0.125 mmol) and 5e (0.051g, 0.124 mmol) was exposed to microwave irradition (300 W) at 200° C. for 10 min. After cooling, MeOH (1 mL) and 1N NaOH (1 mL) were added to the reaction mixture and the mixture was stirred at rt for 30 min. The crude product was purified by reverse phase HPLC to yield compound 35 as a TFA salt. MS m/z (MH$^+$) 371.0; $^1$H NMR (CH$_3$OH-d$_4$) δ 1.40 (d, 2H), 1.85 (m, 2H), 1.41 (s, 3H), 3.02 (m, 4H), 3.91 (m, 2H), 7.19 (m, 4H), 7.33 (d, 2H), 7.84 (d, 1H), 7.85 (s, 1H).

Example 12

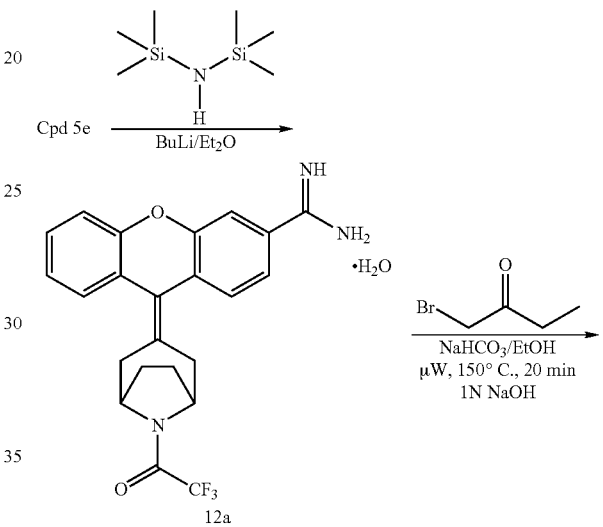
12a

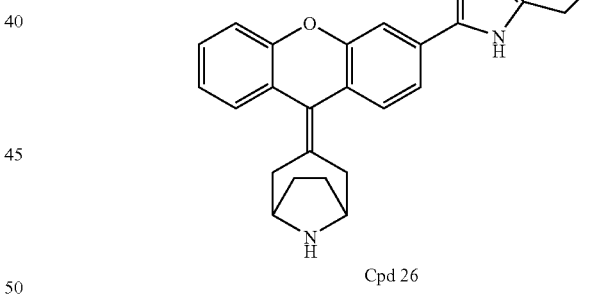
Cpd 26

Procedure V

9-[8-(2,2,2-Trifluoro-acetyl)-8-aza-bicyclo[3.2.1]oct-3-ylidene]-9H-xanthene-3-carboxamidine (12a). To a solution of n-BuLi (2.5M in hexanes, 0.487 mL, 1.22 mmol) in Et$_2$O (1 mL) was added dropwise a solution of 1,1,1,3,3,3-hexamethyldisilazane (0.257 mL, 1.22 mmol) in Et$_2$O (1 mL) at 0° C. The mixture was stirred at 0° C. for 30 min. Compound 5e (0.2g, 0.49 mmol) was added to the mixture and the mixture was stirred at rt for 2 h. The mixture was poured into ice-cold 2N HCl (2 mL) and extracted with Et$_2$O (2×3 mL). The aqueous phase was adjusted to pH ~8 with 1 N NaOH and extracted with CH$_2$Cl$_2$ (2×3 mL). The organic layers were combined, dried over MgSO$_4$, filtered, and concentrated. The resultant compound 12a was used in the next reaction without further purification. MS m/z (MH$^+$) 427.8.

Procedure W

3-[3-(5-Ethyl-1 H-imidazol-2-yl)-xanthen-9-ylidene]-8-aza-bicyclo[3.2.1]-octane (Cpd 26). A mixture of compound 12a (0.050 g, 0.112 mmol), 1-bromo-2-butanone (0.012 g, 0.118 mmol) and NaHCO$_3$ (0.02 g, 0.238 mmol) in EtOH (1 mL) were exposed to microwave irradition (300 W) at 150° C. for 20 min. After cooling, 1N NaOH (0.5 mL) was added to the reaction mixture and the mixture stirred at rt for 30 min. The crude product was purified by reverse phase HPLC to yield compound 26 as a TFA salt. MS m/z (MH$^+$) 384.0; $^1$H NMR (CH$_3$OH-d$_4$) δ 1.39 (m, 3H), 1.52 (m, 2H), 1.96 (m, 2H), 2.83 (q, 2H), 3.15 (m, 4H), 4.09 (m, 2H), 7.30 (m, 2H), 7.43 (m, 3H), 7.63 (m, 1H), 7.72 (m, 1H), 7.85 (m, 1H).

Example 13

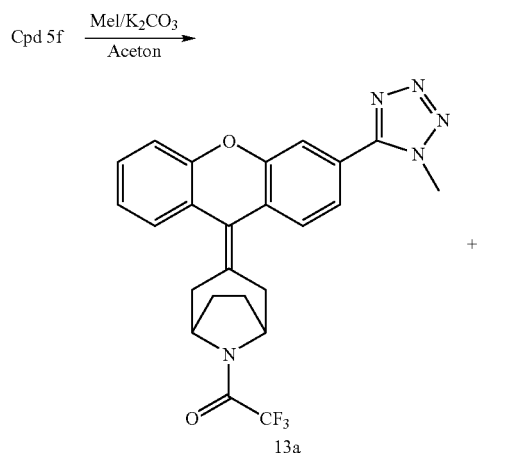

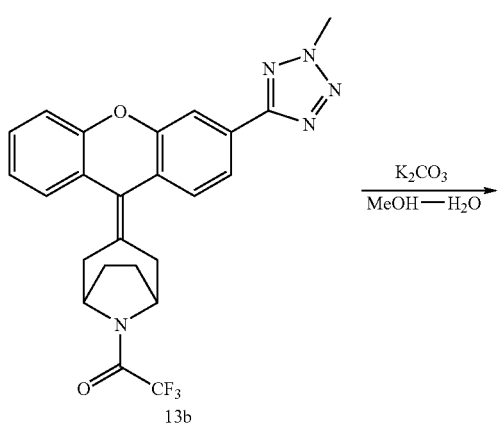

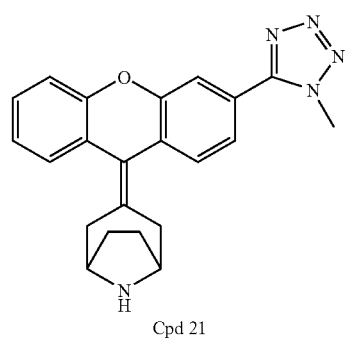

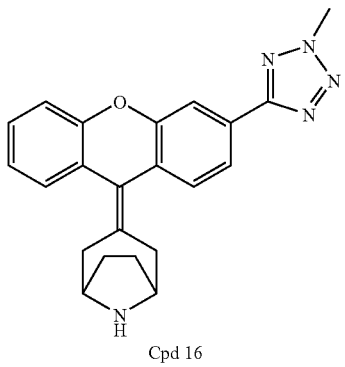

Cpd 16

Procedure X 2,2,2-Trifluoro-1-{3-[3-(1-methyl-1H-tetrazol-5-yl)-xanthen-9-ylidene]-8-aza-bicyclo[3.2.1]oct-8-yl}-ethanone (13a) and 2,2,2-Trifluoro-1-{3-[3-(2-methyl-2H-tetrazol-5-yl)-xanthen-9-ylidene]-8-aza-bicyclo[3.2.1]oct-8-yl}-ethanone (13b). A mixture of compound 5f (0.16 g, 0.35 mmol), methyl iodide (0.044 mL, 0.71 mmol) and potassium carbonate (0.24 g, 1.74 mmol) in acetone (8 mL) was heated to reflux (oil bath, 60° C.) for 2 h. The mixture was allowed to cool to rt, and the solid was removed via filtration. The solvent was removed in vacuo. The mixture of crude products 13a and 13b was used in the next reaction without further purification. MS m/z (MH$^+$) 467.9.

3-[3-(1-Methyl-1 H-tetrazol-5-yl)-xanthen-9-ylidene]-8-aza-bicyclo[3.2.1]octane (Cpd 21) and 3-[3-(2-Methyl-2H-tetrazol-5-yl)-xanthen-9-ylidene]-8-aza-bicyclo[3.2.1]octane (Cpd 16). Using an adaptation of the method described in Procedure N and substituting the mixture of compounds 13a and 13b for compound 5f, a mixture of the title compounds 21 and 16 were prepared. Compounds 21 and 16 were separated and purified via reverse phase HPLC as their TFA salts. Cpd 21: MS m/z (MH$^+$) 371.9; $^1$H NMR (CH$_3$OH-d$_4$,) δ 1.52 (d, 2H), 1.97 (m, 2H), 3.15 (m, 4H), 4.08 (m, 2H), 4.27 (s, 3H), 7.29 (m, 2H), 7.41 (m, 2H), 7.67 (m, 2H), 7.76 (d, 1H). Cpd 16: MS m/z (MH$^+$) 371.9; $^1$H NMR (CH$_3$OH-d$_4$,) δ 1.52 (d, 2H), 1.95 (m, 2H), 3.12 (m, 4H), 4.06 (m, 2H), 4.45 (s, 3H), 7.24 (m, 2H), 7.37 (m, 2H), 7.53 (d, 1H), 7.96 (m, 2H).

Example 14

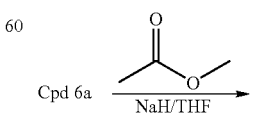

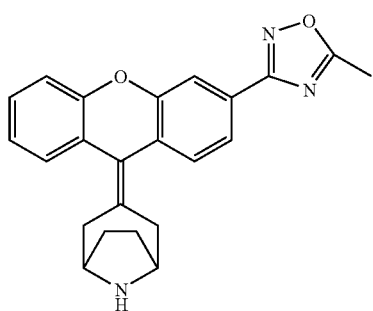

Cpd 36

Procedure Y

3-[3-(5-Methyl-[1,2,4]oxadiazol-3-yl)-xanthen-9-ylidene]-8-aza-bicyclo[3.2.1]octane (Cpd 36). A mixture of Compound 6a (0.046 g, 0.104 mmol) and NaH (60% in oil, 0.0042 mg, 0.105 mmol) in THF (4 mL) was refluxed for 1 h. After cooling, acetic acid methyl ester (0.0082 mL, 0.103 mmol) was added to the mixture. The mixture was stirred at reflux temperature overnight. The mixture was poured into ice-cold water and extracted with $CH_2Cl_2$ (2×5 mL). The organic phase was washed with $H_2O$, dried over $MgSO_4$, and concentrated. The crude product was purified by reverse phase HPLC to give Compound 36 as a TFA salt. MS m/z ($MH^+$) 371.9; $^1H$ NMR ($CH_3OH$-$d_4$) δ 1.52 (d, 2H), 1.95 (m, 2H), 2.66 (s, 3H), 3.12 (m, 4H), 4.05 (m, 2H), 7.23 (m, 1H), 7.31 (m, 1H), 7.39 (m, 2H), 7.52 (d, 1H), 7.83 (d, 1H), 7.84 (s, 1H).

Example 15

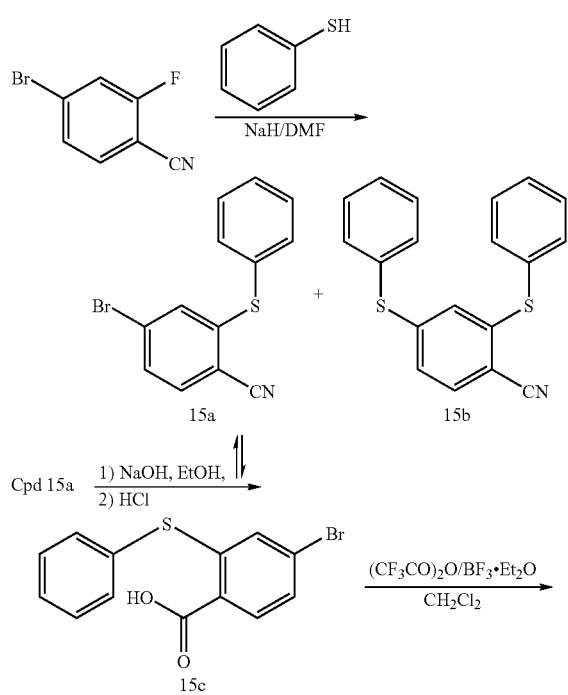

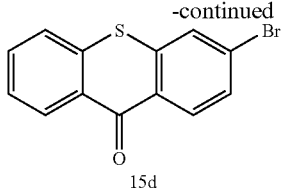

15d

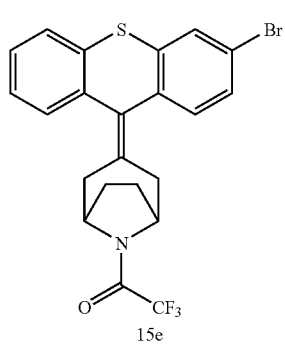

15e

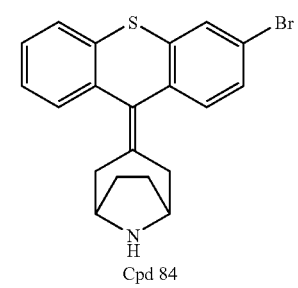

Cpd 84

4-Bromo-2-phenylsulfanyl-benzonitrile (15a) and 2,4-Bis-phenylsulfanyl-benzonitrile (15b). Using the method described in Procedure I, substituting benzenethiol for phenol, a mixture of the title compounds 15a and 15b were prepared. The mixture was separated via normal phase chromatography (eluent gradient: 0 to 20% EtOAc in heptane) to yield Compounds 15a and 15b. Compound 15a: MS m/z ($MH^+$) 291.8; Compound 15b: MS m/z ($MH^+$) 319.8.

4-Bromo-2-phenylsulfanyl-benzoic acid (15c). Using the method described in Procedure J, substituting Compound 15a for Compound 5c, Compound 15c was prepared. MS m/z ($MH^+$) 308.7.

3-Bromo-thioxanthen-9-one (15d). Using the method described in Procedure K, substituting Compound 15c for Compound 1b, Compound 15d was prepared. MS m/z ($MH^+$) 290.7.

1-[3-(3-Bromo-thioxanthen-9-ylidene)-8-aza-bicyclo [3.2.1]oct-8-yl]-2,2,2-trifluoro-ethanone (15e). Using the method described in Procedure D, substituting Compound 15d for N-[2-(9-oxo-9H-xanthen-3-yl)-phenyl]-acetamide and substituting Compound 5b for 3-oxo-8-aza-bicyclo-[3.2.1]carboxylic acid tert-butyl ester, Compound 15e was prepared. MS m/z ($MH^+$) 481.6.

3-(3-Bromo-thioxanthen-9-ylidene)-8-aza-bicyclo[3.2.1] octane (84). Using the method described in Procedure N, substituting Compound 15e for Compound 5f, the title compound 84 was prepared as a TFA salt. MS m/z ($MH^+$) 385.6;

$^1$H NMR (DMSO-d$_6$) δ 1.27 (m, 2H), 1.77 (m, 2H), 2.97 (m, 4H), 4.00 (m, 2H), 7.36 (m, 4H), 7.63 (d, 1H), 7.91 (m, 3H), 8.82 (m, 1H), 9.17 (m, 1H).

Example 16

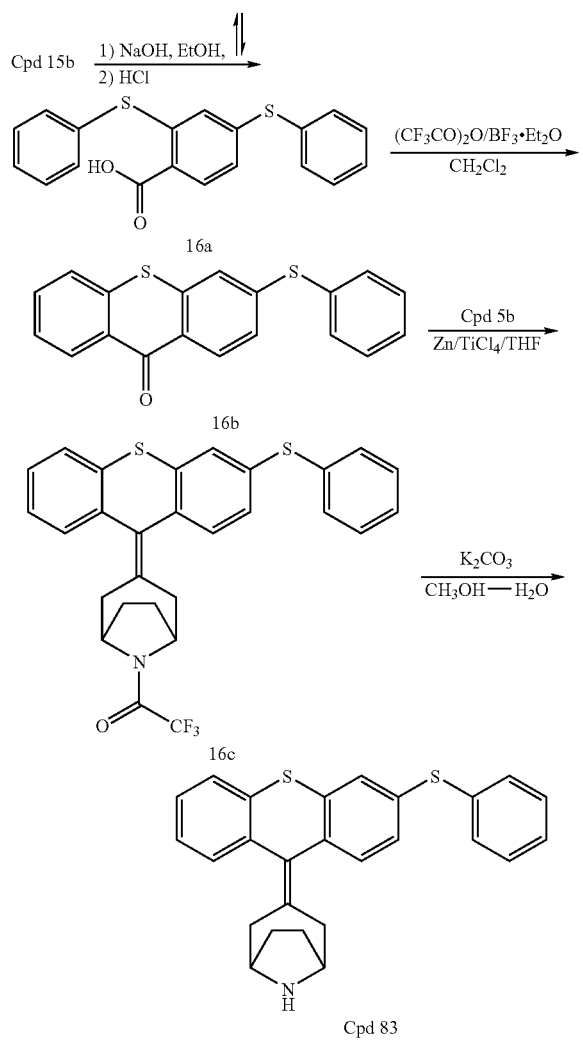

3-(3-Phenylsulfanyl-thioxanthen-9-ylidene)-8-aza-bicyclo[3.2.1]octane (16a). Using the method described in Procedure J, substituting Compound 15b for Compound 5c, the title compound 16a was prepared. MS m/z (MH$^+$) 338.7.

3-Phenylsulfanyl-thioxanthen-9-one (16b). Using the method described in Procedure K, substituting Compound 16a for Compound 1b, Compound 16b was prepared. MS m/z (MH$^+$) 320.9.

2,2,2-Trifluoro-1-[3-(3-phenylsulfanyl-thioxanthen-9-ylidene)-8-aza-bicyclo[3.2.1]oct-8-yl]-ethanone (16c). Using the method described in Procedure D, substituting Compound 16b for N-[2-(9-oxo-9H-xanthen-3-yl)-phenyl]-acetamide and substituting Compound 5b for 3-oxo-8-aza-bicyclo-[3.2.1] carboxylic acid tert-butyl ester, Compound 16c was prepared. MS m/z (MH$^+$) 509.7.

3-(3-Phenylsulfanyl-thioxanthen-9-ylidene)-8-aza-bicyclo[3.2.1]octane (83). Using the method described in Procedure N, substituting Compound 16c for Compound 5f, the title compound 83 was prepared as a TFA salt. MS m/z (MH$^+$) 413.7; $^1$H NMR (CH$_3$OH-d$_4$) δ 1.32 (m, 2H), 1.76 (m, 2H), 2.74 (m, 4H), 3.84 (m, 2H), 7.25 (m, 11 H), 7.41 (d, 1 H).

Example 17

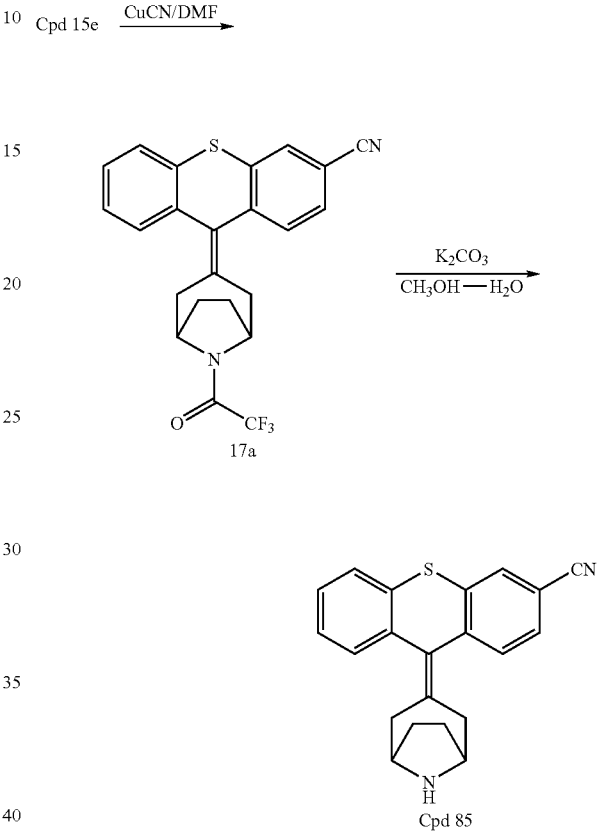

9-[8-(2,2,2-Trifluoro-acetyl)-8-aza-bicyclo[3.2.1]oct-3-ylidene]-9H-thioxanthene-3-carbonitrile (17a). Using the method described in Procedure L, substituting Compound 15e for Compound 5d, the title compound 17a was prepared. MS m/z (MH$^+$) 426.7; $^1$H NMR (CDCl$_3$) δ 1.41 (m, 2H), 1.83 (m, 2H), 2.76 (m, 4H), 4.40 (m, 1H), 4.70 (m, 1H), 7.33 (m, 4H), 7.56 (m, 2H), 7.51 (s, 1H).

9-(8-Aza-bicyclo[3.2.1]oct-3-ylidene)-9H-thioxanthene-3-carbonitrile (85). Using the method described in Procedure N, substituting Compound 17a for Compound 5f, the title compound 85 was prepared. MS m/z (MH$^+$) 330.9; $^1$H NMR (CH$_3$OH-d$_4$) δ 1.33 (m, 2H), 1.81 (m, 2H), 2.78 (m, 4H), 3.91 (m, 2H), 7.21 (m, 3H), 7.38 (d, 1H), 7.49 (d, 1H), 7.57 (dd, 1H), 7.85 (d, 1H).

Example 18

Cpd 17a $\xrightarrow[\text{Chiralpack AD}]{\text{Chiral separation}}$

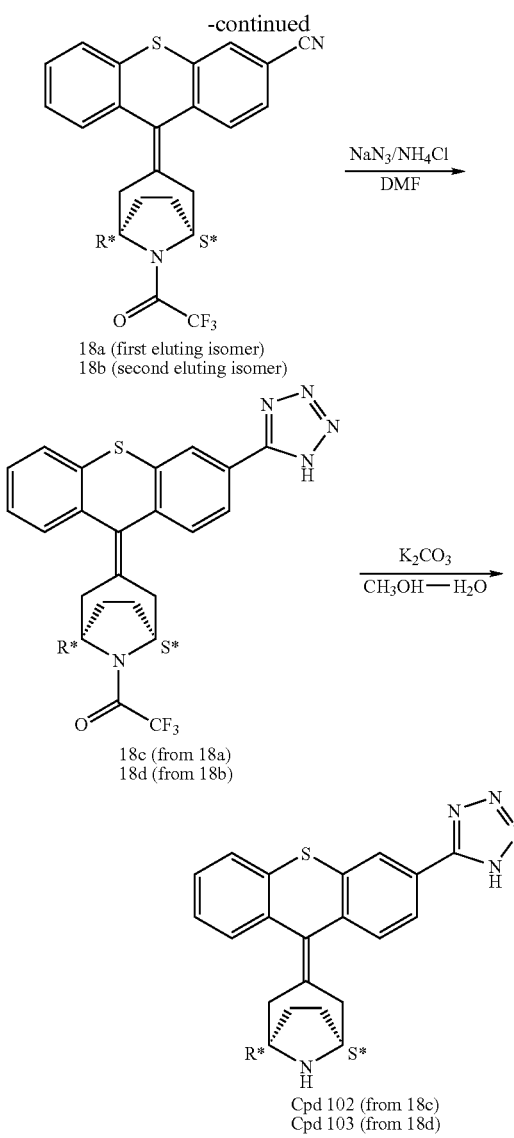

18a (first eluting isomer)
18b (second eluting isomer)

18c (from 18a)
18d (from 18b)

Cpd 102 (from 18c)
Cpd 103 (from 18d)

9-[(1RS,5SR)-8-(2,2,2-Trifluoro-acetyl)-8-aza-bicyclo[3.2.1]oct-3-ylidene]-9H-thioxanthene-3-carbonitrile (18a) and 9-[(1SR,5RS)-8-(2,2,2-trifluoro-acetyl)-8-aza-bicyclo[3.2.1]oct-3-ylidene]-9H-thioxanthene-3-carbonitrile (18b). Racemic Compound 17a was separated via chiral chromatography into its enantiomers using a Chiralpack AD column (500 g) and a 1:1 heptane:ethanol eluent mixture (UV monitoring at 220 nm and flow rate of 80 mL/min), yielding Compounds 18a (first eluting isomer) and 18b (second eluting isomer).

2,2,2-Trifluoro-1-{3-[3-(1tetrazol-5-yl)-thioxanthen-9-ylidene]-[(1RS,5SR)-8-aza-bicyclo[3.2.1]oct-8-yl}]-ethanone (18c) and 2,2,2-trifluoro-1-{3-[3-(1H-tetrazol-5-yl)-thioxanthen-9ylidene]-[(1SR,5RS)-8-aza-bicyclo[3.2.1]oct-8-yl}-ethanone (18d). Using the method described in Procedure M, substituting Compound 18a for Compound 5e, the title compound 18c was prepared. MS m/z (MH$^+$) 469.8. Similarly, using the method described in Procedure M, substituting Compound 18b for Compound 5e, the title compound 18d was prepared.

(1RS,5SR)-3-[3-(1H-Tetrazol-5-yl)-thioxanthen-9-ylidene]-8-aza-bicyclo[3.2.1]octane (Cpd 102) and (1SR,5RS)-3-[3-(1H-tetrazol-5-yl)-thioxanthen-9-ylidene]-8-aza-bicyclo[3.2.1]octane (Cpd 103).

Using the method described in Procedure N, substituting Compound 18c for Compound 5f, the title compound 102 was prepared as a TFA salt. MS m/z (MH$^+$) 373.8; $^1$H NMR (CH$_3$OH-d$_4$) δ 1.37 (m, 2H), 1.79 (m, 2H), 2.84 (m, 4H), 3.89 (m, 2H), 7.25 (m, 3H), 7.43 (d, 1H), 7.50 (d, 1H), 7.91 (dd, 1H), 8.13 (d, 1H). Similarly, using the method described in Procedure N, substituting Compound 18d for Compound 5f, the title compound 103 was prepared as a TFA salt.

Example 19

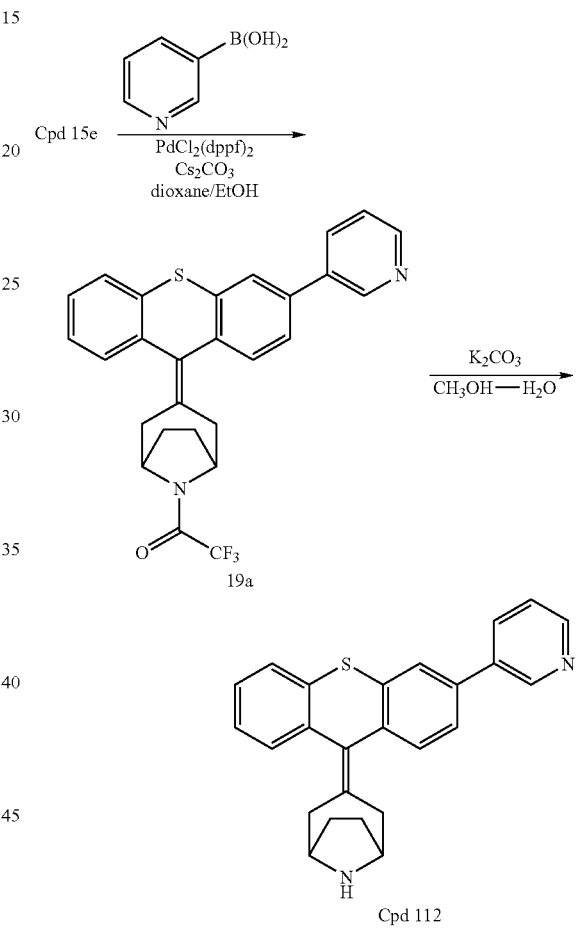

Cpd 112

Procedure Z 2,2,2-Trifluoro-1-[3-(3-pyridin-3-yl-thioxanthen-9-ylidene)-8-aza-bicyclo[3.2.1]oct-8-yl]-ethanone (19a) To a suspension of compound 15e (0.3 g, 0.625 mmol), cesium carbonate (0.51 g, 1.565 mmol) and 3-pyridineboronic acid (0.0844 g, 0.687 mmol) in dioxane (4 mL) and EtOH (1 mL) was added 1,1'-bis-(diphenylphosphino)-ferrocene-palladium (II) dichloride (46 mg, 0.063 mmol). The mixture was heated at 90° C. for 3 hrs, and cooled to room temperature. The solid was filtreted, and washed with CH$_3$OH (10 mL) and H$_2$O (10 mL). The filtrate was concentrated under reduce pressure to afford crude product. The crude product 19a was used in the next reaction without further purification. MS m/z (MH$^+$) 479.0.

3-(3-Pyridin-3-yl-thioxanthen-9-ylidene)-8-aza-bicyclo[3.2.1]octane (Cpd 112). Using the method described in Procedure N, substituting Compound 19a for Compound 5f, the title compound 112 was prepared as a TFA salt. MS m/z (MH+) 383.3; ¹H NMR (CDCl₃) δ 1.50 (m, 2H), 2.02 (m, 2H), 2.80 (t, 2H), 3.12 (m, 2H), 4.00 (m, 2H), 7.31 (m, 3H), 7.42 (d, 2H), 7.55 (dd, 1H), 7.78 (s, 1H), 7.92 (dd, 1H), 8.40 (d, 1H), 8.76 (d, 1H), 9.08 (s, 1H).

Example 20

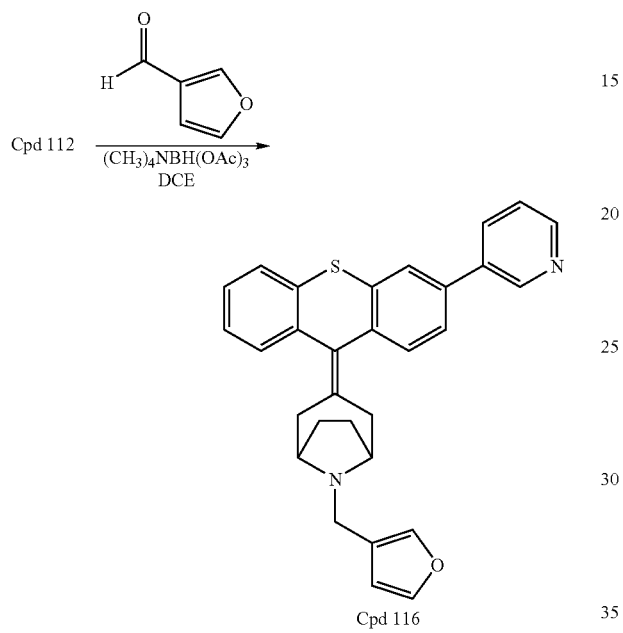

Procedure AA

8-Furan-3-ylmethyl-3-(3-pyridin-3-yl-thioxanthen-9-ylidene)-8-aza-bicyclo[3.2.1]octane (116) A mixture of compound 112 (20 mg, 0.04 mmol), 3-furaldehyde (13.5 mg, 0.156 mmol) and tetramethylammonium triacetoxyborohydride (16 mg, 0.061 mmol) in dichloroethane (2 mL) was stirred at 80° C. overnight in a sealed tube. The solvent was removed under reduced prossure. The crude product was purified by reverse phase HPLC to give compound 116 as a TFA salt. MS m/z (MH+) 463.2; ¹H NMR (CD₃CN) δ 1.45 (d, 2H), 2.06 (m, 2H), 2.90 (m, 2H), 3.80 (m, 2H), 3.98 (m, 2H), 6.69 (s, 1H), 7.35 (m, 3H), 7.48 (d, 1H), 7.61 (m, 4H), 7.78 (m, 1H), 7.96 (s, 1H), 8.41 (d, 1H), 8.75 (d, 1H), 9.01 (s, 1H).

Example 21

-continued

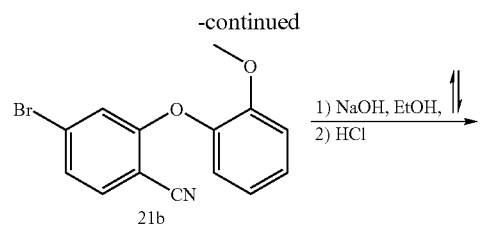

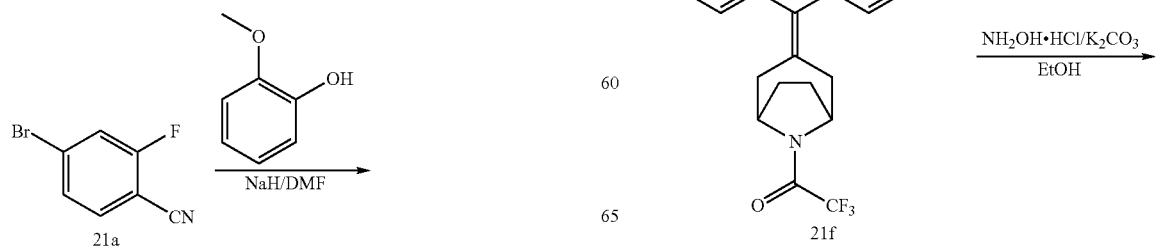

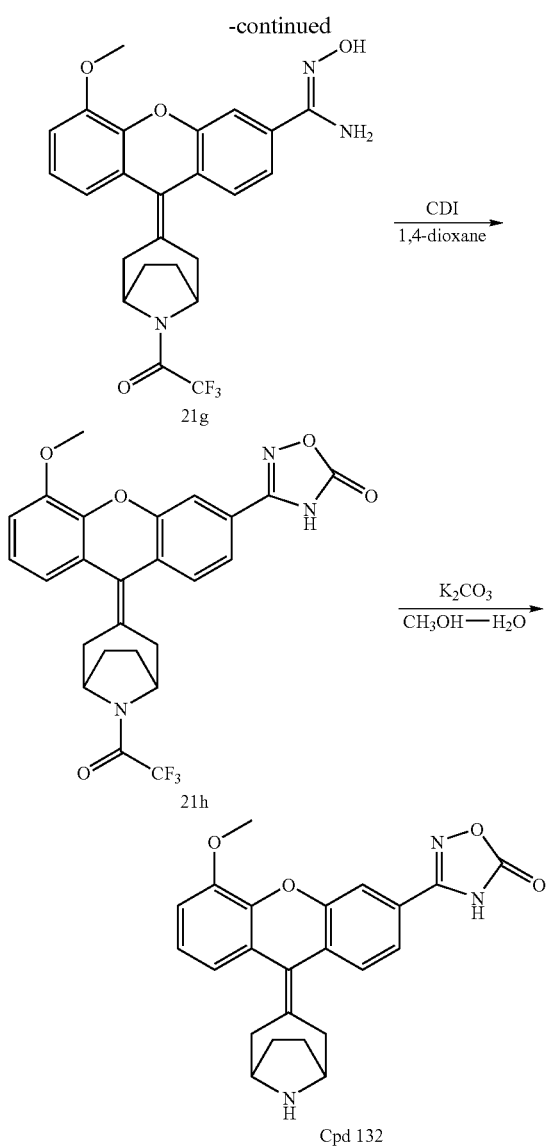

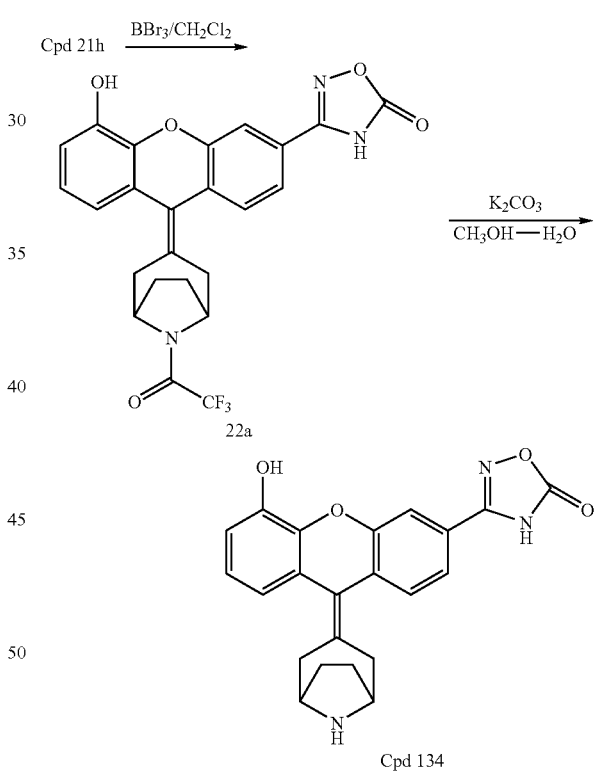

Using the method described in Procedure L, substituting Compound 21e for Compound 5d, the title compound 21e was prepared. MS m/z (M+23) 462.7.

3-[9-(8-Aza-bicyclo[3.2.1]oct-3-ylidene)-5-methoxy-9H-xanthen-3-yl]-4H-[1,2,4]oxadiazol-5-one (21g). Using the method described in Procedure O, substituting Compound 21f for Compound 5e, the title compound 21 g was prepared. MS m/z (MH+) 473.9.

3-{5-Methoxy-9-[8-(2,2,2-trifluoro-acetyl)-8-aza-bicyclo [3.2.1]oct-3-ylidene]-9H-xanthen-3-yl}-4H-[1,2,4]oxadiazol-5-one (21h). Using the method described in Procedure P, substituting Compound 21g for Compound 6a, the title compound 21h was prepared. MS m/z (MH+) 499.8.

3-[9-(8-Aza-bicyclo[3.2.1]oct-3-ylidene)-5-methoxy-9H-xanthen-3-yl]-4H-[1,2,4]oxadiazol-5-one (132). Using the method described in Procedure N, substituting Compound 21h for Compound 5f, the title compound 132 was prepared as a TFA salt. MS m/z (MH+) 403.9; $^1$H NMR (DMSO-$d_6$) δ 1.28 (m, 2H), 1.79 (m, 2H), 2.98 (m, 4H), 3.90 (s, 3H), 4.03 (m, 2H), 6.98 (d, 1H), 7.10 (d, 1H), 7.19 (t, 1H), 7.65 (m, 2H), 7.74 (s, 1H).

Example 22

4-Bromo-2-(2-methoxy-phenoxy)-benzonitrile (21b). Using the method described in Procedure I, substituting 2-methoxyphenol for phenol, the title compound 21b was prepared. MS m/z (MH+) 303.8, 305.8.

4-Bromo-2-(2-methoxy-phenoxy)-benzoic acid (21c). Using the method described in Procedure J, substituting Compound 21b for Compound 5c, the title compound 21c was prepared. MS m/z (MH+) 322.8, 324.7.

3-Bromo-5-methoxy-xanthen-9-one (21d).
Using the method described in Procedure K, substituting Compound 21c for Compound 1b, the title compound 21d was prepared. MS m/z(MH+) 304.8, 306.7.

1-[3-(3-Bromo-5-methoxy-xanthen-9-ylidene)-8-aza-bicyclo[3.2.1]oct-8-yl]-2,2,2-trifluoro-ethanone (21e). Using the method described in Procedure D, substituting Compound 21d for Compound 1c and substituting Compound 5b for 3-oxo-8-aza-bicyclo[3.2.1]-octane-8-carboxylic acid tert-butyl ester, the title compound 21e was prepared. MS m/z (MH+) 467.7, 469.7.

5-Methoxy-9-[8-(2,2,2-trifluoro-acetyl)-8-aza-bicyclo [3.2.1]oct-3-ylidene]-9H-xanthene-3-carbonitrile (21f).

Procedure BB

3-{5-Hydroxy-9-[8-(2,2,2-trifluoro-acetyl)-8-aza-bicyclo [3.2.1]oct-3-ylidene]-9H-xanthen-3-yl}-4H-[1,2,4]oxadiazol-5-one (22a). To a solution of Compound 21h (0.355 g, 1.19 mmol) in CH$_2$Cl$_2$ (30 mL) was added dropwise BBr$_3$ (1.0M in CH$_2$Cl$_2$, 5.97 mL, 5.97 mmol) at 0° C. The mixture was stirred at rt for 24 h, and quenched with a saturated NaHCO$_3$ solution (20 mL). The organic layer was dried over MgSO$_4$ and concentrated. The crude product was used in the next reaction without further purification. MS m/z (MH+) 485.8.

3-[9-(8-Aza-bicyclo[3.2.1]oct-3-ylidene)-5-hydroxy-9H-xanthen-3-yl]-4H-[1,2,4]oxadiazol-5-one (134). Using the method described in Procedure N, substituting Compound 22a for Compound 5f, the title compound 134 was prepared as a TFA salt. MS m/z (MH⁺) 389.9; ¹H NMR (CH₃OH-d₄) δ 1.43 (m, 2H), 1.82 (m, 2H), 2.95 (m, 2H), 3.22 (t, 2H), 3.94 (m, 2H), 6.75 (m, 2H), 7.00 (t, 1H), 7.42 (d, 1H), 7.51 (dd, 1H), 7.65 (s, 1H).

Example 23

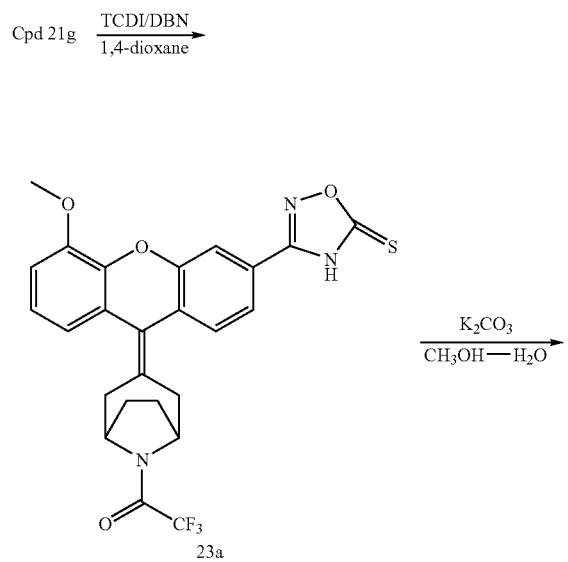

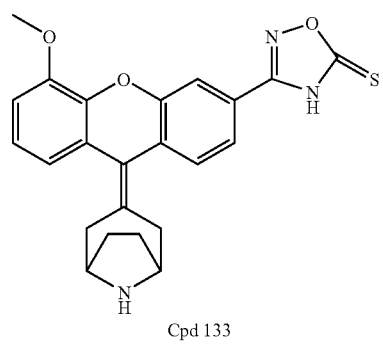

2,2,2-Trifluoro-1-{3-[5-methoxy-3-(5-thioxo-4,5-dihydro-[1,2,4]oxadiazol-3-yl)-xanthen-9-ylidene]-8-aza-bicyclo[3.2.1]oct-8-yl}-ethanone (23a)

Using the method described in Procedure P, substituting Compound 21g for Compound 6a, substituting 1,1'-thiocarbonyldiimidazole (TCDI) for CDI and adding 1,8-diazabicyclo[5.4.0]undec-7-ene (DBN, 1 equivalent), the title compound 23a was prepared. MS m/z (MH⁺) 515.8.

3-[9-(8-Aza-bicyclo[3.2.1]oct-3-ylidene)-5-methoxy-9H-xanthen-3-yl]-4H-[1,2,4]oxadiazole-5-thione (133). Using the method described in Procedure N, substituting Compound 23a for Compound 5f, the title compound 133 was prepared as a TFA salt. MS m/z (MH⁺) 419.9; ¹H NMR (DMSO-d₆) δ 1.26 (m, 2H), 1.78 (m, 2H), 2.93 (m, 2H), 3.32 (t, 2H), 3.90 (s, 3H), 4.00 (m, 2H), 6.98 (t, 1H), 7.10 (t, 1H), 7.28 (t, 1H), 7.58 (d, 1H), 7.81 (d, 1H), 7.90 (s, 1H).

Example 24

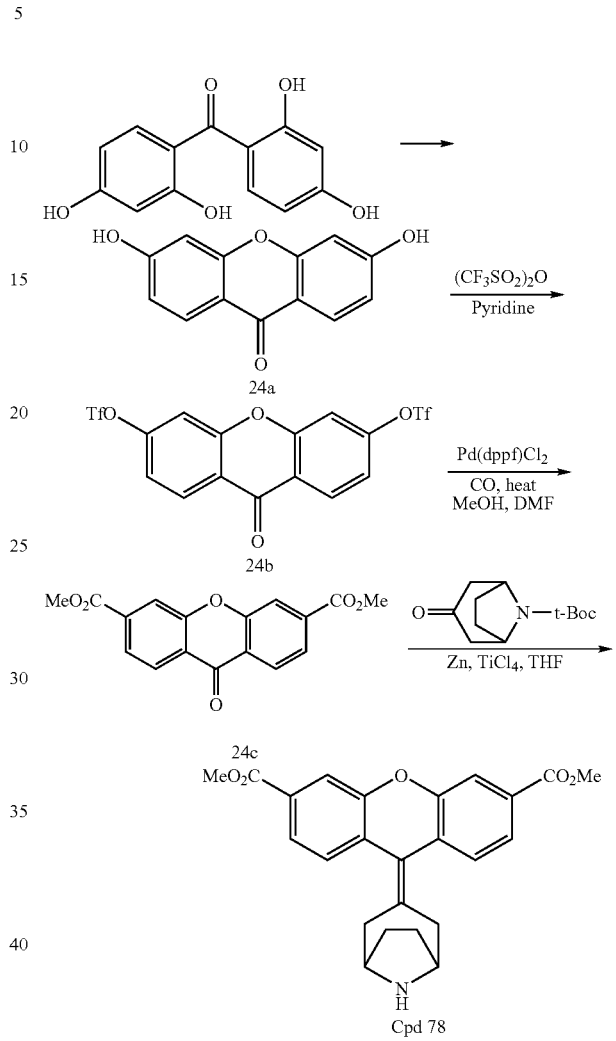

Procedure CC 3,6-Dihydroxy-xanthen-9-one (24a). Following a procedure disclosed in the literature, (Janjic, N. et al. *J. Am. Chem. Soc.* 1989, 111, 6374-6375) compound 24a was prepared. MS m/z (MH⁺) 228.9.

Procedure DD

Trifluoro-methanesulfonic acid 9-oxo-6-trifluoromethane-sulfonyloxy-9H-xanthen-3-yl ester (24b). Compound 24a (1.18 g, 5.18 mmol) was suspended in 30 mL of dichloromethane, treated with pyridine (836 mL), and stirred at rt for 10 min. Upon cooling to 0 C., triflic anhydride (1.73 mL, 10.3 mmol) was added dropwise. The mixture was stirred at 0 C. for 1 h and then allowed to warm to rt with additional stirring overnight. Upon completion of the reaction the mixture was concentrated under reduced pressure. The resultant residue was purified by normal phase chromatography using dichloromethane as eluant to give compound 24b. MS m/z (MH⁺) 492.6.

Procedure EE

9-Oxo-9H-xanthene-3,6-dicarboxylic acid dimethyl ester (24c). Compound 24b (0.52 g, 1.06 mmol) and DIEA (553

µL) were added to a mixture of DMF:MeOH (1:1, 20 mL total volume) and the flask was purged with Argon gas. The mixture was then treated with Pd(dppf)Cl$_2$ (43 mg, 0.053 mmol), purged, then charged with carbon monoxide and heated to 75 C. for 8 h. The mixture was cooled to rt and concentrated under reduced pressure at 50 C. The resultant residue was taken up in CH$_2$Cl$_2$, and washed sequentially with 1 N HCl, saturated aqueous NaHCO$_3$, and brine. The organic phase was partitioned, dried over magnesium sulfate, filtered, and the filtrate was concentrated to a residue. The residue was purified by normal phase chromatography using a gradient of 0.1 to 0.4% MeOH in dichloromethane as eluant to give compound 24c.

9-(8-Aza-bicyclo[3.2.1]oct-3-ylidene)-9H-xanthene-3,6-dicarboxylic acid dimethyl ester (78). The title compound was prepared according to Procedure D, substituting 9-oxo-9H-xanthene-3,6-dicarboxylic acid dimethyl ester for N-[2-(9-oxo-9H-xanthen-3-yl)-phenyl]-acetamide.

Compounds 1 through 134 of Formula (Ia) (wherein R$_5$ is H and A is CH$_2$CH$_2$), in the table below were synthesized using the procedures described above.

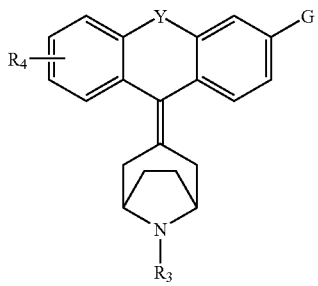

Formula (Ia)

| Cpd | G | R$_3$ | R$_4$ | Y |
|---|---|---|---|---|
| 1 | 1H-tetrazol-5-yl | H | H | O |
| 2 | 2-methylcarbonyl aminophenyl | H | H | O |
| 3 | N-(2-dimethylamino-eth-1-yl)-N-methyl-aminocarbonyl | ethoxy carbonyl | H | O |
| 4 | 4H-[1,2,4]-oxadiazol-5-oxo-3-yl | H | H | O |
| 5 | 4H-[1,2,4]-oxadiazol-5-thioxo-3-yl | H | H | O |
| 6 | pyrrolidin-1-ylcarbonyl | H | H | O |
| 7 | N-(2-methoxy-ethyl)-N-methyl-aminocarbonyl | H | H | O |
| 8 | 4H-[1,2,4]thiadiazol-5-oxo-3-yl | H | H | O |
| 9 | N,N-diethylamidino | H | H | O |
| 10 | [1,2,3,5]oxathiadiazol-2-oxo-4-yl | H | H | O |
| 11 | N-(3-fluorophenyl)-methyl-aminocarbonyl | H | H | O |
| 12 | pyridin-3-yl | H | H | O |
| 13 | N-[2-(2,6-dimethylphenoxy)-1-methyl-ethyl]aminocarbonyl | H | H | O |
| 14 | N-phenyl-N-methyl-aminocarbonyl | H | H | O |
| 15 | N-(1(S)-hydroxymethyl-2-phenyl-eth-1-yl)aminocarbonyl | H | H | O |
| 16 | 2-methyl-tetrazol-5-yl | H | H | O |
| 17 | N-(2-phenylethyl)-N-methyl-aminocarbonyl | H | H | O |
| 18 | 2-aminocarbonyl-phenyl | H | H | O |
| 19 | 2-phenylethyl-aminocarbonyl | H | H | O |
| 20 | 3-methylcarbonylamino-phenyl | H | H | O |
| 21 | 1-methyl-tetrazol-5-yl | H | H | O |
| 22 | N-cyclohexyl-N-methyl-aminocarbonyl | H | H | O |
| 23 | 3-hydroxymethyl-phenyl | H | H | O |
| 24 | N-hydroxyamidino | H | H | O |
| 25 | 2-aminophenyl | H | H | O |
| 26 | 5-ethyl-1H-imidazol-2-yl | H | H | O |
| 27 | N-(1(R)-hydroxymethyl-2-phenyl-eth-1-yl)-aminocarbonyl | H | H | O |
| 28 | N,N-diisobutylamidino | H | H | O |
| 29 | pyridin-4-yl | H | H | O |
| 30 | 4-methylcarbonylamino-phenyl | H | H | O |
| 31 | N-(1S-methoxymethyl-2-phenyl-eth-1-yl)aminocarbonyl | H | H | O |
| 32 | 2-methoxypyridin-5-yl | H | H | O |
| 33 | 4,5-dihydro-1H-imidazol-2-yl | H | H | O |
| 34 | N-(4-phenyl)-cyclohexyl-aminocarbonyl | H | H | O |
| 35 | 3-methyl-4H-[1,2,4]triazol-5-yl | H | H | O |
| 36 | 5-methyl-[1,2,4]oxadiazol-4-yl | H | H | O |
| 37 | N-(1(S)-hydroxymethyl-1-methoxycarbonyl)amino carbonyl | H | H | O |
| 38 | 3-hydroxy-phenyl | H | H | O |
| 39 | isopropylamidino | H | H | O |
| 40 | phenylmethylamino carbonyl | H | H | O |
| 41 | 1,4,5,6-tetrahydro pyrimidin-2-yl | H | H | O |
| 42 | 4-aminophenyl | H | H | O |
| 43 | C-piperidin-1-yl-methyleneamine | H | H | O |
| 44 | 2-methoxyphenyl | H | H | O |
| 45 | cyclopentylaminocarbonyl | H | H | O |
| 46 | 3-methylphenyl | H | H | O |
| 47 | phenylaminocarbonyl | H | H | O |
| 48 | N,N-bis(2,2,2-trifluoro-eth-1-yl)aminocarbonyl | H | H | O |
| 49 | isobutylamidino | H | H | O |
| 50 | C-morpholin-4-yl-methyleneamine | H | H | O |
| 51 | 3-fluorophenyl | H | H | O |
| 52 | N-benzyl-N-methyl-aminocarbonyl | H | H | O |
| 53 | 4-methanesulfonyl-phenyl | H | H | O |
| 54 | 4-fluorophenyl | H | H | O |
| 55 | thiophen-3-yl | H | H | O |
| 56 | N-(2-dimethylamino-eth-1-yl)-N-methyl-aminocarbonyl | H | H | O |
| 57 | 3-methoxyphenyl | H | H | O |

-continued

Formula (Ia)

| Cpd | G | R₃ | R₄ | Y |
|---|---|---|---|---|
| 58 | phenylmethylamino carbonyl | ethoxy carbonyl | H | O |
| 59 | phenylaminocarbonyl | ethoxy carbonyl | H | O |
| 60 | cyclopentylaminocarbonyl | ethoxy carbonyl | H | O |
| 61 | N-(2-hydroxy-ethyl)-N-methyl-aminocarbonyl | H | H | O |
| 62 | N-[(4-trifluoromethyl)-cyclohexyl]-aminocarbonyl | H | H | O |
| 63 | 3-methanesulfonylamino-phenyl | H | H | O |
| 64 | N-2,2,2,-trifluoroethyl-aminocarbonyl | H | H | O |
| 65 | 3-[(3-methoxy)phenyl]piperidin-1-ylcarbonyl | H | H | O |
| 66 | N-4-fluorophenyl-N-methyl-aminocarbonyl | H | H | O |
| 67 | N-(1(R)-hydroxymethyl-3-methyl-but-1-yl)-aminocarbonyl | H | H | O |
| 68 | N-(dimethylamino carbonylmethyl)-N-methyl-aminocarbonyl | H | H | O |
| 69 | (3(R)-hydroxy) pyrrolidin-1-ylcarbonyl | H | H | O |
| 70 | (3(S)-hydroxy) pyrrolidin-1-ylcarbonyl | H | H | O |
| 71 | pyridin-3-yl | H | 5-methoxy | O |
| 72 | carboxy | H | H | O |
| 73 | methoxycarbonyl | H | H | O |
| 74 | methoxycarbonyl | ethoxy carbonyl | H | O |
| 75 | N-(2-hydroxy-ethyl)-N-methyl-aminocarbonyl | ethoxy carbonyl | H | O |
| 76 | methoxycarbonyl | H | H | S |
| 77 | cyano | H | H | O |
| 78 | methoxycarbonyl | H | 6-methoxy carbonyl | O |
| 79 | bromo | H | 5-methoxy | O |
| 80 | 1H-tetrazol-5-yl | H | H | O |
| 81 | 1H-tetrazol-5-yl | H | H | O |
| 82 | 1H-tetrazol-5-yl | H | 5-methoxy | O |
| 83 | phenylthio | H | H | S |
| 84 | bromo | H | H | S |
| 85 | cyano | H | H | S |
| 86 | cyano | H | H | O |
| 87 | cyano | H | H | O |
| 88 | cyano | trifluoro methyl carbonyl | H | O |
| 89 | cyano | trifluoro methyl carbonyl | H | O |
| 90 | 1H-tetrazol-5-yl | H | 5-hydroxy | O |
| 91 | 4H-[1,2,4]-oxadiazol-5-oxo-3-yl | H | H | O |
| 92 | 4H-[1,2,4]-oxadiazol-5-oxo-3-yl | H | H | O |
| 93 | 4H-[1,2,4]-oxadiazol-5-thioxo-3-yl | H | H | O |
| 94 | 4H-[1,2,4]-oxadiazol-5-thioxo-3-yl | H | H | O |
| 95 | 4H-[1,2,4]thiadiazol-5-oxo-3-yl | H | H | O |
| 96 | methoxycarbonyl | H | H | O |
| 97 | N-(2-hydroxy-1,1-dimethyl-ethyl)-aminocarbonyl | H | H | O |
| 98 | carboxy | t-butoxy carbonyl | H | O |
| 99 | carboxy | H | H | O |
| 100 | carboxy | H | H | O |
| 101 | 4H-[1,2,4]thiadiazol-5-oxo-3-yl | H | H | O |
| 102 | 1H-tetrazol-5-yl | H | H | S |
| 103 | 1H-tetrazol-5-yl | H | H | S |
| 104 | quinolin-3-yl | H | 5-methoxy | O |
| 105 | fur-3-yl | H | 5-methoxy | O |
| 106 | thien-3-yl | H | 5-methoxy | O |
| 107 | pyridin-4-yl | H | 5-methoxy | O |
| 108 | 2-methylcarbonylamino-phenyl | H | 5-methoxy | O |
| 109 | quinolin-3-yl | H | 5-hydroxy | O |
| 110 | N-(2-hydroxy-ethyl)-aminocarbonyl | H | H | O |
| 111 | 1-methyl-pyrazol-3-yl | H | H | O |
| 112 | pyridin-3-yl | H | H | S |
| 113 | 2-methylcarbonylamino-phenyl | H | H | S |
| 114 | pyridin-3-yl | methyl | H | S |
| 115 | pyridin-3-yl | 1H-imidazol 2-ylmethyl | H | S |
| 116 | pyridin-3-yl | fur-3-ylmethyl | H | S |
| 117 | pyridin-3-yl | pyridin-2-yl methyl | H | S |
| 118 | 2-methylcarbonylamino-phenyl | methyl | H | S |
| 119 | 2-methylcarbonylamino-phenyl | 1H-imidazol 2-ylmethyl | H | S |
| 120 | 2-methylcarbonylamino-phenyl | fur-3-yl methyl | H | S |
| 121 | 2-methylcarbonylamino-phenyl | pyridin-2-yl methyl | H | S |
| 122 | N-(2-hydroxy-ethyl)-aminocarbonyl | t-butoxy carbonyl | H | O |
| 123 | N-(2-hydroxy-ethyl)-aminocarbonyl | H | H | O |
| 124 | N-(2-hydroxy-ethyl)-N-methyl-aminocarbonyl | H | H | O |
| 125 | N,N-diethylamidino | H | H | O |
| 126 | N,N-diethylamidino | H | H | O |
| 127 | (3(R)-hydroxy) pyrrolidin-1-ylcarbonyl | H | H | O |
| 128 | pyridin-3-yl | trifluoro methyl carbonyl | H | O |
| 129 | pyridin-3-yl | trifluoro methyl carbonyl | H | O |
| 130 | 2-methylcarbonyl aminophenyl | trifluoro methyl carbonyl l | H | O |

-continued

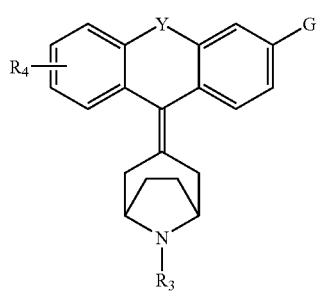

Formula (Ia)

| Cpd | G | R₃ | R₄ | Y |
|---|---|---|---|---|
| 131 | 2-methylcarbonyl aminophenyl | trifluoro methyl carbonyl | H | O |
| 132 | 4H-[1,2,4]-oxadiazol-5-oxo-3-yl | H | 5-methoxy | O |
| 133 | 4H-[1,2,4]-oxadiazol-5-thioxo-3-yl | H | 5-methoxy | O |
| 134 | 4H-[1,2,4]-oxadiazol-5-oxo-3-yl | H | 5-hydroxy | O |

BIOLOGICAL EXAMPLES

Example 1

Rat Brain Delta Opioid Receptor Binding Assay

Procedure: Male, Sprague Dawley rats (150-250 g, VAF, Charles River, Kingston, N.Y.) were killed by $CO_2$, and their brains removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand, ~4 nM [$^3$H]DPDPE at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 μL of Betaplate Scint scintillation fluid (LKB) was added and the radioactivity quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program.

Example 2

Rat Brain Mu Opioid Receptor Binding Assay

Procedure: Male, Sprague Dawley rats (150-250 g, VAF, Charles River, Kingston, N.Y.) were killed by $CO_2$, and their brains removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 μL of Betaplate Scint scintillation fluid (LKB) was added and the radioactivity quantifed on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations tested). Percent inhibition was calculated as: [(total dpm-test compound dpm)/(total dpm-nonspecific dpm)]*100. Kd and Ki values were calculated using GraphPad PRISM data analysis program.

Example 3

[$^{35}$S]GTPγS Binding Assay in NG108-15 Cell Membranes (delta opioid)

Methods: NG108-15 cell membranes were purchased from Applied Cell Sciences (Rockville, Md.). 8 mg/mL of membrane protein suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM $MgCl_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 μg/mL) were preincubated with SPA (10 mg/mL) at 25° C. for 45 min in the assay buffer. The SPA (5 mg/mL) coupled with membranes (37.5 pg/mL) was then incubated with 0.1 nM [$^{35}$] GTPγS in the same Tris buffer containing 100 μM GDP in total volume of 200 μL. Increasing concentrations of receptor agonists were used to stimulate [35S]-GTPγS binding. The basal binding was tested in the absence of agonists and non-specific binding was tested in the presence of 10 μM unlabeled GTPγS. The data were analyzed on a Packard Top Count.

DATA

% of Basal=(stimulated−non specific)*100/(basal−non specific).

$EC_{50}$ value values were calculated using GraphPad Prism.

Example 4

[$^{35}$]GTPγS Binding Assays in CHO-hMOR Cell Membranes

Methods: CHO-hMOR cell membranes were purchased from Receptor Biology, Inc. (Baltimore, Md.). About 10 mg/mL of membrane protein was suspended in 10 mM TRIS-HCl pH 7.2, 2 mM EDTA, 10% sucrose, and the suspension kept on ice. A 1 mL volume of membranes was added to 15 mL cold binding assay buffer containing 50 mM HEPES, pH 7.6, 5 mM $MgCl_2$, 100 mM NaCl, 1 mM DTT and 1 mM EDTA. The membrane suspension was homogenized with a Polytron and centrifuged at 3,000 rpm for 10 min. The supernatant was then centrifuged at 18,000 rpm for 20 min. The pellet was resuspended in 10 mL assay buffer with a Polytron. The membranes were preincubated with wheat germ agglutinin coated SPA beads (Amersham) at 25° C. for 45 min in the assay buffer. The SPA bead (5 mg/mL) coupled membranes (10 μg/mL) were then incubated with 0.5 nM [$^{35}$S] GTPγS in the assay buffer. The basal binding was that taking place in the absence of added test compound; this unmodulated binding was considered as 100%, with agonist stimulated binding rising to levels significantly above this value. A range of concentrations of receptor agonist was used to stimulate [35S]GTPγS binding. Both basal and non-specific binding was tested in the absence of agonist; non-specific binding determination included 10 μM unlabeled GTPγS.

Compounds were tested for function as antagonists by evaluating their potential to inhibit agonist-stimulated GTPγS binding. Radioactivity was quantified on a Packard TopCount. The following parameters were calculated:

$$\% \text{ stimulation} = \frac{(\text{test compound } cpm - \text{non-specific } cpm)}{(\text{basal } cpm - \text{non-specific } cpm)} \times 100.$$

$$\% \text{ inhibition} = \frac{(\% \text{ stimulation by 1 } \mu M \text{ DAMGO} - \% \text{ stimulation by test compound})}{100} \times$$

(% stimulation by 1 μM DAMGO − 100)

$EC_{50}$ values were calculated using GraphPad Prism.

| Cpd | G | $R_3$ | $R_4$ | Y |
|---|---|---|---|---|
| 1 | 1H-tetrazol-5-yl | H | H | O |
| 2 | 2-methylcarbonyl aminophenyl | H | H | O |
| 3 | N-(2-hydroxy-ethyl)-N-methyl-aminocarbonyl | H | H | O |
| 4 | 4H-[1,2,4]-oxadiazol-5-oxo-3-yl | H | H | O |
| 5 | 4H-[1,2,4]-oxadiazol-5-thioxo-3-yl | H | H | O |

-continued

| Cpd | G | $R_3$ | $R_4$ | Y |
|---|---|---|---|---|
| 6 | pyrrolidin-1-ylcarbonyl | H | H | O |
| 7 | N-(2-methoxy-ethyl)-N-methyl-aminocarbonyl | H | H | O |
| 8 | 4H-[1,2,4]thiadiazol-5-oxo-3-yl | H | H | O |
| 9 | N,N-diethylamidino | H | H | O |
| 10 | [1,2,3,5]oxathiadiazol-2-oxo-4-yl | H | H | O |
| 11 | N-(3-fluorophenyl)-methyl-aminocarbonyl | H | H | O |
| 12 | pyridin-3-yl | H | H | O |
| 13 | N-[2-(2,6-dimethylphenoxy)-1-methyl-ethyl]aminocarbonyl | H | H | O |
| 14 | N-phenyl-N-methyl-aminocarbonyl | H | H | O |
| 15 | N-(1(S)-hydroxymethyl-2-phenyl-eth-1-yl)aminocarbonyl | H | H | O |
| 16 | 2-methyl-tetrazol-5-yl | H | H | O |
| 17 | N-(2-phenylethyl)-N-methyl-aminocarbonyl | H | H | O |
| 18 | 2-aminocarbonyl-phenyl | H | H | O |
| 19 | 2-phenylethyl-aminocarbonyl | H | H | O |
| 20 | 3-methylcarbonylamino-phenyl | H | H | O |
| 21 | 1-methyl-tetrazol-5-yl | H | H | O |
| 22 | N-cyclohexyl-N-methyl-aminocarbonyl | H | H | O |
| 23 | 3-hydroxymethyl-phenyl | H | H | O |
| 24 | N-hydroxyamidino | H | H | O |
| 25 | 2-aminophenyl | H | H | O |
| 26 | 5-ethyl-1H-imidazol-2-yl | H | H | O |
| 27 | N-(1(R)-hydroxymethyl-2-phenyl-eth-1-yl)-aminocarbonyl | H | H | O |
| 28 | N,N-diisobutylamidino | H | H | O |
| 29 | pyridin-4-yl | H | H | O |
| 30 | 4-methylcarbonylamino-phenyl | H | H | O |
| 31 | N-(1S-methoxymethyl-2-phenyl-eth-1-yl)aminocarbonyl | H | H | O |
| 32 | 2-methoxypyridin-5-yl | H | H | O |
| 33 | 4,5-dihydro-1H-imidazol-2-yl | H | H | O |
| 34 | N-(4-phenyl)-cyclohexyl-aminocarbonyl | H | H | O |
| 35 | 3-methyl-4H-[1,2,4]triazol-5-yl | H | H | O |
| 36 | 5-methyl-[1,2,4]oxadiazol-4-yl | H | H | O |
| 37 | N-(1(S)-hydroxymethyl-1-methoxycarbonyl)amino carbonyl | H | H | O |
| 38 | 3-hydroxy-phenyl | H | H | O |
| 39 | isopropylamidino | H | H | O |
| 40 | phenylmethylamino carbonyl | H | H | O |
| 41 | 1,4,5,6-tetrahydro pyrimidin-2-yl | H | H | O |
| 42 | 4-aminophenyl | H | H | O |
| 43 | C-piperidin-1-yl-methyleneamine | H | H | O |
| 44 | 2-methoxyphenyl | H | H | O |
| 45 | cyclopentylaminocarbonyl | H | H | O |
| 46 | 3-methylphenyl | H | H | O |
| 47 | phenylaminocarbonyl | H | H | O |
| 48 | N,N-bis(2,2,2-trifluoro-eth-1-yl)aminocarbonyl | H | H | O |
| 49 | isobutylamidino | H | H | O |
| 50 | C-morpholin-4-yl-methyleneamine | H | H | O |
| 51 | 3-fluorophenyl | H | H | O |
| 52 | N-benzyl-N-methyl-aminocarbonyl | H | H | O |
| 53 | 4-methanesulfonyl-phenyl | H | H | O |

-continued

| Cpd | G | R₃ | R₄ | Y |
|---|---|---|---|---|
| 54 | 4-fluorophenyl | H | H | O |
| 55 | thiophen-3-yl | H | H | O |
| 56 | N-(2-dimethylamino-eth-1-yl)-N-methyl-aminocarbonyl | H | H | O |
| 57 | 3-methoxyphenyl | H | H | O |
| 58 | phenylmethylamino carbonyl | ethoxy carbonyl | H | O |
| 59 | phenylaminocarbonyl | ethoxy carbonyl | H | O |
| 60 | cyclopentylaminocarbonyl | ethoxy carbonyl | H | O |
| 61 | N-(2-dimethylamino-eth-1-yl)-N-methyl-aminocarbonyl | ethoxy carbonyl | H | O |
| 62 | N-[(4-trifluoromethyl)-cyclohexyl]-aminocarbonyl | H | H | O |
| 63 | 3-methanesulfonylamino-phenyl | H | H | O |
| 64 | N-2,2,2,-trifluoroethyl-aminocarbonyl | H | H | O |
| 65 | 3-[(3-methoxy)phenyl]piperidin-1-ylcarbonyl | H | H | O |
| 66 | N-4-fluorophenyl-N-methyl-aminocarbonyl | H | H | O |
| 67 | N-(1(R)-hydroxymethyl-3-methyl-but-1-yl)-aminocarbonyl | H | H | O |
| 68 | N-(dimethylamino carbonylmethyl)-N-methyl-aminocarbonyl | H | H | O |
| 69 | (3(R)-hydroxy) pyrrolidin-1-ylcarbonyl | H | H | O |
| 70 | (3(S)-hydroxy) pyrrolidin-1-ylcarbonyl | H | H | O |
| 71 | pyridin-3-yl | H | 5-methoxy | O |
| 72 | carboxy | H | H | O |
| 73 | methoxycarbonyl | H | H | O |
| 74 | methoxycarbonyl | ethoxy carbonyl | H | O |
| 75 | N-(2-hydroxy-ethyl)-N-methyl-aminocarbonyl | ethoxy carbonyl | H | O |
| 76 | methoxycarbonyl | H | H | S |
| 77 | cyano | H | H | O |
| 78 | methoxycarbonyl | H | 6-methoxy carbonyl | O |
| 79 | bromo | H | 5-methoxy | O |
| 80 | 1H-tetrazol-5-yl | H | H | O |
| 81 | 1H-tetrazol-5-yl | H | H | O |
| 82 | 1H-tetrazol-5-yl | H | 5-methoxy | O |
| 83 | phenylthio | H | H | S |
| 84 | bromo | H | H | S |
| 85 | cyano | H | H | S |
| 86 | cyano | H | H | O |
| 87 | cyano | H | H | O |
| 88 | cyano | trifluoro methyl carbonyl | H | O |
| 89 | cyano | trifluoro methyl carbonyl | H | O |
| 90 | 1H-tetrazol-5-yl | H | 5-hydroxy | O |
| 91 | 4H-[1,2,4]-oxadiazol-5-oxo-3-yl | H | H | O |
| 92 | 4H-[1,2,4]-oxadiazol-5-oxo-3-yl | H | H | O |
| 93 | 4H-[1,2,4]-oxadiazol-5-thioxo-3-yl | H | H | O |
| 94 | 4H-[1,2,4]-oxadiazol-5-thioxo-3-yl | H | H | O |
| 95 | 4H-[1,2,4]thiadiazol-5-oxo-3-yl | H | H | O |
| 96 | methoxycarbonyl | H | H | O |
| 97 | N-(2-hydroxy-1,1-dimethyl-ethyl)-aminocarbonyl | H | H | O |
| 98 | carboxy | t-butoxy carbonyl | H | O |
| 99 | carboxy | H | H | O |
| 100 | carboxy | H | H | O |
| 101 | 4H-[1,2,4]thiadiazol-5-oxo-3-yl | H | H | O |
| 102 | 1H-tetrazol-5-yl | H | H | S |
| 103 | 1H-tetrazol-5-yl | H | H | S |
| 104 | quinolin-3-yl | H | 5-methoxy | O |
| 105 | fur-3-yl | H | 5-methoxy | O |
| 106 | thien-3-yl | H | 5-methoxy | O |
| 107 | pyridin-4-yl | H | 5-methoxy | O |
| 108 | 2-methylcarbonylamino-phenyl | H | 5-methoxy | O |
| 109 | quinolin-3-yl | H | 5-hydroxy | O |
| 110 | N-(2-hydroxy-ethyl)-aminocarbonyl | H | H | O |
| 111 | 1-methyl-pyrazol-3-yl | H | H | O |
| 112 | pyridin-3-yl | H | H | S |
| 113 | 2-methylcarbonylamino-phenyl | H | H | S |
| 114 | pyridin-3-yl | methyl | H | S |
| 115 | pyridin-3-yl | 1H-imidazol-2-ylmethyl | H | S |
| 116 | pyridin-3-yl | fur-3-ylmethyl | H | S |
| 117 | pyridin-3-yl | pyridin-2-yl methyl | H | S |
| 118 | 2-methylcarbonylamino-phenyl | methyl | H | S |
| 119 | 2-methylcarbonylamino-phenyl | 1H-imidazol-2-ylmethyl | H | S |
| 120 | 2-methylcarbonylamino-phenyl | fur-3-yl methyl | H | S |
| 121 | 2-methylcarbonylamino-phenyl | pyridin-2-yl methyl | H | S |
| 122 | N-(2-hydroxy-ethyl)-aminocarbonyl | t-butoxy carbonyl | H | O |
| 123 | N-(2-hydroxy-ethyl)-aminocarbonyl | H | H | O |
| 124 | N-(2-hydroxy-ethyl)-N-methyl-aminocarbonyl | H | H | O |
| 125 | N,N-diethylamidino | H | H | O |
| 126 | N,N-diethylamidino | H | H | O |
| 127 | (3(R)-hydroxy) pyrrolidin-1-ylcarbonyl | H | H | O |
| 128 | pyridin-3-yl | trifluoro methyl carbonyl | H | O |
| 129 | pyridin-3-yl | trifluoro methyl carbonyl | H | O |
| 130 | 2-methylcarbonyl aminophenyl | trifluoro methyl carbonyl l | H | O |
| 131 | 2-methylcarbonyl aminophenyl | trifluoro methyl carbonyl | H | O |
| 132 | 4H-[1,2,4]-oxadiazol-5-oxo-3-yl | H | 5-methoxy | O |
| 133 | 4H-[1,2,4]-oxadiazol-5-thioxo-3-yl | H | 5-methoxy | O |
| 134 | 4H-[1,2,4]-oxadiazol-5-oxo-3-yl | H | 5-hydroxy | O |

Example 5

Rat CFA Radiant Heat Model of Inflammatory Pain

Interplanar injection of Complete Freund's Adjuvant (CFA) in rodents results in long-lasting inflammatory reaction, characterized by a chronic and a strong, hyperalgesia to both thermal and mechanical stimuli. These effects peak between 24-72 h following injection, and can last for several days to a few weeks. To assess the ability of compounds to reverse thermal hyperalgesia, male Sprague-Dawley rats (200-350 g) are given an intraplantar injection of CFA (1:1 CFA:saline, 100 μL) into their left hindpaw. Following a 24-h incubation period, response latencies on the Radiant Heat Paw Stimulator (RH) are obtained and compared to baseline (pre-CFA) latencies. The RH device automatically registers lifting of the paw from the surface of the glass. Only rats that exhibit at least a 25% reduction in response latency from baseline (i.e. hyperalgesia) are included in further analysis. Following the post CFA latency assessment, rats are dosed orally (2.5 mL/kg) with test compound or vehicle (hydroxypropylmethylcellulose, HPMC). Percent reversal of hyperalgesia is calculated for each animal as (Treatment Response−postCFA Response)/(preCFA Response−postCFA Response)×100. Therefore, a return to normal pre-CFA thresholds is defined as 100% efficacy, whereas no change from post-CFA thresholds is 0% efficacy. Average % reversal of hyperalgesia is then calculated for each treatment group (n=6-8 rats/group).

Example 6

The therapeutic effect of delta opioid agonists has been demonstrated in

Pain (Fang, (1995) Shengli Kexue Jinzhan 26:137-40; Garzon, (1995) Analgesia (Elmsford, N.Y) 1:131-44; Matthes, Maldonado, Simonin, Valverde, Slowe, Kitchen, Befort, Dierich, Le Meur and et al., (1996) Nature (London) 383:819-823; Stevens, (1996) Journal of Pharmacology and Experimental Therapeutics 276:440-8; Dondio, Ronzoni and Petrillo, (1997) Expert Opinion on Therapeutic Patents 7:1075-1098; Hutcheson, Sanchez-Blazquez, Rodriguez-Diaz, Garzon, Schmidhammer, Borsodi, Roques and Maldonado, (1999) European Journal of Pharmacology 383:29-37; Fraser, Pradhan, Clarke and Wahlestedt, (2000) Journal of Pharmacology and Experimental Therapeutics 295:1135-1141; Scheideler, (2000) Current Opinion in Central & Peripheral Nervous System Investigational Drugs 2:171-177; Wei, Brown, Takasaki, Plobeck, Delorme, Zhou, Yang, Jones, Gawell, Gagnon, Schmidt, Yue, Walpole, Payza, St-Onge, Labarre, Godbout, Jakob, Butterworth, Kamassah, Morin, Projean, Ducharme and Roberts, (2000) Journal of Medicinal Chemistry 43:3895-3905; Nagase, Yajima, Fujii, Kawamura, Narita, Kamei and Suzuki, (2001) Life Sciences 68:2227-2231; Abeyta, Dettmer, Barnes, Vega, Carta, Gallegos, Raymond-Stintz, Savage, Valenzuela and Saland, (2002) Brain Research 931:100-5. FIELD Reference Number: FIELD Journal Code:0045503 FIELD Call Number:; Cahill, Morinville, Hoffert, O'Donnell and Beaudet, (2003) Pain 101:199-208; Collina, Azzolina, Vercesi, Brusotti, Rossi, Barbieri, Lanza, Mennuni, Alcaro, Battaglia, Linati and Ghislandi, (2003) Farmaco 58:939-946; Hurley, Banfor and Hammond, (2003) Neuroscience (Oxford, United Kingdom) 118:789-796).

Inflammatory Pain States (Stein, Millan, Shippenberg, Peter and Herz, (1989) Journal of Pharmacology and Experimental Therapeutics 248:1269-75; Antonijevic, Mousa, Schaefer and Stein, (1995) Journal of Neuroscience 15:165-72; Ballet, Mauborgne, Benoliel, Bourgoin, Hamon, Cesselin and Collin, (1998) Brain Research 796:198-208; Hurley and Hammond, (2001) Journal of Neuroscience 21:2536-2545; Przewlocki and Przewlocka, (2001) European Journal of Pharmacology 429:79-91; Spetea, Rydelius, Nylander, Ahmed, Bileviciute-Ljungar, Lundeberg, Svensson and Kreicbergs, (2002) European Journal of Pharmacology 435:245-252; Bao, Jin, Zhang, Wang, Xu, Zhang, Wang, Ning, Cai, Guan, Xiao, Xu, He, Hokfelt, Zhou and Zhang, (2003) Neuron 37:121-133; Cahill, Morinville, Hoffert, O'Donnell and Beaudet, (2003) Pain 101:199-208; Martin, Matifas, Maldonado and Kieffer Brigitte, (2003) European Journal of Neuroscience 17:701-8. FIELD Reference Number: FIELD Journal Code:8918110 FIELD Call Number:; Petrillo, Angelici, Bingham, Ficalora, Garnier, Zaratin, Petrone, Pozzi, Sbacchi, Stean, Upton, Dondio and Scheideler, (2003) Journal of Pharmacology and Experimental Therapeutics 307:1079-1089).

Visceral Pain (Schmauss and Yaksh, (1984) Journal of Pharmacology and Experimental Therapeutics 228:1-12; Craft, henley, Haaseth, Hruby and Porreca, (1995) Journal of Pharmacology and Experimental Therapeutics 275:1535-42; Su, Wachtel and Gebhart, (1998) Journal of Neurophysiology 80:3112-3119; Gebhart, Su, Joshi, Ozaki and Sengupta, (1999) Progress in Pain Research and Management 14:225-235; Sora, Li, Funada, Kinsey and Uhl, (1999) European Journal of Pharmacology 366:R3-R5; Gebhart, (2000) Regional Anesthesia and Pain Medicine 25:632-638; Martin, Matifas, Maldonado and Kieffer Brigitte, (2003) European Journal of Neuroscience 17:701-8).

Lung (Kuo, Rohde, Barnes and Rogers, (1992) British Journal of Pharmacology 105:361-6; Campa, Schreiber, Bepler, Bishop, McNutt, Chang and Patz, (1996) Cancer Research 56:1695-701; Bolli, Shinmura, Tang, Kodani, Xuan, Guo and Dawn, (2002) Cardiovascular Research 55:506-519; Janssens, Leenaerts, Fernandez-Gadea, Gomez-Sanchez, Flameng, Herijgers, Meert and Borgers, (2003) PCT Int. Appl. 75 pp.; McLeod, Tulshian and Hey, (2003) Expert Opinion on Therapeutic Patents 13:1501-1512).

Cardioprotection (Schultz, Hsu, Nagase and Gross, (1998) American Journal of Physiology 274:H909-H914; Fryer, Hsu, Eells, Nagase and Gross, (1999) Circulation Research 84:846-851; Fryer, Hsu, Nagase and Gross, (2000) Journal of Pharmacology and Experimental Therapeutics 294:451-457; Fryer, Hsu and Gross, (2001) Basic Research in Cardiology 96:136-142; Fryer, Patel, Hsu and Gross, (2001) American Journal of Physiology 281:H1184-H1192; Fryer, Pratt, Hsu and Gross, (2001) Journal of Pharmacology and Experimental Therapeutics 296:642-649; Fryer, Wang, Hsu and Gross, (2001) American Journal of Physiology 280:H1346-H1353; Fryer, Wang, Hsu, Nagase and Gross, (2001) Journal of Pharmacology and Experimental Therapeutics 299:477-482; Huh, Gross, Nagase and Liang, (2001) American Journal of Physiology 280:H377-H383; Karck, Tanaka, Bolling, Simon, Su, Oeltgen and Haverich, (2001) Journal of Thoracic and Cardiovascular Surgery 122:986-992; McPherson and Yao, (2001) Anesthesiology 94:1082-1088; Patel, Hsu, Moore and Gross, (2001) Journal of Molecular and Cellular Cardiology 33:1455-1465; Rebrova, Maslov and Tam, (2001) Voprosy Meditsinskoi Khimii 47:338-345; Patel, Ludwig, Fryer, Hsu, Warltier and Gross, (2002) FASEB Journal 16:1468-1470, 10.1096/fj.02-0170fje; Sigg, Coles, Oeltgen and Iaizzo, (2002) American Journal of Physiology 282:H1953-H1960; Zhang, McPherson, Liu, Baman, McPherson, Rock and Yao, (2002) Journal of Pharmacology and Experimental Therapeutics 301:1012-1019; Patel, Hsu and Gross, (2004) Basic Research in Cardiology 99:38-45; Patel, Hsu and Gross, (2004) Life Sciences 75:129-140; Pear and Gross, (2004) Basic research in cardiology 99:29-37. FIELD Reference Number: FIELD Journal Code:0360342 FIELD Call Number; Shinmura, Nagai, Tamaki and Bolli, (2004) Basic research in cardiology 99:46-55.

Urinary Dysfunction (Dray and Metsch, (1984) Neuroscience Letters 47:81-4; Dray, (1985) Journal of Pharmacological Methods 13:157-65; Craft, henley, Haaseth, Hruby and Porreca, (1995) Journal of Pharmacology and Experimental Therapeutics 275:1535-42; Murase, Hamada and Asaki, (1996) PCT Int. Appl. 93 pp.; Su, Sengupta and Gebhart, (1997) Journal of Neurophysiology 77:1566-1580; Sezen, Kenigs and Kapusta, (1998) Journal of Pharmacology and Experimental Therapeutics 287: 238-245; Chang, Gengo, Biciunas, Ma, Pendergast and Jan, (2003) PCT Int. Appl. 73 pp.; Igari, Yanai and Goya, (2004) PCT Int. Appl. 30 pp.).

Cough (Kamei, Iwamoto, Suzuki, Nagase, Misawa and Kasuya, (1993) European Journal of Pharmacology 234:117-20; Kotzer, Hay, Dondio, Giardina, Petrillo and Underwood, (2000) Journal of Pharmacology and Experimental Therapeutics 292:803-9; McLeod, Tulshian and Hey, (2003) Expert Opinion on Therapeutic Patents 13:1501-1512).

Anxiety (Roberts, Gold, Polis, McDonald, Filliol, Kieffer and Koob, (2001) Alcoholism: Clinical and Experimental Research 25:1249-1256; Gaveriaux-Ruff and Kieffer, (2002) Neuropeptides (Edinburgh, United Kingdom) 36:62-71; Masuda, Suzuki, Takemura, Sugawara, Guo, Liu, Kawarada, Shimizu and Sugiyama, (2003) Tohoku Journal of Experimental Medicine 201:23-27; Noble and Roques, (2003) Drugs of Today 39:897-908).

Depression (Broom, Jutkiewicz, Folk, Traynor, Rice and Woods, (2002) Psychopharmacology (Berlin, Germany) 164:42-48; Broom, Jutkiewicz, Folk, Traynor, Rice and Woods, (2002) Neuropsychopharmacology 26:744-755; Broom, Jutkiewicz, Rice, Traynor and Woods, (2002) Japanese Journal of Pharmacology 90:1-6; Varona, Gil, Saracibar, Maza, Echevarria and Irazusta, (2003) Arzneimittel-Forschung 53:21-25).

Parkinsons Disease (Barneoud, Descombris, Aubin and Abrous, (2000) European journal of neuroscience 12:322-36. Hill, Hille and Brotchie, (2000) Drug News & Perspectives 13:261-268; Hudzik, Howell, Payza and Cross, (2000) European Journal of Pharmacology 396:101-107; Hille, Fox, Maneuf, Crossman and Brotchie, (2001) Experimental Neurology 172:189-198).

Example 7

The therapeutic effect of mu opioid agonists has been demonstrated in

Pain (Pasternak, (1986) Advances in Pain Research and Therapy 8:337-44; Garzon and Sanchez-Blazques, (1995) Life Sciences 56:PL237-PL242; Matthes, Maldonado, Simonin, Valverde, Slowe, Kitchen, Befort, Dierich, Le Meur and et al., (1996) Nature (London) 383:819-823; Stevens, (1996) Journal of Pharmacology and Experimental Therapeutics 276: 440-8; Dayer, Desmeules and Collart, (1997) Drugs 53:18-24; Valverde, Maldonado and Kieffer, (1998) CNS Drugs 10:1-10; Kharkevich and Churukanov, (1999) European Journal of Pharmacology 375:121-131; Pasternak, (2000) Progress in Pain Research and Management 16:147-162; Gutstein and Akil, J. G. Hardman and L. E. Limbird (2001) The pharmacological basis of therapeutics 569-619; Pasternak, (2001) Neuroscientist 7:220-231; Smith, Ross, Nielsen and Saini, (2001) European Journal of Pain (London, United Kingdom) 5:135-136; Wells, Bartlett, Ananthan and Bilsky, (2001) Journal of Pharmacology and Experimental Therapeutics 297:597-605; Abbadie and Pasternak, (2003) Handbook of Chemical Neuroanatomy 20:1-29; Collina, Azzolina, Vercesi, Brusotti, Rossi, Barbieri, Lanza, Mennuni, Alcaro, Battaglia, Linati and Ghislandi, (2003) Farmaco 58:939-946; Cowan, (2003) International Journal of Clinical Practice, Supplement 133:3-8; Hurley, Banfor and Hammond, (2003) Neuroscience (Oxford, United Kingdom) 118:789-796; Neilan, King, Rossi, Ansonoff, Pintar, Schiller and Pasternak, (2003) Brain Research 974:254-257; Porreca and Hruby, (2003) Pain 407-419; Servin, (2003) Advances in Experimental Medicine and Biology 523:245-260; Gilbert, Hosztafi, Mahurter and Pastemak, (2004) European Journal of Pharmacology 492:123-130).

Inflammatory Pain (Gutstein and Akil, J. G. Hardman and L. E. Limbird (2001) The pharmacological basis of therapeutics 569-619).

Immune Function (Renaud and Tomer, (1996) Advances in Experimental Medicine and Biology 402:63-69; Sacerdote, Bianchi, Manfredi and Panerai, (1997) Pain 72:325-330; Carrigan, Saurer, Ijames and Lysle, (2004) International Immunopharmacology 4:419-428).

Visceral Pain (Kharkevich and Churukanov, (1999) European Journal of Pharmacology 375:121-131; Gebhart, (2000) Regional Anesthesia and Pain Medicine 25:632-638; Churukanov, (2003) Eksperimental'naya i Klinicheskaya Farmakologiya 66:24-31).

Esophageal Reflux (Tonini, de Giorgio and de Ponti, (2004) Drugs 64:347-361).

Muscle Pain

Nielsen, Mathiesen and Blackburn-Munro, (2004) European Journal of Pharmacology 487:93-103).

Cancer Pain

9Gutstein and Akil, J. G. Hardman and L. E. Limbird (2001) The pharmacological basis of therapeutics 569-619; Wells, Bartlett, Ananthan and Bilsky, (2001) Journal of Pharmacology and Experimental Therapeutics 297:597-605; Valenzano, Miller, Chen, Shan, Crumley, Victory, Davies, Huang, Allie, Nolan, Rotshteyn, Kyle and Brogle, (2004) Journal of Pharmacology and Experimental Therapeutics 310:783-792).

Cough (Gutstein and Akil, J. G. Hardman and L. E. Limbird (2001) The pharmacological basis of therapeutics 569-619).

Example 8

Delta, Mu Analgesic Synergy

Delta and mu opioid agonists have been repeatedly demonstrated to produce antinociceptive synergy: (Vaught and Takemori, (1979) Journal of Pharmacology and Experimental Therapeutics 211:280-3; Vaught and Takemori, (1979) Journal of Pharmacology and Experimental Therapeutics 208:86-90; Porreca, Jiang and Tallarida, (1990) European Journal of Pharmacology 179:463-8; Sutters, Miakowski, Taiwo and Levine, (1990) Brain Research 530:290-4; Horan, Tallarida, Haaseth, Matsunaga, Hruby and Porreca, (1992) Life Sciences 50:1535-41; Malmberg and Yaksh, (1992) Journal of Pharmacology and Experimental Therapeutics 263:264-75; Adams, Tallarida, Geller and Adler, (1993) Journal of Pharmacology and Experimental Therapeutics 266:1261-7; Dykstra, Schoenbaum, Yarbrough, McNutt and Chang, (1993) Journal of Pharmacology and Experimental Therapeutics 267:875-82; Rossi, Pasternak and Bodnar, (1994) Brain Research 665:85-93; Negri, Improta, Lattanzi, Potenza, Luchetti and Melchiorri, (1995) British Journal of Pharmacology 116:2931-8; Dykstra, Granger, Allen, Zhang and Rice, (2002) Psychopharmacology (Berlin, Germany) 163: 420-429).

Example 9

Delta, Mu Reduced Side Effect Profile

Combinations of delta and mu opioid agonists have demonstrated reduced side effect profiles including fewer convulsions, lower incidence of straub tail, and attenuated respiratory depression (O'Neill, Collins, Pettit, McNutt and Chang, (1997) Journal of Pharmacology and Experimental Therapeutics 282:271-277; Su, McNutt and Chang, (1998) Journal of Pharmacology and Experimental Therapeutics 287:815-823).

Therefore compounds dually embodying delta and mu opioid pharmacologies will have greater analgesic action and a reduced side effect profile than that derived from either sole pharmacology.

What is claimed is:
1. A compound of Formula (I):

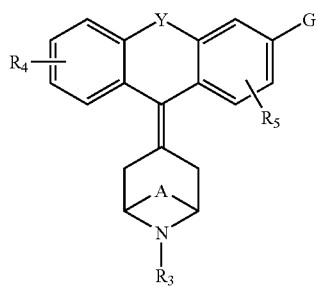

Formula (I)

wherein:
G is selected from —C(Z)NR$_1$R$_2$, 2-methylcarbonylaminophenyl, 2-aminocarbonyl-phenyl, 1H-tetrazol-5-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;
R$_1$ is hydrogen, methyl, or ethyl;
R$_2$ is selected from the group consisting of C$_{1-4}$alkanyl and phenyl; provided that when Z is O, R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, fluoro, and phenoxy; wherein the phenyl and phenoxy substituents of C$_{1-4}$alkanyl are optionally further substituted with, and the phenyl of R$_2$ is optionally substituted with, one to three substituents independently selected from the group consisting of C$_{1-6}$alkanyl, C$_{1-6}$alkanyloxy, fluoro, and hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from C$_{1-3}$alkanyl or hydroxy;
R$_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl(C$_{1-8}$)alkanyl wherein the heteroaryl is selected from the group consisting of benzo[1,3]dioxolyl, imidazolyl, furanyl, pyridinyl, thienyl, pyrimidinyl, pyrrolyl, tetrazolyl; wherein the phenyl in any phenyl-containing substituent is optionally substituted with one hydroxyl group;
R$_4$ is one to three substituents independently selected from the group consisting of hydrogen, C$_{1-4}$alkanyl, C$_{1-4}$alkanyloxy, halogen, phenyl, hydroxy, and aminocarbonyl;
R$_5$ is hydrogen;
A is —(CH$_2$)$_2$—;
Y is O—
Z is O and
enantiomers, diastereomers, tautomers, and pharmaceutically acceptable salts thereof.

2. The compound according to claim 1 wherein R$_2$ is a substituent selected from the group consisting of C$_{1-4}$alkanyl and phenyl; provided that when Z is O R$_2$ is other than unsubstituted C$_{1-4}$alkanyl; and, wherein C$_{1-4}$alkanyl is optionally substituted with one to three substituents independently selected from the group consisting of phenyl, C$_{1-4}$alkanyloxy, hydroxy, and 2,6-dimethyl-phenoxy; one to three substituents independently selected from the group consisting of C$_{1-6}$alkanyl, C$_{1-6}$alkanyloxy, fluoro, and hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from C$_{1-3}$alkanyl or hydroxy.

3. The compound according to claim 1 wherein R$_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-ylmethyl; and R$_4$ is one to two substituents independently selected from the group consisting of hydrogen, C$_{1-4}$alkanyl, C$_{1-4}$alkanyloxy, halogen, phenyl, and hydroxy.

4. The compound according to claim 1 wherein R$_3$ is a substituent selected from the group consisting of benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl; R$_4$ is one to two substituents independently selected from the group consisting of hydrogen, methyl, methoxy, bromo, fluoro, 5- or 6-phenyl, and hydroxy.

5. The compound according to claim 1 wherein R$_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl; and R$_4$ is a substituent independently selected from the group consisting of hydrogen, methyl, methoxy, bromo, fluoro, 5- or 6-phenyl, and hydroxy.

6. A compound of Formula (I):

Formula (I)

selected from the group consisting of:
- a compound of Formula (I) wherein G is 1H-tetrazol-5-yl; A is $CH_2CH_2$; $R_3$ is H; $R_4$ is H; $R_5$ is H; and Y is O;
- a compound of Formula (I) wherein G is 2-methylcarbonylaminophenyl; A is $CH_2CH_2$; $R_3$ is H; $R_4$ is H; $R_5$ is H; and Y is O;
- a compound of Formula (I) wherein G is N-(2-hydroxyethyl)-N-methyl-aminocarbonyl, A is $CH_2CH_2$; $R_3$ is H; $R_4$ is H; $R_5$ is H; and Y is O;
- a compound of Formula (I) wherein G is 4H-[1,2,4]-oxadiazol-5-oxo-3-yl; A is $CH_2CH_2$; $R_3$ is H; $R_4$ is H; $R_5$ is H; and Y is O;
- a compound of Formula (I) wherein G is 4H-[1,2,4]-oxadiazol-5-thioxo-3-yl; A is $CH_2CH_2$; $R_3$ is H; $R_4$ is H; $R_5$ is H; and Y is O;
- a compound of Formula (I) wherein G is pyrrolidin-1-ylcarbonyl; A is $CH_2CH_2$; $R_3$ is H; $R_4$ is H; $R_5$ is H; and Y is O;
- a compound of Formula (I) wherein G is N-(2-methoxyethyl)-N-methyl-aminocarbonyl; A is $CH_2CH_2$; $R_3$ is H; $R_4$ is H; $R_5$ is H; and Y is O;
- a compound of Formula (I) wherein G is 4H-[1,2,4]thiadiazol-5-oxo-3-yl; A is $CH_2CH_2$; $R_3$ is H; $R_4$ is H; $R_5$ is H; and Y is O;
- a compound of Formula (I) wherein G is N,N-diethylamidino; A is $CH_2CH_2$; $R_3$ is H; $R_4$ is H; $R_5$ is H; and Y is O;
- a compound of Formula (I) wherein G is [1,2,3,5]oxathiadiazol-2-oxo-4-yl; A is $CH_2CH_2$; $R_3$ is H; $R_4$ is H; $R_5$ is H; and Y is O;
- a compound of Formula (I) wherein G is N-(3-fluorophenyl)-methyl-aminocarbonyl; A is $CH_2CH_2$; $R_3$ is H; $R_4$ is H; $R_5$ is H; and Y is O;
- a compound of Formula (I) wherein G is pyridin-3-yl; A is $CH_2CH_2$; $R_3$ is H; $R_4$ is H; $R_5$ is H; and Y is O;
- a compound of Formula (I) wherein G is N-[2-(2,6-dimethylphenoxy)-1-methyl-ethyl]aminocarbonyl; A is $CH_2CH_2$; $R_3$ is H; $R_4$ is H; $R_5$ is H; and Y is O;
- a compound of Formula (I) wherein G is N-phenyl-N-methyl-aminocarbonyl; A is $CH_2CH_2$; $R_3$ is H; $R_4$ is H; $R_5$ is H; and Y is O;
- a compound of Formula (I) wherein G is N-(1 (S)-hydroxymethyl-2-phenyl-eth-1-yl)aminocarbonyl; A is $CH_2CH_2$; $R_3$ is H; $R_4$ is H; $R_5$ is H; and Y is O;
- a compound of Formula (I) wherein G is 2-methyl-tetrazol-5-yl; A is $CH_2CH_2$; $R_3$ is H; $R_4$ is H; $R_5$ is H; and Y is O;
- a compound of Formula (I) wherein G is N-(2-phenylethyl)-N-methyl-aminocarbonyl; A is $CH_2CH_2$; $R_3$ is H; $R_4$ is H; $R_5$ is H; and Y is O;
- a compound of Formula (I) wherein G is 2-aminocarbonyl-phenyl; A is $CH_2CH_2$; $R_3$ is H; $R_4$ is H; $R_5$ is H; and Y is O;
- a compound of Formula (I) wherein G is 2-phenylethyl-aminocarbonyl; A is $CH_2CH_2$; $R_3$ is H; $R_4$ is H; $R_5$ is H; and Y is O;
- a compound of Formula (I) wherein G is 3-methylcarbonylamino-phenyl; A is $CH_2CH_2$; $R_3$ is H; $R_4$ is H; $R_5$ is H; and Y is O;
- a compound of Formula (I) wherein G is 1-methyl-tetrazol-5-yl; A is $CH_2CH_2$; $R_3$ is H; $R_4$ is H; $R_5$ is H; and Y is O;
- a compound of Formula (I) wherein G is N-cyclohexyl-N-methyl-aminocarbonyl; A is $CH_2CH_2$; $R_3$ is H; $R_4$ is H; $R_5$ is H; and Y is O;
- a compound of Formula (I) wherein G is 3-hydroxymethyl-phenyl; A is $CH_2CH_2$; $R_3$ is H; $R_4$ is H; $R_5$ is H; and Y is O;
- a compound of Formula (I) wherein G is N-hydroxyamidino; A is $CH_2CH_2$; $R_3$ is H; $R_4$ is H; $R_5$ is H; and Y is O;
- a compound of Formula (I) wherein G is 2-aminophenyl; A is $CH_2CH_2$; $R_3$ is H; $R_4$ is H; $R_5$ is H; and Y is O;
- a compound of Formula (I) wherein G is 5-ethyl-1H-imidazol-2-yl; A is $CH_2CH_2$; $R_3$ is H; $R_4$ is H; $R_5$ is H; and Y is O;
- a compound of Formula (I) wherein G is N-(1(R)-hydroxymethyl-2-phenyl-eth-1-yl)-aminocarbonyl; A is $CH_2CH_2$; $R_3$ is H; $R_4$ is H; $R_5$ is H; and Y is O;
- a compound of Formula (I) wherein G is N, N-diisobutylamidino; A is $CH_2CH_2$; $R_3$ is H; $R_4$ is H; $R_5$ is H; and Y is O;
- a compound of Formula (I) wherein G is pyridin-4-yl; A is $CH_2CH_2$; $R_3$ is H; $R_4$ is H; $R_5$ is H; and Y is O;
- a compound of Formula (I) wherein G is 4-methylcarbonylamino-phenyl; A is $CH_2CH_2$; $R_3$ is H; $R_4$ is H; $R_5$ is H; and Y is O;
- a compound of Formula (I) wherein G is N-(1S-methoxymethyl-2-phenyl-eth-1-yl)aminocarbonyl; A is $CH_2CH_2$; $R_3$ is H; $R_4$ is H; $R_5$ is H; and Y is O;
- a compound of Formula (I) wherein G is 2-methoxypyridin-5-yl; A is $CH_2CH_2$; $R_3$ is H; $R_4$ is H; $R_5$ is H; and Y is O;
- a compound of Formula (I) wherein G is 4,5-dihydro-1H-imidazol-2-yl; A is $CH_2CH_2$; $R_3$ is H; $R_4$ is H; $R_5$ is H; and Y is O;
- a compound of Formula (I) wherein G is N-(4-phenyl)-cyclohexyl-aminocarbonyl; A is $CH_2CH_2$; $R_3$ is H; $R_4$ is H; $R_5$ is H; and Y is O;
- a compound of Formula (I) wherein G is 3-methyl-4H-[1,2,4]triazol-5-yl; A is $CH_2CH_2$; $R_3$ is H; $R_4$ is H; $R_5$ is H; and Y is O;
- a compound of Formula (I) wherein G is 5-methyl-[1,2,4]oxadiazol-4-yl; A is $CH_2CH_2$; $R_3$ is H; $R_4$ is H; $R_5$ is H; and Y is O;
- a compound of Formula (I) wherein G is N-(1 (S)-hydroxymethyl-1-methoxycarbonyl)aminocarbonyl; A is $CH_2CH_2$; $R_3$ is H; $R_4$ is H; $R_5$ is H; and Y is O;
- a compound of Formula (I) wherein G is 3-hydroxy-phenyl; A is $CH_2CH_2$; $R_3$ is H; $R_4$ is H; $R_5$ is H; and Y is O;
- a compound of Formula (I) wherein G is isopropylamidino; A is $CH_2CH_2$; $R_3$ is H; $R_4$ is H; $R_5$ is H; and Y is O;
- a compound of Formula (I) wherein G is phenylmethylaminocarbonyl; A is $CH_2CH_2$; $R_3$ is H; $R_4$ is H; $R_5$ is H; and Y is O;
- a compound of Formula (I) wherein G is 1,4,5,6-tetrahydropyrimidin-2-yl; A is $CH_2CH_2$; $R_3$ is H; $R_4$ is H; $R_5$ is H; and Y is O;
- a compound of Formula (I) wherein G is 4-aminophenyl; A is $CH_2CH_2$; $R_3$ is H; $R_4$ is H; $R_5$ is H; and Y is O;

a compound of Formula (I) wherein G is C-piperidin-1-yl-methyleneamine; A is $CH_2CH_2$; $R_3$ is H; $R_4$ is H; $R_5$ is H; and Y is O;

a compound of Formula (I) wherein G is 2-methoxyphenyl; A is $CH_2CH_2$; $R_3$ is H; $R_4$ is H; $R_5$ is H; and Y is O;

a compound of Formula (I) wherein G is cyclopentylaminocarbonyl; A is $CH_2CH_2$; $R_3$ is H; $R_4$ is H; $R_5$ is H; and Y is O;

a compound of Formula (I) wherein G is 3-methylphenyl; A is $CH_2CH_2$; $R_3$ is H; $R_4$ is H; $R_5$ is H; and Y is O;

a compound of Formula (I) wherein G is phenylaminocarbonyl; A is $CH_2CH_2$; $R_3$ is H; $R_4$ is H; $R_5$ is H; and Y is O;

a compound of Formula (I) wherein G is N,N-bis(2,2,2-trifluoro-eth-1-yl)aminocarbonyl; A is $CH_2CH_2$; $R_3$ is H; $R_4$ is H; $R_5$ is H; and Y is O;

a compound of Formula (I) wherein G is isobutylamidino; A is $CH_2CH_2$; $R_3$ is H; $R_4$ is H; $R_5$ is H; and Y is O;

a compound of Formula (I) wherein G is C-morpholin-4-yl-methyleneamine; A is $CH_2CH_2$; $R_3$ is H; $R_4$ is H; $R_5$ is H; and Y is O;

a compound of Formula (I) wherein G is 3-fluorophenyl; A is $CH_2CH_2$; $R_3$ is H; $R_4$ is H; $R_5$ is H; and Y is O;

a compound of Formula (I) wherein G is N-benzyl-N-methyl-aminocarbonyl; A is $CH_2CH_2$; $R_3$ is H; $R_4$ is H; $R_5$ is H; and Y is O;

a compound of Formula (I) wherein G is 4-methanesulfonyl-phenyl; A is $CH_2CH_2$; $R_3$ is H; $R_4$ is H; $R_5$ is H; and Y is O;

a compound of Formula (I) wherein G is 4-fluorophenyl; A is $CH_2CH_2$; $R_3$ is H; $R_4$ is H; $R_5$ is H; and Y is O;

a compound of Formula (I) wherein G is thiophen-3-yl; A is $CH_2CH_2$; $R_3$ is H; $R_4$ is H; $R_5$ is H; and Y is O;

a compound of Formula (I) wherein G is N-(2-dimethylamino-eth-1-yl)-N-methyl-aminocarbonyl; A is $CH_2CH_2$; $R_3$ is H; $R_4$ is H; $R_5$ is H; and Y is O;

a compound of Formula (I) wherein G is 3-methoxyphenyl; A is $CH_2CH_2$; $R_3$ is H; $R_4$ is H; $R_5$ is H; and Y is O;

a compound of Formula (I) wherein G is phenylmethylaminocarbonyl; A is $CH_2CH_2$; $R_3$ is ethoxycarbonyl; $R_4$ is H; $R_5$ is H; and Y is O;

a compound of Formula (I) wherein G is phenylaminocarbonyl; A is $CH_2CH_2$; $R_3$ is ethoxycarbonyl; $R_4$ is H; $R_5$ is H; and Y is O;

a compound of Formula (I) wherein G is cyclopentylaminocarbonyl; A is $CH_2CH_2$; $R_3$ is ethoxycarbonyl; $R_4$ is H; $R_5$ is H; and Y is O;

a compound of Formula (I) wherein G is N-(2-dimethylamino-eth-1-yl)-N-methyl-aminocarbonyl; A is $CH_2CH_2$; $R_3$ is ethoxycarbonyl; $R_4$ is H; $R_5$ is H; and Y is O;

a compound of Formula (I) wherein G is N-[(4-trifluoromethyl)-cyclohexyl]-aminocarbonyl; A is $CH_2CH_2$; $R_3$ is H; $R_4$ is H; $R_5$ is H; and Y is O;

a compound of Formula (I) wherein G is 3-methanesulfonylamino-phenyl; A is $CH_2CH_2$; $R_3$ is H; $R_4$ is H; $R_5$ is H; and Y is O;

a compound of Formula (I) wherein G is N-2,2,2,-trifluoroethyl-aminocarbonyl; A is $CH_2CH_2$; $R_3$ is H; $R_4$ is H; $R_5$ is H; and Y is O;

a compound of Formula (I) wherein G is 3-[(3-methoxy)phenyl]piperidin-1-ylcarbonyl; A is $CH_2CH_2$; $R_3$ is H; $R_4$ is H; $R_5$ is H; and Y is O;

a compound of Formula (I) wherein G is N-4-fluorophenyl-N-methyl-aminocarbonyl; A is $CH_2CH_2$; $R_3$ is H; $R_4$ is H; $R_5$ is H; and Y is O;

a compound of Formula (I) wherein G is N-(1(R)-hydroxymethyl-3-methyl-but-1-yl)-aminocarbonyl; A is $CH_2CH_2$; $R_3$ is H; $R_4$ is H; $R_5$ is H; and Y is O;

a compound of Formula (I) wherein G is N-(dimethylaminocarbonylmethyl)-N-methyl-aminocarbonyl; A is $CH_2CH_2$; $R_3$ is H; $R_4$ is H; $R_5$ is H; and Y is O;

a compound of Formula (I) wherein G is (3(R)-hydroxy)pyrrolidin-1-ylcarbonyl; A is $CH_2CH_2$; $R_3$ is H; $R_4$ is H; $R_5$ is H; and Y is O;

a compound of Formula (I) wherein G is (3(S)-hydroxy)pyrrolidin-1-ylcarbonyl; A is $CH_2CH_2$; $R_3$ is H; $R_4$ is H; $R_5$ is H; and Y is O;

a compound of Formula (I) wherein G is pyridin-3-yl; A is $CH_2CH_2$; $R_3$ is H; $R_4$ is 5-methoxy; $R_5$ is H; and Y is O;

a compound of Formula (I) wherein G is N-(2-hydroxyethyl)-N-methyl-aminocarbonyl; A is $CH_2CH_2$; $R_3$ is ethoxycarbonyl; $R_4$ is H; $R_5$ is H; and Y is O;

a compound of Formula (I) wherein G is 1H-tetrazol-5-yl; A is $CH_2CH_2$; $R_3$ is H; $R_4$ is H; $R_5$ is H; and Y is O;

a compound of Formula (I) wherein G is 1H-tetrazol-5-yl; A is $CH_2CH_2$; $R_3$ is H; $R_4$ is H; $R_5$ is H; and Y is O;

a compound of Formula (I) wherein G is 1H-tetrazol-5-yl; A is $CH_2CH_2$; $R_3$ is H; $R_4$ is 5-methoxy; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is H; $R_5$ is H; and Y is O;

a compound of Formula (I) wherein G is 4H-[1,2,4]thiadiazol-5-oxo-3-yl; A is $CH_2CH_2$; $R_3$ is H; $R_4$ is H; $R_5$ is H; and Y is O;

a compound of Formula (Ib) wherein G is methoxycarbonyl; A is $CH_2CH_2$; $R_3$ is H; $R_4$ is H; $R_5$ is H; and Y is O;

a compound of Formula (I) wherein G is N-(2-hydroxy-1,1-dimethyl-ethyl)-aminocarbonyl; A is $CH_2CH_2$; $R_3$ is H; $R_4$ is H; $R_5$ is H; and Y is O;

a compound of Formula (I) wherein G is 4H-[1,2,4]thiadiazol-5-oxo-3-yl; A is $CH_2CH_2$; $R_3$ is H; $R_4$ is H; $R_5$ is H; and Y is O;

a compound of Formula (I) wherein G is quinolin-3-yl; A is $CH_2CH_2$; $R_3$ is H; $R_4$ is 5-methoxy; $R_5$ is H; and Y is O;

a compound of Formula (I) wherein G is fur-3-yl; A is $CH_2CH_2$; $R_3$ is H; $R_4$ is 5-methoxy; $R_5$ is H; and Y is O;

a compound of Formula (I) wherein G is thien-3-yl; A is $CH_2CH_2$; $R_3$ is H; $R_4$ is 5-methoxy; $R_5$ is H; and Y is O;

a compound of Formula (I) wherein G is pyridin-4-yl; A is $CH_2CH_2$; $R_3$ is H; $R_4$ is 5-methoxy; $R_5$ is H; and Y is O;

a compound of Formula (I) wherein G is 2-methylcarbonylamino-phenyl; A is $CH_2CH_2$; $R_3$ is H; $R_4$ is 5-methoxy; $R_5$ is H; and Y is O;

a compound of Formula (I) wherein G is quinolin-3-yl; A is $CH_2CH_2$; $R_3$ is H; $R_4$ is 5-hydroxy; $R_5$ is H; and Y is O;

a compound of Formula (I) wherein G is N-(2-hydroxyethyl)-aminocarbonyl; A is $CH_2CH_2$; $R_3$ is H; $R_4$ is H; $R_5$ is H; and Y is O;

a compound of Formula (I) wherein G is 1-methyl-pyrazol-3-yl; A is $CH_2CH_2$; $R_3$ is H; $R_4$ is H; $R_5$ is H; and Y is O;

a compound of Formula (I) wherein G is N-(2-hydroxyethyl)-aminocarbonyl; A is $CH_2CH_2$; $R_3$ is t-butoxycarbonyl; $R_4$ is H; $R_5$ is H; and Y is O;

a compound of Formula (I) wherein G is N-(2-hydroxyethyl)-aminocarbonyl; A is $CH_2CH_2$; $R_3$ is H; $R_4$ is H; $R_5$ is H; and Y is O;

a compound of Formula (I) wherein G is N-(2-hydroxyethyl)-N-methyl-aminocarbonyl; A is $CH_2CH_2$; $R_3$ is H; $R_4$ is H; $R_5$ is H; and Y is O;

a compound of Formula (I) wherein G is N,N-diethylamidino; A is $CH_2CH_2$; $R_3$ is H; $R_4$ is H; $R_5$ is H; and Y is O;

a compound of Formula (I) wherein G is N,N-diethylamidino; A is $CH_2CH_2$; $R_3$ is H; $R_4$ is H; $R_5$ is H; and Y is O;

a compound of Formula (I) wherein G is (3(R)-hydroxy)pyrrolidin-1-ylcarbonyl; A is $CH_2CH_2$; $R_3$ is H; $R_4$ is H; $R_5$ is H; and Y is O;

a compound of Formula (I) wherein G is pyridin-3-yl; A is $CH_2CH_2$; $R_3$ is trifluoromethylcarbonyl; $R_4$ is H; $R_5$ is H; and Y is O;

a compound of Formula (I) wherein G is pyridin-3-yl; A is $CH_2CH_2$; $R_3$ is trifluoromethylcarbonyl; $R_4$ is H; $R_5$ is H; and Y is O;

a compound of Formula (I) wherein G is 2-methylcarbonylaminophenyl; A is $CH_2CH_2$; $R_3$ is trifluoromethylcarbonyl; $R_4$ is H; $R_5$ is H; and Y is O;

a compound of Formula (I) wherein G is 2-methylcarbonylaminophenyl; A is $CH_2CH_2$; $R_3$ is trifluoromethylcarbonyl; $R_4$ is H; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is 5-methoxy; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is 5-methoxy; $R_5$ is H; and Y is O; and a compound of Formula (I) wherein G is 4H-[1,2,4]-oxadiazol-5-oxo-3-yl; A is $CH_2CH_2$; $R_3$ is H; $R_4$ is 5-hydroxy; $R_5$ is H; and Y is O.

7. A compound of Formula (I):

Formula (I)

selected from the group consisting of:

a compound of Formula (I) wherein G is 1H-tetrazol-5-yl; A is $CH_2CH_2$; $R_3$ is H; $R_4$ is H; $R_5$ is H; and Y is O;

a compound of Formula (I) wherein G is 2-methylcarbonylaminophenyl; A is $CH_2CH_2$; $R_3$ is H; $R_4$ is H; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is H; $R_5$ is H; and Y is O;

a compound of Formula (I) wherein G is pyrrolidin-1-ylcarbonyl; A is $CH_2CH_2$; $R_3$ is H; $R_4$ is H; $R_5$ is H; and Y is O;

a compound of Formula (I) wherein G is N-(2-methoxyethyl)-N-methyl-aminocarbonyl; A is $CH_2CH_2$; $R_3$ is H; $R_4$ is H; $R_5$ is H; and Y is O;

a compound of Formula (I) wherein G is 4H-[1,2,4]thiadiazol-5-oxo-3-yl; A is $CH_2CH_2$; $R_3$ is H; $R_4$ is H; $R_5$ is H; and Y is O;

a compound of Formula (I) wherein G is N,N-diethylamidino; A is $CH_2CH_2$; $R_3$ is H; $R_4$ is H; $R_5$ is H; and Y is O;

a compound of Formula (I) wherein G is [1,2,3,5]oxathiadiazol-2-oxo-4-yl; A is $CH_2CH_2$; $R_3$ is H; $R_4$ is H; $R_5$ is H; and Y is O;

a compound of Formula (I) wherein G is N-(3-fluorophenyl)-methyl-aminocarbonyl; A is $CH_2CH_2$; $R_3$ is H; $R_4$ is H; $R_5$ is H; and Y is O;

a compound of Formula (I) wherein G is pyridin-3-yl; A is $CH_2CH_2$; $R_3$ is H; $R_4$ is H; $R_5$ is H; and Y is O;

a compound of Formula (I) wherein G is N-[2-(2,6-dimethylphenoxy)-1-methyl-ethyl]aminocarbonyl; A is $CH_2CH_2$; $R_3$ is H; $R_4$ is H; $R_5$ is H; and Y is O;

a compound of Formula (I) wherein G is N-phenyl-N-methyl-aminocarbonyl; A is $CH_2CH_2$; $R_3$ is H; $R_4$ is H; $R_5$ is H; and Y is O;

a compound of Formula (I) wherein G is N-(1(S)-hydroxymethyl-2-phenyl-eth-1-yl)aminocarbonyl; A is $CH_2CH_2$; $R_3$ is H; $R_4$ is H; $R_5$ is H; and Y is O;

a compound of Formula (I) wherein G is 2-methyl-tetrazol-5-yl; A is $CH_2CH_2$; $R_3$ is H; $R_4$ is H; $R_5$ is H; and Y is O;

a compound of Formula (I) wherein G is N-(2-phenylethyl)-N-methyl-aminocarbonyl; A is $CH_2CH_2$; $R_3$ is H; $R_4$ is H; $R_5$ is H; and Y is O;

a compound of Formula (I) wherein G is 2-aminocarbonylphenyl; A is $CH_2CH_2$; $R_3$ is H; $R_4$ is H; $R_5$ is H; and Y is O;

a compound of Formula (I) wherein G is 2-phenylethylaminocarbonyl; A is $CH_2CH_2$; $R_3$ is H; $R_4$ is H; $R_5$ is H; and Y is O;

a compound of Formula (I) wherein G is 3-methylcarbonylamino-phenyl; A is $CH_2CH_2$; $R_3$ is H; $R_4$ is H; $R_5$ is H; and Y is O;

a compound of Formula (I) wherein G is 1-methyl-tetrazol-5-yl; A is $CH_2CH_2$; $R_3$ is H; $R_4$ is H; $R_5$ is H; and Y is O;

a compound of Formula (I) wherein G is N-cyclohexyl-N-methyl-aminocarbonyl; A is $CH_2CH_2$; $R_3$ is H; $R_4$ is H; $R_5$ is H; and Y is O;

a compound of Formula (I) wherein G is 3-hydroxymethylphenyl; A is $CH_2CH_2$; $R_3$ is H; $R_4$ is H; $R_5$ is H; and Y is O;

a compound of Formula (I) wherein G is N-hydroxyamidino; A is $CH_2CH_2$; $R_3$ is H; $R_4$ is H; $R_5$ is H; and Y is O;

a compound of Formula (I) wherein G is 2-aminophenyl; A is $CH_2CH_2$; $R_3$ is H; $R_4$ is H; $R_5$ is H; and Y is O;

a compound of Formula (I) wherein G is 5-ethyl-1H-imidazol-2-yl; A is $CH_2CH_2$; $R_3$ is H; $R_4$ is H; $R_5$ is H; and Y is O;

a compound of Formula (I) wherein G is N-(1(R)-hydroxymethyl-2-phenyl-eth-1-yl)-aminocarbonyl; A is $CH_2CH_2$; $R_3$ is H; $R_4$ is H; $R_5$ is H; and Y is O;

a compound of Formula (I) wherein G is N,N-diisobutylamidino; A is $CH_2CH_2$; $R_3$ is H; $R_4$ is H; $R_5$ is H; and Y is O;

a compound of Formula (I) wherein G is pyridin-4-yl; A is $CH_2CH_2$; $R_3$ is H; $R_4$ is H; $R_5$ is H; and Y is O;

a compound of Formula (I) wherein G is 4-methylcarbonylamino-phenyl; A is CH₂CH₂; R₃ is H; R₄ is H; R₅ is H; and Y is O;

a compound of Formula (I) wherein G is N-(1S-methoxymethyl-2-phenyl-eth-1-yl)aminocarbonyl; A is CH₂CH₂; R₃ is H; R₄ is H; R₅ is H; and Y is O;

a compound of Formula (I) wherein G is 2-methoxypyridin-5-yl; A is CH₂CH₂; R₃ is H; R₄ is H; R₅ is H; and Y is O;

a compound of Formula (I) wherein G is 4,5-dihydro-1H-imidazol-2-yl; A is CH₂CH₂; R₃ is H; R₄ is H; R₅ is H; and Y is O;

a compound of Formula (I) wherein G is N-(4-phenyl)-cyclohexyl-aminocarbonyl; A is CH₂CH₂; R₃ is H; R₄ is H; R₅ is H; and Y is O;

a compound of Formula (I) wherein G is 3-methyl-4H-[1,2,4]triazol-5-yl; A is CH₂CH₂; R₃ is H; R₄ is H; R₅ is H; and Y is O;

a compound of Formula (I) wherein G is N-(2-dimethylamino-eth-1-yl)-N-methyl-aminocarbonyl; A is CH₂CH₂; R₃ is ethoxycarbonyl; R₄ is H; R₅ is H; and Y is O;

a compound of Formula (I) wherein G is 3-methanesulfonylamino-phenyl; A is CH₂CH₂; R₃ is H; R₄ is H; R₅ is H; and Y is O;

a compound of Formula (I) wherein G is N-2,2,2,-trifluoroethyl-aminocarbonyl; A is CH₂CH₂; R₃ is H; R₄ is H; R₅ is H; and Y is O;

a compound of Formula (I) wherein G is 3-[(3-methoxy)phenyl]piperidin-1-ylcarbonyl; A is CH₂CH₂; R₃ is H; R₄ is H; R₅ is H; and Y is O;

a compound of Formula (I) wherein G is N-4-fluorophenyl-N-methyl-aminocarbonyl; A is CH₂CH₂; R₃ is H; R₄ is H; R₅ is H; and Y is O;

a compound of Formula (I) wherein G is N-(dimethylaminocarbonylmethyl)-N-methyl-aminocarbonyl; A is CH₂CH₂; R₃ is H; R₄ is H; R₅ is H; and Y is O;

a compound of Formula (I) wherein G is (3(R)-hydroxy)pyrrolidin-1-ylcarbonyl; A is CH₂CH₂; R₃ is H; R₄ is H; R₅ is H; and Y is O;

a compound of Formula (I) wherein G is (3(S)-hydroxy)pyrrolidin-1-ylcarbonyl; A is CH₂CH₂; R₃ is H; R₄ is H; R₅ is H; and Y is O;

a compound of Formula (I) wherein G is pyridin-3-yl; A is CH₂CH₂; R₃ is H; R₄ is 5-methoxy; R₅ is H; and Y is O;

a compound of Formula (I) wherein G is 1H-tetrazol-5-yl; A is CH₂CH₂; R₃ is H; R₄ is H; R₅ is H; and Y is O;

a compound of Formula (I) wherein G is 1H-tetrazol-5-yl; A is CH₂CH₂; R₃ is H; R₄ is 5-methoxy; R₅ is H; and Y is O;

a compound of Formula (I) wherein G is 4H-[1,2,4]-oxadiazol-5-oxo-3-yl; A is CH₂CH₂; R₃ is H; R₄ is H; R₅ is H; and Y is O;

a compound of Formula (I) wherein G is 4H-[1,2,4]-oxadiazol-5-oxo-3-yl; A is CH₂CH₂; R₃ is H; R₄ is H; R₅ is H; and Y is O;

a compound of Formula (I) wherein G is 4H-[1,2,4]-oxadiazol-5-thioxo-3-yl; A is CH₂CH₂; R₃ is H; R₄ is H; R₅ is H; and Y is O;

a compound of Formula (I) wherein G is 4H-[1,2,4]-oxadiazol-5-thioxo-3-yl; A is CH₂CH₂; R₃ is H; R₄ is H; R₅ is H; and Y is O;

a compound of Formula (I) wherein G is 4H-[1,2,4]thiadiazol-5-oxo-3-yl; A is CH₂CH₂; R₃ is H; R₄ is H; R₅ is H; and Y is O;

a compound of Formula (I) wherein G is N-(2-hydroxy-1,1-dimethyl-ethyl)-aminocarbonyl; A is CH₂CH₂; R₃ is H; R₄ is H; R₅ is H; and Y is O;

a compound of Formula (I) wherein G is 4H-[1,2,4]thiadiazol-5-oxo-3-yl; A is CH₂CH₂; R₃ is H; R₄ is H; R₅ is H; and Y is O;

a compound of Formula (I) wherein G is quinolin-3-yl; A is CH₂CH₂; R₃ is H; R₄ is 5-methoxy; R₅ is H; and Y is O;

a compound of Formula (I) wherein G is fur-3-yl; A is CH₂CH₂; R₃ is H; R₄ is 5-methoxy; R₅ is H; and Y is O;

a compound of Formula (I) wherein G is thien-3-yl; A is CH₂CH₂; R₃ is H; R₄ is 5-methoxy; R₅ is H; and Y is O;

a compound of Formula (I) wherein G is pyridin-4-yl; A is CH₂CH₂; R₃ is H; R₄ is 5-methoxy; R₅ is H; and Y is O;

a compound of Formula (I) wherein G is 2-methylcarbonylamino-phenyl; A is CH₂CH₂; R₃ is H; R₄ is 5-methoxy; R₅ is H; and Y is O;

a compound of Formula (I) wherein G is quinolin-3-yl; A is CH₂CH₂; R₃ is H; R₄ is 5-hydroxy; R₅ is H; and Y is O;

a compound of Formula (I) wherein G is 1-methyl-pyrazol-3-yl; A is CH₂CH₂; R₃ is H; R₄ is H; R₅ is H; and Y is O;

a compound of Formula (I) wherein G is N-(2-hydroxyethyl)-aminocarbonyl; A is CH₂CH₂; R₃ is H; R₄ is H; R₅ is H; and Y is O;

a compound of Formula (I) wherein G is N,N-diethylamidino; A is CH₂CH₂; R₃ is H; R₄ is H; R₅ is H; and Y is O;

a compound of Formula (I) wherein G is (3(R)-hydroxy)pyrrolidin-1-ylcarbonyl; A is CH₂CH₂; R₃ is H; R₄ is H; R₅ is H; and Y is O;

a compound of Formula (I) wherein G is 4H-[1,2,4]-oxadiazol-5-oxo-3-yl; A is CH₂CH₂; R₃ is H; R₄ is 5-methoxy; R₅ is H; and Y is O;

a compound of Formula (I) wherein G is 4H-[1,2,4]-oxadiazol-5-thioxo-3-yl; A is CH₂CH₂; R₃ is H; R₄ is 5-methoxy; R₅ is H; and Y is O; and a compound of Formula (I) wherein G is 4H-[1,2,4]-oxadiazol-5-oxo-3-yl; A is CH₂CH₂; R₃ is H; R₄ is 5-hydroxy; R₅ is H; and Y is O.

8. A compound of Formula (I):

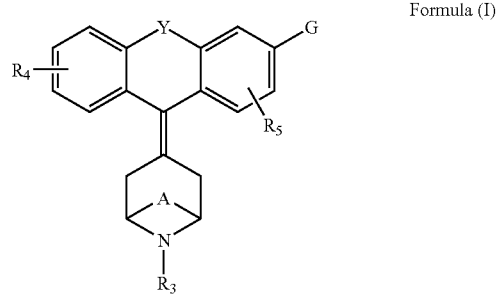

Formula (I)

selected from the group consisting of:

a compound of Formula (I) wherein G is 1H-tetrazol-5-yl; A is CH₂CH₂; R₃ is H; R₄ is H; R₅ is H; and Y is O;

a compound of Formula (I) wherein G is 2-methylcarbonylaminophenyl; A is CH₂CH₂; R₃ is H; R₄ is H; R₅ is H; and Y is O;

a compound of Formula (I) wherein G is 4H-[1,2,4]-oxadiazol-5-oxo-3-yl; A is CH₂CH₂; R₃ is H; R₄ is H; R₅ is H; and Y is O;

a compound of Formula (I) wherein G is 4H-[1,2,4]-oxadiazol-5-thioxo-3-yl; A is CH₂CH₂; R₃ is H; R₄ is H; R₅ is H; and Y is O;

a compound of Formula (I) wherein G is pyrrolidin-1-ylcarbonyl; A is CH₂CH₂; R₃ is H; R₄ is H; R₅ is H; and Y is O;

a compound of Formula (I) wherein G is N-(2-methoxyethyl)-N-methyl-aminocarbonyl; A is CH₂CH₂; R₃ is H; R₄ is H; R₅ is H; and Y is O;

a compound of Formula (I) wherein G is 4H-[1,2,4]thiadiazol-5-oxo-3-yl; A is CH₂CH₂; R₃ is H; R₄ is H; R₅ is H; and Y is O;

a compound of Formula (I) wherein G is N,N-diethylamidino; A is CH₂CH₂; R₃ is H; R₄ is H; R₅ is H; and Y is O;

a compound of Formula (I) wherein G is [1,2,3,5]oxathiadiazol-2-oxo-4-yl; A is CH₂CH₂; R₃ is H; R₄ is H; R₅ is H; and Y is O;

a compound of Formula (I) wherein G is N-(3-fluorophenyl)-methyl-aminocarbonyl; A is CH₂CH₂; R₃ is H; R₄ is H; R₅ is H; and Y is O;

a compound of Formula (I) wherein G is pyridin-3-yl; A is CH₂CH₂; R₃ is H; R₄ is H; R₅ is H; and Y is O;

a compound of Formula (I) wherein G is N-[2-(2,6-dimethylphenoxy)-1-methyl-ethyl]aminocarbonyl; A is CH₂CH₂; R₃ is H; R₄ is H; R₅ is H; and Y is O;

a compound of Formula (I) wherein G is N-phenyl-N-methyl-aminocarbonyl; A is CH₂CH₂; R₃ is H; R₄ is H; R₅ is H; and Y is O;

a compound of Formula (I) wherein G is N-(1(S)-hydroxymethyl-2-phenyl-eth-1-yl)aminocarbonyl; A is CH₂CH₂; R₃ is H; R₄ is H; R₅ is H; and Y is O;

a compound of Formula (I) wherein G is 2-methyl-tetrazol-5-yl; A is CH₂CH₂; R₃ is H; R₄ is H; R₅ is H; and Y is O;

a compound of Formula (I) wherein G is N-(2-phenylethyl)-N-methyl-aminocarbonyl; A is CH₂CH₂; R₃ is H; R₄ is H; R₅ is H; and Y is O;

a compound of Formula (I) wherein G is 2-aminocarbonylphenyl; A is CH₂CH₂; R₃ is H; R₄ is H; R₅ is H; and Y is O;

a compound of Formula (I) wherein G is 2-phenylethylaminocarbonyl; A is CH₂CH₂; R₃ is H; R₄ is H; R₅ is H; and Y is O;

a compound of Formula (I) wherein G is 3-methylcarbonylamino-phenyl; A is CH₂CH₂; R₃ is H; R₄ is H; R₅ is H; and Y is O;

a compound of Formula (I) wherein G is 1-methyl-tetrazol-5-yl; A is CH₂CH₂; R₃ is H; R₄ is H; R₅ is H; and Y is O;

a compound of Formula (I) wherein G is N-cyclohexyl-N-methyl-aminocarbonyl; A is CH₂CH₂; R₃ is H; R₄ is H; R₅ is H; and Y is O;

a compound of Formula (I) wherein G is 3-hydroxymethylphenyl; A is CH₂CH₂; R₃ is H; R₄ is H; R₅ is H; and Y is O;

a compound of Formula (I) wherein G is N-hydroxyamidino; A is CH₂CH₂; R₃ is H; R₄ is H; R₅ is H; and Y is O;

a compound of Formula (I) wherein G is 2-aminophenyl; A is CH₂CH₂; R₃ is H; R₄ is H; R₅ is H; and Y is O;

a compound of Formula (I) wherein G is 5-ethyl-1H-imidazol-2-yl; A is CH₂CH₂; R₃ is H; R₄ is H; R₅ is H; and Y is O;

a compound of Formula (I) wherein G is N-(1(R)-hydroxymethyl-2-phenyl-eth-1-yl)-aminocarbonyl; A is CH₂CH₂; R₃ is H; R₄ is H; R₅ is H; and Y is O;

a compound of Formula (I) wherein G is N-(2-dimethylamino-eth-1-yl)-N-methyl-aminocarbonyl; A is CH₂CH₂; R₃ is ethoxycarbonyl; R₄ is H; R₅ is H; and Y is O;

a compound of Formula (I) wherein G is N-2,2,2,-trifluoroethyl-aminocarbonyl; A is CH₂CH₂; R₃ is H; R₄ is H; R₅ is H; and Y is O;

a compound of Formula (I) wherein G is 3-[(3-methoxy)phenyl]piperidin-1-ylcarbonyl; A is CH₂CH₂; R₃ is H; R₄ is H; R₅ is H; and Y is O;

a compound of Formula (I) wherein G is N-4-fluorophenyl-N-methyl-aminocarbonyl; A is CH₂CH₂; R₃ is H; R₄ is H; R₅ is H; and Y is O;

a compound of Formula (I) wherein G is N-(dimethylaminocarbonylmethyl)-N-methyl-aminocarbonyl; A is CH₂CH₂; R₃ is H; R₄ is H; R₅ is H; and Y is O;

a compound of Formula (I) wherein G is (3(S)-hydroxy) pyrrolidin-1-ylcarbonyl; A is CH₂CH₂; R₃ is H; R₄ is H; R₅ is H; and Y is O;

a compound of Formula (I) wherein G is pyridin-3-yl; A is CH₂CH₂; R₃ is H; R₄ is 5-methoxy; R₅ is H; and Y is O;

a compound of Formula (I) wherein G is 1H-tetrazol-5-yl; A is CH₂CH₂; R₃ is H; R₄ is H; R₅ is H; and Y is O;

a compound of Formula (I) wherein G is 1H-tetrazol-5-yl; A is CH₂CH₂; R₃ is H; R₄ is 5-methoxy; R₅ is H; and Y is O;

a compound of Formula (I) wherein G is 4H-[1,2,4]-oxadiazol-5-oxo-3-yl; A is CH₂CH₂; R₃ is H; R₄ is H; R₅ is H; and Y is O;

a compound of Formula (I) wherein G is 4H-[1,2,4]-oxadiazol-5-oxo-3-yl; A is CH₂CH₂; R₃ is H; R₄ is H; R₅ is H; and Y is O;

a compound of Formula (I) wherein G is 4H-[1,2,4]-oxadiazol-5-thioxo-3-yl; A is CH₂CH₂; R₃ is H; R₄ is H; R₅ is H; and Y is O;

a compound of Formula (I) wherein G is 4H-[1,2,4]-oxadiazol-5-thioxo-3-yl; A is CH₂CH₂; R₃ is H; R₄ is H; R₅ is H; and Y is O;

a compound of Formula (I) wherein G is 4H-[1,2,4]thiadiazol-5-oxo-3-yl; A is CH₂CH₂; R₃ is H; R₄ is H; R₅ is H; and Y is O;

a compound of Formula (I) wherein G is fur-3-yl; A is CH₂CH₂; R₃ is H; R₄ is 5-methoxy; R₅ is H; and Y is O;

a compound of Formula (I) wherein G is 2-methylcarbonylamino-phenyl; A is CH₂CH₂; R₃ is H; R₄ is 5-methoxy; R₅ is H; and Y is O;

a compound of Formula (I) wherein G is quinolin-3-yl A is CH₂CH₂; R₃ is H; R₄ is 5-hydroxy; R₅ is H; and Y is O;

a compound of Formula (I) wherein G is N,N-diethylamidino; A is CH₂CH₂; R₃ is H; R₄ is H; R₅ is H; and Y is O;

a compound of Formula (I) wherein G is 4H-[1,2,4]-oxadiazol-5-oxo-3-yl; A is CH₂CH₂; R₃ is H; R₄ is 5-methoxy; R₅ is H; and Y is O;

a compound of Formula (I) wherein G is 4H-[1,2,4]-oxadiazol-5-thioxo-3-yl; A is CH₂CH₂; R₃ is H; R₄ is 5-methoxy; R₅ is H; and Y is O; and a compound of Formula (I) wherein G is 4H-[1,2,4]-oxadiazol-5-oxo-3-yl; A is CH₂CH₂; R₃ is H; R₄ is 5-hydroxy; R₅ is H; and Y is O.

9. A compound of Formula (I):

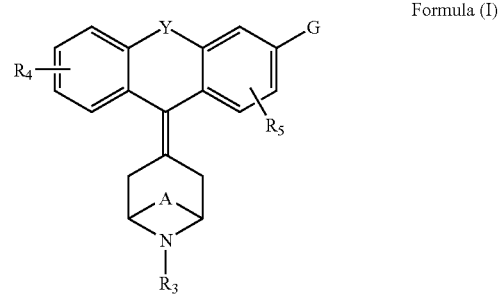

Formula (I)

selected from the group consisting of:

a compound of Formula (I) wherein G is 1H-tetrazol-5-yl; A is CH₂CH₂; R₃ is H; R₄ is H; R₅ is H; and Y is O;

a compound of Formula (I) wherein G is 2-methylcarbonylaminophenyl; A is CH₂CH₂; R₃ is H; R₄ is H; R₅ is H; and Y is O;

a compound of Formula (I) wherein G is 4H-[1,2,4]-oxadiazol-5-oxo-3-yl; A is CH₂CH₂; R₃ is H; R₄ is H; R₅ is H; and Y is O;

a compound of Formula (I) wherein G is 4H-[1,2,4]-oxadiazol-5-thioxo-3-yl; A is CH₂CH₂; R₃ is H; R₄ is H; R₅ is H; and Y is O;

a compound of Formula (I) wherein G is pyrrolidin-1-ylcarbonyl; A is $CH_2CH_2$; $R_3$ is H; $R_4$ is H; $R_5$ is H; and Y is O;

a compound of Formula (I) wherein G is N-(2-methoxyethyl)-N-methyl-aminocarbonyl; A is $CH_2CH_2$; $R_3$ is H; $R_4$ is H; $R_5$ is H; and Y is O;

a compound of Formula (I) wherein G is 4H-[1,2,4]thiadiazol-5-oxo-3-yl; A is $CH_2CH_2$; $R_3$ is H; $R_4$ is H; $R_5$ is H; and Y is O;

a compound of Formula (I) wherein G is N,N-diethylamidino; A is $CH_2CH_2$; $R_3$ is H; $R_4$ is H; $R_5$ is H; and Y is O;

a compound of Formula (I) wherein G is [1,2,3,5]oxathiadiazol-2-oxo-4-yl; A is $CH_2CH_2$; $R_3$ is H; $R_4$ is H; $R_5$ is H; and Y is O;

a compound of Formula (I) wherein G is N-(3-fluorophenyl)-methyl-aminocarbonyl; A is $CH_2CH_2$; $R_3$ is H; $R_4$ is H; $R_5$ is H; and Y is O;

a compound of Formula (I) wherein G is pyridin-3-yl; A is $CH_2CH_2$; $R_3$ is H; $R_4$ is H; $R_5$ is H; and Y is O;

a compound of Formula (I) wherein G is N-[2-(2,6-dimethylphenoxy)-1-methyl-ethyl]aminocarbonyl; A is $CH_2CH_2$; $R_3$ is H; $R_4$ is H; $R_5$ is H; and Y is O;

a compound of Formula (I) wherein G is N-phenyl-N-methyl-aminocarbonyl; A is $CH_2CH_2$; $R_3$ is H; $R_4$ is H; $R_5$ is H; and Y is O;

a compound of Formula (I) wherein G is N-(1(S)-hydroxymethyl-2-phenyl-eth-1-yl)aminocarbonyl; A is $CH_2CH_2$; $R_3$ is H; $R_4$ is H; $R_5$ is H; and Y is O;

a compound of Formula (I) wherein G is 2-methyl-tetrazol-5-yl; A is $CH_2CH_2$; $R_3$ is H; $R_4$ is H; $R_5$ is H; and Y is O;

a compound of Formula (I) wherein G is N-(2-phenylethyl)-N-methyl-aminocarbonyl; A is $CH_2CH_2$; $R_3$ is H; $R_4$ is H; $R_5$ is H; and Y is O;

a compound of Formula (I) wherein G is 2-aminocarbonylphenyl; A is $CH_2CH_2$; $R_3$ is H; $R_4$ is H; $R_5$ is H; and Y is O;

a compound of Formula (I) wherein G is 2-phenylethyl-aminocarbonyl; A is $CH_2CH_2$; $R_3$ is H; $R_4$ is H; $R_5$ is H; and Y is O;

a compound of Formula (I) wherein G is 3-methylcarbonylamino-phenyl; A is $CH_2CH_2$; $R_3$ is H; $R_4$ is H; $R_5$ is H; and Y is O;

a compound of Formula (I) wherein G is N-(2-dimethylamino-eth-1-yl)-N-methyl-aminocarbonyl; A is $CH_2CH_2$; $R_3$ is ethoxycarbonyl; $R_4$ is H; $R_5$ is H; and Y is O;

a compound of Formula (I) wherein G is N-(dimethylaminocarbonylmethyl)-N-methyl-aminocarbonyl; A is $CH_2CH_2$; $R_3$ is H; $R_4$ is H; $R_5$ is H; and Y is O;

a compound of Formula (I) wherein G is pyridin-3-yl; A is $CH_2CH_2$; $R_3$ is H; $R_4$ is 5-methoxy; $R_5$ is H; and Y is O;

a compound of Formula (I) wherein G is 1H-tetrazol-5-yl; A is $CH_2CH_2$; $R_3$ is H; $R_4$ is H; $R_5$ is H; and Y is O;

a compound of Formula (I) wherein G is 1H-tetrazol-5-yl; A is $CH_2CH_2$; $R_3$ is H; $R_4$ is 5-methoxy; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is H; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is H; $R_5$ is H; and Y is O;

a compound of Formula (I) wherein G is 4H-[1,2,4]thiadiazol-5-oxo-3-yl; A is $CH_2CH_2$; $R_3$ is H; $R_4$ is H; $R_5$ is H; and Y is O;

a compound of Formula (I) wherein G is 2-methylcarbonylamino-phenyl; A is $CH_2CH_2$; $R_3$ is H; $R_4$ is 5-methoxy; $R_5$ is H; and Y is O;

a compound of Formula (I) wherein G is quinolin-3-yl; A is $CH_2CH_2$; $R_3$ is H; $R_4$ is 5-hydroxy; $R_5$ is H; and Y is O;

a compound of Formula (I) wherein G is N,N-diethylamidino; A is $CH_2CH_2$; $R_3$ is H; $R_4$ is H; $R_5$ is H; and Y is O;

a compound of Formula (I) wherein G is 4H-[1,2,4]-oxadiazol-5-oxo-3-yl; A is $CH_2CH_2$; $R_3$ is H; $R_4$ is 5-methoxy; $R_5$ is H; and Y is O;

a compound of Formula (I) wherein G is 4H-[1,2,4]-oxadiazol-5-thioxo-3-yl; A is $CH_2CH_2$; $R_3$ is H; $R_4$ is 5-methoxy; $R_5$ is H; and Y is O; and a compound of Formula (I) wherein G is 4H-[1,2,4]-oxadiazol-5-oxo-3-yl; A is $CH_2CH_2$; $R_3$ is H; $R_4$ is 5-hydroxy; $R_5$ is H; and Y is O.

10. A compound of Formula (Ib):

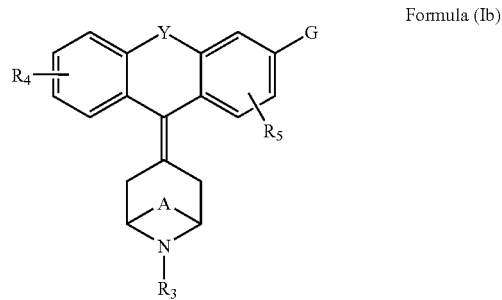

Formula (Ib)

selected from the group consisting of:

a compound of Formula (Ib) wherein G is carboxy; A is $CH_2CH_2$; $R_3$ is H; $R_4$ is H; $R_5$ is H; and Y is O;

a compound of Formula (Ib) wherein G is methoxycarbonyl; A is $CH_2CH_2$; $R_3$ is H; $R_4$ is H; $R_5$ is H; and Y is O;

a compound of Formula (Ib) wherein G is methoxycarbonyl; A is $CH_2CH_2$; $R_3$ is ethoxycarbonyl; $R_4$ is H; $R_5$ is H; and Y is O;

a compound of Formula (Ib) wherein G is cyano; A is $CH_2CH_2$; $R_3$ is H; $R_4$ is H; $R_5$ is H; and Y is O;

a compound of Formula (Ib) wherein G is methoxycarbonyl; A is $CH_2CH_2$; $R_3$ is H; $R_4$ is 6-methoxycarbonyl; $R_5$ is H; and Y is O;

a compound of Formula (Ib) wherein G is bromo; A is $CH_2CH_2$; $R_3$ is H; $R_4$ is 5-methoxy; $R_5$ is H; and Y is O;

a compound of Formula (Ib) wherein G is cyano; A is $CH_2CH_2$; $R_3$ is H; $R_4$ is H; $R_5$ is H; and Y is S;

a compound of Formula (Ib) wherein G is cyano; A is $CH_2CH_2$; $R_3$ is H; $R_4$ is H; $R_5$ is H; and Y is O;

a compound of Formula (Ib) wherein G is cyano; A is $CH_2CH_2$; $R_3$ is H; $R_4$ is H; $R_5$ is H; and Y is O;

a compound of Formula (Ib) wherein G is cyano; A is $CH_2CH_2$; $R_3$ is trifluoromethylcarbonyl; $R_4$ is H; $R_5$ is H; and Y is O;

a compound of Formula (Ib) wherein G is carboxy; A is $CH_2CH_2$; $R_3$ is t-Butoxycarbonyl; $R_4$ is H; $R_5$ is H; and Y is O;

a compound of Formula (Ib) wherein G is carboxy; A is $CH_2CH_2$; $R_3$ is H; $R_4$ is H; $R_5$ is H; and Y is O; and a compound of Formula (Ib) wherein G is carboxy; A is $CH_2CH_2$; $R_3$ is H; $R_4$ is H; $R_5$ is H; and Y is O.

11. A composition comprising the (+) enantiomer of a compound of claim 6 wherein said composition is substantially free from the (−) isomer of said compound.

12. A composition comprising the (−) enantiomer of a compound of claim 6 wherein said composition is substantially free from the (+) isomer of said compound.

13. A pharmaceutical composition comprising a compound or salt according to claim 6 admixed with a pharmaceutically acceptable carrier, excipient or diluent.

14. A veterinary composition comprising a compound or salt according to claim 6 admixed with a veterinarily acceptable carrier, excipient or diluent.

15. A kit comprising in one or more containers the composition of claim 6.

16. A pharmaceutical composition comprising a compound or salt according to claim 7 admixed with a pharmaceutically acceptable carrier, excipient or diluent.

17. A veterinary composition comprising a compound or salt according to claim 7 admixed with a veterinarily acceptable carrier, excipient or diluent.

18. A kit comprising in one or more containers the composition of claim 7.

19. A pharmaceutical composition comprising a compound or salt according to claim 8 admixed with a pharmaceutically acceptable carrier, excipient or diluent.

20. A veterinary composition comprising a compound or salt according to claim 8 admixed with a veterinarily acceptable carrier, excipient or diluent.

21. A kit comprising in one or more containers the composition of claim 8.

22. A pharmaceutical composition comprising a compound or salt according to claim 20 admixed with a pharmaceutically acceptable carrier, excipient or diluent.

23. A veterinary composition comprising a compound or salt according to claim 9 admixed with a veterinarily acceptable carrier, excipient or diluent.

24. A kit comprising in one or more containers the comosition of claim 9.

* * * * *